(12) United States Patent
Liu et al.

(10) Patent No.: US 6,949,624 B1
(45) Date of Patent: Sep. 27, 2005

(54) CLONING OF THE HUMAN NUCLEAR RECEPTOR CO-REPRESSOR GENE

(75) Inventors: Johnson M. Liu, Chevy Chase, MD (US); Jianxiang Wang, Tianjin (CN)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 645 days.

(21) Appl. No.: 09/632,033

(22) Filed: Aug. 3, 2000

Related U.S. Application Data

(60) Provisional application No. 60/146,977, filed on Aug. 3, 1999.

(51) Int. Cl.[7] ....................... A61K 38/16; C07K 14/00; C07H 21/04; C12P 21/06
(52) U.S. Cl. .................... 530/358; 530/350; 536/23.1; 536/23.5; 536/24.5; 536/23.4; 435/69.1; 435/320.1; 435/252.3
(58) Field of Search .............................. 536/23.1, 23.5, 536/23.4, 24.5; 530/350, 358; 435/69.1, 320.1, 252.3; 422/68.1

(56) References Cited

U.S. PATENT DOCUMENTS 5,644,045 A * 7/1997 Mandel et al. .............. 536/23.5
6,512,103 B1 * 1/2003 Dairaghi et al. ............ 536/23.5

OTHER PUBLICATIONS

Mandel et al. "X-linked adrenoleukodystrophy gene and corresponding protein," Database: GenEmbl, Accession NO:151114, Oct. 7, 1997.*
Alignment Result of SEQ ID NO: 2 with SEQ ID NO: 1, align2_1, Database: US–09–632–033B–1.*
Dairaghi et al. "Mammalian chemokine reagents," Database: Issued_Patents_NA, Accession NO: US–08–567–882–3/c, Dec. 8, 1995.*
Wang et al., "Nuclear receptor corepressor1" Oct. 16, 2001, Accession NO: O75376, Database: SwissProt_41 (alignment SEQ ID NO: 3).*
Wang et al., "Homo sapiens Nuclear receptor corepressor, complete cds" Sep. 1, 1998, Accession NO: AF044209, Database: GenEmbl (alignment SEQ ID NO: 1).*
Wang et al., "Homo sapiens Nuclear receptor corepressor, complete cds" Sep. 1, 1998, Accession NO: AF044209, Database: GenEmbl (alignment SEQ ID NO: 1, 3202–3618).*
Wang et al., "Homo sapiens Nuclear receptor corepressor, complete cds" Sep. 1, 1998, Accession NO: AF044209, Database: GenEmbl (alignemt SEQ ID NO: 1, 4891–5649).*
Wang et al., "Nuclear receptor corepressor1" Oct. 16, 2001, Accession NO: O75376, Database: SwissProt_41 (alignment SEQ ID NO: 3, 988–1126).*
Wang et al., "Nuclear receptor corepressor1" Oct. 16, 2001, Accession NO: O75376, Database: SwissProt_41 (alignment SEQ ID NO: 1551–1803).*
Horlein et al., "Mus musculus nuclear receptor corepressor mRNA" Oct. 19, 1996, Accession NO: U35312, Database: GenEmbl (alignment ESQ ID NO: 1).*
Alland, L., et al. (1997) Role for N–CoR and Histone Deacetylase in Sin2–Mediated Transcriptional Repression. *Nature* 387:49–55.

(Continued)

*Primary Examiner*—Jon Weber
*Assistant Examiner*—Rita Mitra
(74) *Attorney, Agent, or Firm*—Knobbe, Martens, Olson & Bear, LLP

(57) ABSTRACT

The present invention relates to the discovery of the human nuclear receptor co-repressor gene and the human nuclear receptor co-repressor protein, a molecule that recruits a complex of proteins that alters chromatin structure and mediates transcriptional repression. Novel biological tools, prophylactics, therapeutics, diagnostics, and methods of use of the foregoing are also disclosed.

6 Claims, 8 Drawing Sheets

OTHER PUBLICATIONS

Borrow, J., et al. (1996) The Translocation T(8:16)(P11;P13) Of Acute Myeloid Leukaemia Fuses a Putative Acetyltransferase to the CREB–Binding Protein. *Nature Gen.* 14:33–41.

Brehm, A., et al. (1998) Retinoblastoma Protein Recruits Histone Deacetylase to Repress Transcription. *Nature* 391:597–601.

Chen, J.D. and R.M. Evans (1995) A Transcriptional Co–Repressor That Interacts With Nuclear Hormone Receptors. *Nature* 377:454–457.

Erickson, P., et al. (1996) ETO and AML1 Phosphoproteins Are Expressed in CD34+ Hematopoietic Progenitors: Implications for t(8;21) Leukemogenesis and Monitoring Residual Disease. *Blood* 88(5):1813–1823.

Erickson, P., et al. (1992) Identification of Breakpoints in t(8;21) Acute Myelogenous Leukemia and Isolation of a Fusion Transcript, *AML1/ETO*, With Similarity to Drosophila Segmentation Gene, *runt. Blood* 80(7):1825–1831.

Erickson, P., et al. (1994) The ETO Portion of Acute Myeloid Leukemia t(8;21) Fusion Transcript Encodes a Highly Evolutionarily Conserved, Putative Transcription Factor. *Cancer Res.* 54: 1782–1786.

Evans, R.M. and S.M. Hollenberg (1988) Zinc Fingers: Gilt by Association. *Cell* 52: 1–3.

Feinstein, P., et al. (1995) Identification of Homeotic Target Genes in *Drosophila melanogaster* Including nervy, a Proto–oncogene Homologue. *Genetics* 140: 573–586.

Frank, R., et al. (1995) The AML1/ETO Fusion Protein Blocks Transactivation of the GM–CSF Promoter by AML1B. *Oncogene* 11:2667–2674.

Grignani, F., et al. (1998) Fusion Proteins of the Retinoic Acid Receptor–α Recruit Histone Deacetylase in Promyelocytic Leukaemia. *Nature* 391:815–818.

Gross, C.T. and W. McGinnis (1996) DEAF–1, A Novel Protein That Binds an Essential Region in a Deformed Response Element. *EMBO J.* 15(8):1961–1970.

Heinzel, T., et al. (1997) A Complex Containing N–CoR, mSin2 and Histone Deacetylase Mediates Transcriptional Repression. *Nature* 387:43–48.

Hong, S., et al. (1997) SMRT Corepressor Interacts with PLZF and with the PML–Retinoic Acid Receptor α (RARα) and PLZF–RARα Oncoproteins Associated with Acute Promyelocytic Leukemia. *Proc. Natl. Acad. Sci. USA.* 94:9028–9033.

Horlein, A., et al. (1995) Ligand–Independent Repression by the Thyroid Hormone Receptor Mediated by a Nuclear Receptor Co–repressor. *Nature* 377: 397–403.

Jackson, T., et al. (1997) The Partial Agonist Activity of Antagonist–Occupied Steroid Receptors Is Controlled by a Novel Hinge Domain–Binding Coactivator L7–SPA and the Corepressors N–CoR or SMRT. *Mol. Endocrinology*11(6):693–705.

Kagoshima, H., et al. (1993) The Runt Domain Identifies a New Family of Heteromeric Transcriptional Regulators. *Trends Genet.* 9(10):338–341.

Kitabayashi, I., et al. (1998) Interaction and Functional Cooperation of the Leukemia–Associated Factors AML1 and p300 in Myeloid Cell Differentiation. *EMBO J.* 17(11):2994–3004.

Kurokawa, R., et al. (1995) Polarity–Specific Activities of Retinoic Acid Receptors Determined by a Co–repressor. *Nature* 377:451–454.

Laherty, C., et al. (1997) Histone Deacetylases Associated with the mSin3 Corepressor Mediate Mad Transcriptional Repression. *Cell* 89:349–356.

Lenny, N., et al. (1995) Functional Domains of the t(8;21) Fusion Protein, AML–1/ETO. *Oncogene* 11:1761–1769.

Lin, R., et al. (1998) Role of the Histone Deacetylase Complex in Acute Promyelocytic Leukaemia. *Nature* 391:811–814.

Look, A.T. (1997) Oncogenic Transcription Factors in the Human Acute Leukemias. *Science* 278:1059–1964.

Magnaghi–Jaulin, L., et al. (1998) Retinoblastoma Protein Represses Transcription by Recruiting a Histone Deacetylase. *Nature* 391:601–605.

Mannervik, M., et al. (1999) Transcriptional Coregulators in Developments. *Science* 284:606–609.

Meyers, S., et al. (1995) The t(8;21) Fusion Protein Interferes with AML–1B–Dependent Transcriptional Activation. *Mol. Cell. Biol.* 15(4):1974–1982.

Meyers, S., et al. (1996) AML–2 is a Potential Target for Transcriptional Regulation by the t(8;21) and t(12;21) Fusion Proteins in Acute Leukemia. *Oncogene* 13: 303–312.

Miyoshi, H., et al. (1993) The t(8;21) Translocation in Acute Myeloid Leukemia Results in Production of an AML1–MTG8 Fusion Transcript. *EMBO J.* 12(7):2715–2721.

Miyoshi, H., et al. (1991) t(8;21) Breakpoints on Chromosome 21 in Acute Myeloid Leukemia are Clustered Within a Limited Region of a Single Gene, *AML1. Proc. Natl. Acad. Sci. USA* 88: 10431–10434.

Nagy, L., et al. (1997) Nuclear Receptor Repression Mediated by a Complex Containing SMRT, mSin3A, and Histone Deacetylase. *Cell* 89:373–380.

Ogryzko, V., et al. (1996) The Transcription Coactivators p300 and CBP are Histone Acetyltransferases. *Cell* 87:953–959.

Okuda, T., et al. (1996) AML1, the Target of Multiple Chromosomal Translocations in Human Leukemia is Essential for Normal Fetal Liver Hematopoiesis. *Cell* 84:321–330.

Owens, G., et al. (1991) Identification of mRNAs Associated with Programmed Cell Death in Immature Thymocytes, *Mol. Cell. Biol.* 11(8):4177–4188.

Redner, R., et al. (1999) Chromatin Remodeling and Leukemia: New Therapeutic Paradigms. *Blood* 94(2):417–428.

Wang, J., et al. (1997) Transformation Properties of the ETO Gene, Fusion Partner in t(8;21) Leukemias. *Cancer Res.* 57:2951–2955.

Wang, J., et al. (1999) Inhibitors of Histone Deacetylase Relieve ETO–Mediated Repression and Induce Differentiation of AML1–ETO Leukemia Cells. *Cancer Research* 59:2766–2769.

Wang, J., et al. (1998) ETO, Fusion Partner in t(8;21) Acute Myeloid Leukemia, Represses Transcription by Interaction with the Human N–CoR/mSin3/HDAC1 Complex. *Proc. Natl. Acad. Sci. USA* 95:10860–10865.

Wang, Q., et al. (1996) The CBFβ Subunit is Essential for CBFα2 (AML1) Function In Vivo. *Cell* 87:697–708.

Yang, X., et al. (1996) A p300/CBP–Associated Factor That Competes With the Adenoviral Oncoprotein E1A. *Nature* 382:319–324.

Yergeau, D., et al. (1997) Embryonic Lethality and Impairment of Haematopoiesis in Mice Heterozygous For an AML1–ETO Fusion Gene. *Nature Gen.* 15: 303–306.

\* cited by examiner

```
   1  MSSSGYPPNQ  GAFSTEQSRY  PPHSVQYTFP  NTRHQQEFAV  PDYRSSHLEV
  51  SQASQLLQQQ  QQQQLRRRPS  LLSEFHPGSD  RPQERRTSYE  PFHPGPSPVD
 101  HDSLESKRPR  LEQVSDSHFQ  RVSAAVLPLV  HPLPEGLRAS  ADAKKDPAFG
 151  GKHEAPSSPI  SGQPCGDDQN  ASPSKLSKEE  LIQSMDRVDR  EIAKVEQQIL
 201  KLKKKQQQLE  EEAAKPPEPE  KPVSPPPVEQ  KHRSIVQIIY  DENRKKAEEA
 251  HKIFEGLGPK  VELPLYNQPS  DTKVYHENIK  TNQVMRKKLI  LFFKRRNHAR
 301  KQREQKICQR  YDQLMEAWEK  KVDRIENNPR  RKAKESKTRE  YYEKQFPEIR
 351  KQREQQERFQ  RVGQRGAGLS  ATIARSEHEI  SEIIDGLSEQ  ENNEKQMRQL
 401  SVIPPMMFDA  EQRRVKFINM  NGLMEDPMKV  YKDRQFMNVW  TDHEKEIFKD
 451  KFIQHPKNFG  LIASYLERKS  VPDCVLYYYL  TKKNENYKAL  VRRNYGKRRG
 501  RNQQIARPSQ  EEKVEEKEED  KAEKTEKKEE  EKKDEEEKDE  KEDSKENTKE
 551  KDKIDGTAEE  TEEREQATPR  GRKTANSQGR  RKGRITRSMT  NEAAAASAAA
 601  AAATEEPPPP  LPPPPEPIST  EPVETSRWTE  EEMEVAKKGL  VEHGRNWAAI
 651  AKMVGTKSEA  QCKNFYFNYK  RRHNLDNLLQ  QHKQKTSRKP  REERDVSQCE
 701  SVASTVSAQE  DEDIEASNEE  ENPEDSEVEA  VKPSEDSPEN  ATSRGNTEPA
 751  VELEPTTETA  PSTSPSLAVP  STKPAEDESV  ETQVNDSISA  ETAEQMDVDQ
 801  QEHSAEEGSV  CDPPPATKAD  SVDVEVRVPE  NHASKVEGDN  TKERDLDRAS
 851  EKVEPRDEDL  VVAQQINAQR  PEPQSDNDSS  ATCSADEDVD  GEPERQRMFP
 901  MDSKPSLLNP  TGSILVSSPL  KPNPLDLPQL  QHRAAVIPPM  VSCTPCNIPI
 951  GTPVSGYALY  QRHIKAMHES  ALLEEQRQRQ  EQIDLECRSS  TSPCGTSKSP
1001  NREWEVLQPA  PHQLITNLPE  GVRLPTTRPT  RPPPPLIPSS  KTTVASEKPS
1051  FIMGGSISQG  TPGTYLTSHN  QASYTQETPK  PSVGSISLGL  PRQQESAKSA
1101  TLPYIKQEEF  SPRSQNSQPE  GLLVRAQHEG  VVRGTAGAIQ  EGSITRGTPT
1151  SKISVESIPS  LRGSITQGTP  ALPQTGIPTE  ALVKGSISRM  PIEDSSPEKG
1201  REEAASKGHV  IYEGKSGHIL  SYDNIKNARE  GTRSPRTAHE  ISLKRSYESV
1251  EGNIKQGMSM  RESPVSAPLE  GLICRALPRG  SPHSDLKERT  VLSGSIMQGT
1301  PRATTESFED  GLKYPKQIKR  ESPPIRAFEG  AITKGKPYDG  ITTIKEMGRS
1351  IHEIPRQDIL  TQESRKTPEV  VQSTRPIIEG  SISQGTPIKF  DNNSGQSAIK
1401  HNVKSLITGP  SKLSRGMPPL  EIVPENIKVV  ERGKYEDVKA  GETVRSRHTS
1451  VVSSGPSVLR  STLHEAPKAQ  LSPGIYDDTS  ARRTPVSYQN  TMSRGSPMMN
1501  RTSDVTIPPN  KSTNHERKST  LTPTQRESIP  AKSPVPGVDP  VVSHSPFDPH
1551  HRGSTAGEVY  WSHLPTQLDP  AMPFHRALDP  AAAAYLFQRQ  LSPTPGYPSQ
1601  YQLYAMENTR  QTILNDYITS  QQMQVNLRPD  VARGLSPREQ  PLGLPYPATR
1651  GIIDLTNMPP  TILVPHPGGT  STPPMDRITY  IPGTQITFPP  RPYNSASMSP
1701  GHPTHLAAAA  SAERERERER  EKERERERIA  AASSDLYLRP  GSEQPGRPGS
1751  HGYVRSPSPS  VRTQETMLQQ  RPSVFQGTNG  TSVITPLDPT  AQLRIMPLPA
1801  GGPSISQGLP  ASRYNTAADA  LAALVDAAAS  APQMDVSKTK  ESKHEAARLE
1851  ENLRSRSAAV  SEQQQLEQKT  LEVEKRSVQC  LYTSSAFPSG  KPQPHSSVVY
1901  SEAGKDKGPP  PKSRYEEELR  TRGKTTITAA  NFIDVIITRQ  IASDKDARER
1951  GSQSSDSSSS  LSSHRYETPS  DAIEVISPAS  SPAPPQEKLQ  TYQPEVVKAN
```

FIG. 2A-1

```
2001  QAENDPTRQY EGPLHHYRPQ QESPSPQQQL PPSSQAEGMG QVPRTHRLIT
2051  LADHICQIIT QDFARNQVSS QTPQQPPTST FQNSPSALVS TPVRTKTSNR
2101  YSPESQAQSV HHQRPGSRVS PENLVDKSRG SRPGKSPERS HVSSEPYEPI
2151  SPPQVPVVHE KQDSLLLLSQ RGAEPAEQRN DARSPGSISY LPSFFTKLEN
2201  TSPMVKSKKQ EIFRKLNSSG GGDSDMAAAQ PGTEIFNLPA VTTSGSVSSR
2251  GHSFADPASN LGLEDIIRKA LMGSFDDKVE DHGVVMSQPM GVVPGTANTS
2301  VVTSGETRRE EGDPSPHSGG VCKPKLISKS NSRKSKSPIP GQGYLGTERP
2351  SSVSSVHSEG DYHRQTPGWA WEDRPSSTGS TQFPYNPLTM RMLSSTPPTP
2401  IACAPSAVNQ AAPHQQNRIW EREPAPLLSA QYETLSDSDD
```

*FIG. 2A-2*

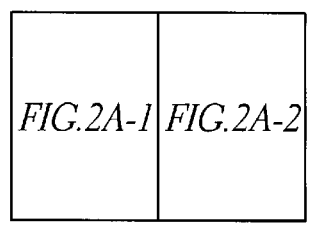

*FIG. 2A*

CLONING OF THE HUMAN NUCLEAR RECEPTOR CO-REPRESSOR GENE

This application claims priority to U.S. Provisional Application No. 60/146,977, entitled, "CLONING OF THE HUMAN NUCLEAR RECEPTOR CO-REPRESSOR GENE," filed on Aug. 3, 1999.

FIELD OF THE INVENTION

The present invention relates to the discovery of the human nuclear receptor co-repressor gene and the human nuclear receptor co-repressor protein, a molecule that recruits a complex of proteins that alters chromatin structure and mediates transcriptional repression. Novel biological tools, prophylactics, therapeutics, diagnostics, and methods of use of the foregoing are also disclosed.

BACKGROUND OF THE INVENTION

Acute myeloid leukemia (AML) is a hematologic malignancy characterized by the proliferation of a transformed clone of myeloid progenitor cells. Juxtaposition of the AML1 gene on chromosome 21 to the ETO gene on chromosome 8 fuses the amino-terminal portion of AML1 with near-full length ETO, creating the AML1/ETO chimeric fusion. (Miyoshi et al., *Proc. Natl. Acad. Sci. USA* 88: 10431–10434 (1991); Erickson et al., *Blood* 80:1825–1831 (1992); Miyoshi et al., *EMBO J.* 12: 2715–2721 (1993)). AML1 upregulates a number of target genes critical to normal hematopoiesis, whereas the AML1/ETO fusion interferes with this trans-activation.

The t(8;21)(q22;q22) translocation, associated with AML with maturation (M2 morphology), is one of the most frequently-observed nonrandom genetic alterations. (Look, A. T., *Science* 278: 1059–1964 (1997)). The portion of AML1 contained in the fusion includes a central 118 amino-acid domain homologous to the *Drosophila* segmentation gene runt (Erickson et al., *Blood* 80:1825–1831 (1992)), which serves to bind the enhancer core DNA sequence TGT/cGGT. (Kagoshima et al., *Trends Genet.* 9: 338–341 (1993)). AML1 is able to form a heterodimer with core-binding factor β (CBFβ). The AML1-CBFβ transcription factor is an important regulator of a number of target genes involved in hematopoiesis, many of which are homeobox-containing HOX genes. (Look, A. T., *Science* 278: 1059–1964 (1997), Wang et al., *Cell* 87: 697–708 (1996)). Murine embryos with targeted mutations in AML1 lacked fetal liver hematopoiesis, reinforcing the notion that AML1 is critical to normal blood cell development. (Okuda et al., *Cell* 84: 321–330 (1996)).

The AML1/ETO fusion retains the ability to interact with the enhancer core DNA sequence via the runt homology domain (RHD) and interferes with the expression of AML1-responsive target genes. (Meyers et al., *Mol. Cell. Biol.* 15: 1974–1982 (1995); Frank et al., *Oncogene* 11: 2667–2674 (1995)). In mice heterozygous for a "knocked-in" AML1/ETO allele, hematopolesis was profoundly impaired (Yergeau et al., *Nature Gen.* 15: 303–306 (1997)) as in the AML1 knock-out mice (Okuda et al., *Cell* 84: 321–330 (1996)), providing evidence that the chimeric fusion blocks wild-type AML1 function in a transdominant manner. The AML1/ETO fusion contains nearly full-length ETO, missing only a small region with no DNA-binding or transcription regulation motifs. ETO is a phosphoprotein that is normally expressed in brain tissue (Miyoshi et al., *EMBO J.* 12: 2715–2721 (1993)) and in CD34+ hematopoietic cells. (Erickson et al., *Blood* 88: 1813–1823 (1996)). Ectopic expression of ETO in NIH3T3 cells, however, leads to transformation. (Wang et al., *Cancer Res.* 57: 2951–2955 (1997)). With two zinc finger motifs and proline-rich or proline/serine/threonine-rich regions, ETO structurally resembles a transcription factor (Miyoshi et al., *EMBO J.* 12: 2715–2721 (1993); Erickson et al., *Cancer Res.* 54: 1782–1786 (1994)), although DNA-binding properties have not yet been confirmed. Mutation analysis has identified ETO sequences within the chimeric fusion as being required for the dominant repression of transcription of AML1 target genes. (Lenny et al., *Oncogene* 11: 1761–1769 (1995)).

Recently, other onco-regulatory proteins involved in transcriptional repression have been found to interact with co-repressor factors that subserve important functions in modifying chromatin structure by histone deacetylation. (Heinzel et al., *Nature* 387: 43–48 (1997); Alland et al., *Nature* 387: 49–55 (1997)). Mad and Mxi1 proteins are antagonists of the Myc family of transcription factors. Mxi1-mediated inhibition of Myc requires interaction with mammalian Sin3 (mSin3A or mSin3B) proteins. (Alland et al., *Nature* 387: 49–55 (1997)). The nuclear receptor co-repressor (N-CoR) and histone deacetylase (HDAC1) are two other members of a resultant complex that represses transcription by enzymatic deacetylation of histones and creation of a repressive chromatin structure. (Heinzel et al., *Nature* 387: 43–48 (1997); Alland et al., *Nature* 387: 49–55 (1997)). The understanding of human proteins involved in the modulation of transcriptional repressor complexes remains in its infancy.

BRIEF SUMMARY OF THE INVENTION

The invention described herein concerns the discovery of the human homolog of the murine nuclear receptor co-repressor (N-CoR), a 2,440 amino-acid polypeptide, called the human nuclear receptor co-repressor (HuN-Cor). HuN-CoR was cloned and sequenced in its entirety, and has a central domain that binds ETO. This previously unrecognized link between the ETO oncoprotein and HuN-Cor is involved in the HuN-CoR/mSin3/HDAC1 transcription repression pathway.

The interaction is mediated by two unusual zinc finger motifs present at the carboxy-terminus of ETO. HuN-CoR, Sin3 (mSin3A and B), and histone deacetylase (HDAC1) form a complex that alters chromatin structure and mediates transcriptional repression by nuclear receptors and by a number of onco-regulatory proteins. It has been found that ETO, through its interaction with the HuN-CoR/mSin3/HDAC1 complex, is a potent repressor of transcription. These novel findings shed light on how the AML1/ETO fusion inhibits expression of AML1-responsive target genes and disturbs normal hematopoiesis.

Embodiments of the invention include HuN-Cor, fragments of HuN-Cor that have an amino acid sequence not found in N-Cor, nucleic acids encoding these polypeptides, cells that have these nucleic acids and cells that express these polypeptides, antibodies that recognize these polypeptides, and software and hardware that have nucleotide or polypeptide information corresponding to these sequences. Additionally, nucleic acids that complement nucleic acids encoding HuN-Cor or fragments of HuN-Cor that have an amino acid sequence not found in N-Cor and cells that have these sequences are embodiments of the invention. Further, transcriptional repressor complexes that comprise HuN-Cor or fragments of HuN-Cor that include amino acids not found in N-Cor are aspects of the invention.

Another aspect of the invention includes agents (e.g., polypeptide fragments having sequence corresponding to HuN-Cor) that modulate the assembly of transcriptional repressor complexes comprising HuN-Cor and methods of discovering such agents. That is, agents that interact with a transcriptional repressor complex having HuN-Cor can enhance or inhibit transcriptional repression and can be used to treat or prevent HuN-Cor-related diseases (e.g., cancers including, but not limited to, leukemia). Preferred agents are fragments of HuN-Cor that contain a region that is involved in the assembly or stability of a transcriptional repressor complex and fragments of other molecules that are involved in the assembly of a transcriptional repressor complex having HuN-Cor (e.g., a polypeptide comprising a sequence of ETO that is involved in an interaction with HuN-Cor).

In other preferred embodiments, nucleic acids encoding HuN-Cor or a fragment thereof are joined to nucleic acids encoding DNA binding proteins so as to create a novel protein, upon expression in a cell, which can recruit the assembly of a transcriptional repressor complex at a specific gene. These fusion proteins are used to selectively inhibit the transcription of a specific gene. Methods of making and using these fusion proteins and constructs that encode them are also embodiments.

Additional embodiments include biotechnological tools, diagnostic assays, diagnostic kits, and methods of use of the foregoing. For example, multimeric and multimerized HuN-Cor, fragments of HuN-Cor, and nucleic acids encoding these sequences or complementary sequences are used as biotechnological tools or diagnostic reagents and these proteins or nucleic acids can be joined to a support. Supports (e.g., gene chips) having the nucleic acid embodiments or the polypeptide embodiments described herein are used for some of the diagnostic assays that are within the scope of aspects of the invention. The diagnostic embodiments preferably measure the concentration or expression level of HuN-Cor or nucleic acid encoding HuN-Cor in tested subjects and compare these values to those obtained from healthy individuals and individuals that are afflicted with a HuN-Cor-related disease (HuN-Cor disease-state profiles). HuN-Cor disease-state profiles are recorded on software and hardware and are compared with disease-state profiles of tested subjects so as to identify the presence or prevalence for disease in the tested subject. Desirably, measurements of the concentration or expression level of HuN-Cor or nucleic acids encoding HuN-Cor are made from various tissues or fluids from the body and ratios of expression level or concentration are recorded. These disease-state profiles are invaluable tools for the prognosis, diagnosis, and treatment of HuN-Cor-related diseases.

Embodimnents also include pharmaceuticals comprising the nucleic acid and polypeptide embodiments described herein. These pharmaceuticals are prepared according to conventional pharmaceutical approaches and can also include ingredients in addition to the active ingredients such as fillers, carriers, preservatives, and the like. These pharmaceuticals can be used to treat or prevent cancer and in particular are administered to treat or prevent leukemia.

DETAILED DESCRIPTION OF THE INVENTION

Figure 1A:
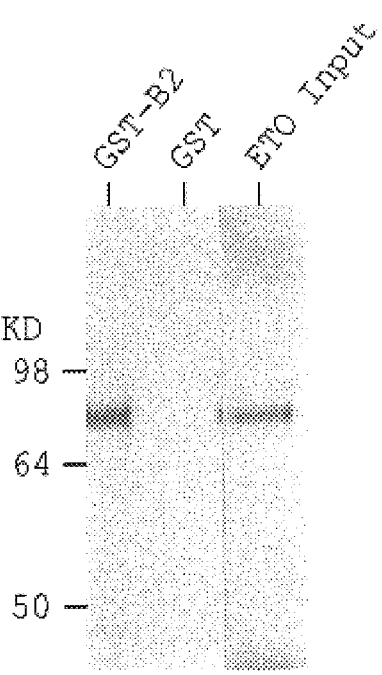
FIG. 1(A) The B2-HuN-CoR fragment was fused with glutathione S-transferase (GST). $S^{35}$-labelled ETO protein generated by in vitro translation was specifically co-precipitated by GST-B2 but not by GST alone. (B) Messenger RNA from various human tissues (Clontech) was subjected to Northern blot analysis using the B2 probe. These revealed that the hybridizing mRNA (labelled HuN-CoR) was approximately 8000 bases in size, indicating that the B2 fragment was a partial cDNA.

Disclosed herein is the discovery of the human nuclear receptor co-repressor gene (HuN-Cor) and the human nuclear receptor co-repressor protein (HuN-Cor), a 2,440-amino acid polypeptide that mediates the assembly of transcription repressor complexes, which achieve transcriptional repression by altering chromatin structure. Accordingly, evidence is provided that shows that HuN-Cor mediates the assembly of a transcriptional repressor complex comprising mammalian Sin 3 (mSin3A and B) and histone deacteylase 1 (HDAC1), a transcriptional repressor complex comprising ETO, Sin 3, and HDAC1, and a transcriptional repressor complex comprising AML1/ETO, Sin 3, and HDAC1.

Embodiments include software and hardware comprising nucleic acid sequence encoding HuN-Cor or fragments of HuN-Cor (HuN-Cor) or complements of these sequences and protein sequences corresponding to HuN-Cor and fragments of HuN-Cor. The software and hardware embodiments also include nucleic acids encoding HuN-Cor or fragments thereof having a nucleotide sequence not found in a nucleic acid sequence that encodes the murine nuclear receptor co-repressor protein ("N-Cor") and protein sequences corresponding to HuN-Cor and fragments of HuN-Cor having an amino acid sequence not found in N-Cor. Additionally, the software and hardware embodiments comprise disease-state profiles that have information such as concentrations and expression levels of HuN-Cor (e.g., mRNA) or HuN-Cor detected in biological samples from healthy subjects, as well as, subjects suffering from a HuN-Cor-related disease. The software and hardware embodiments can be used to further characterize HuN-Cor (e.g., to develop protein models of HuN-Cor, to identify homologous proteins, and to identify agents that interact with HuN-Cor) and to provide diagnostic and prognostic information that allows for the determination of the disease state of a tested individual.

Nucleic acids encoding full-length HuN-Cor or nucleic acids encoding fragments of HuN-Cor (HuN-Cor) that comprise a nucleotide sequence not found in the nucleic acid encoding N-Cor are also embodiments. Additionally, the nucleic acid embodiments include nucleic acids or derivatives thereof that are complementary to full-length HuN-Cor or fragments of HuN-Cor that comprise a nucleotide sequence not found in the nucleic acid encoding N-Cor (e.g., antisense oligonucleotides and ribozymes).

Preferred nucleic acid embodiments include nucleic acid sequences that correspond to regions of HuN-Cor that are involved in the assembly or stability of a transcriptional repressor complex. Additionally, the nucleic acid embodiments include a nucleic acid sequences that correspond to regions of ETO that are involved in the assembly or stability of a transcriptional repressor sequence. The nucleic acid embodiments can be manufactured as monomeric, multimeric, and multimerized agents. The nucleic acid embodiments also include vectors, plasmids, and recombinant constructs having nucleic acids encoding full-length HuN-Cor, fragments of HuN-Cor that comprise a nucleotide sequence not found in the nucleic acid encoding N-Cor, and fragments of ETO that are involved in the assembly or stability of a HuN-Cor-containing transcriptional repressor complex. Additional embodiments are vectors, plasmids, and recombinant constructs having nucleic acids complementary to the full-length HuN-Cor or fragments of HuN-Cor that comprise a nucleotide sequence not found in the nucleic acid encoding N-Cor. Cells having the nucleic acid embodiments, including cells in animals having a nucleic acid embodiment created by genetic engineering (e.g., cells in a transgenic animal or an oocyte), are within the scope of aspects of the invention.

Protein-based embodiments include full-length HuN-Cor and fragments of HuN-Cor that have an amino acid sequence not found in N-Cor. Additionally, the protein-based embodiments include protein derivatives or modifications of HuN-Cor, fragments of HuN-Cor that comprise an amino acid sequence not found in N-Cor, and fragments of ETO that have a region that interacts with HuN-Cor and/or effects the assembly or stability of a transcriptional repressor system. The protein-based embodiments can be manufactured as monomeric, multimeric, and multimerized agents. Cells having the protein-based embodiments, including cells in animals (e.g., cells in a transgenic animal or an oocyte), are within the scope of aspects of the invention. In some embodiments, the polypeptides described herein are used to generate antibodies. Preferred embodiments also include polyclonal and monoclonal antibodies that recognize epitopes corresponding to regions of HuN-Cor that comprise an amino acid sequence not found in N-Cor. These antibodies have application in biological assays and are used to diagnose human disease by identifying the presence of HuN-Cor in a biological sample.

In other embodiments, the modulation of the formation of transcriptional repressor complexes having HuN-Cor is achieved by using a nucleic acid embodiment. For example, a construct encoding HuN-Cor is transfected into cells so as to raise the intracellular concentration of HuN-Cor and thereby promote the formation of transcriptional repressor complexes or, alternatively, a construct encoding a nucleic acid that is complementary to a nucleic acid encoding HuN-Cor (e.g., an antisense inhibitor or a ribozyme) is used to reduce intracellular concentrations of HuN-Cor and thereby inhibit the formation of HuN-Cor-dependent transcriptional repressor complexes. Further, in some embodiments, nucleic acids encoding HuN-Cor, mutant HuN-Cor, HuN-Cor polypeptides, or ETO polypeptides are transfected and expressed in cells so as to modulate the formation of transcription repressor complexes. According to other aspects of the invention, the modulation of the formation of transcriptional repressor complexes having HuN-Cor is achieved by using a protein-based embodiment. For example, the protein-based embodiments can be delivered to cells by liposome-mediated transfer so as to raise the intracellular concentration of said embodiments and thereby promote the formation of transcriptional repressor complexes or inhibit the formation of transcriptional repressor complexes.

Approaches in rational drug design can be employed to identify novel agents that interact with HuN-Cor. These agents can be used to modulate HuN-Cor dependent transcriptional repression. In these embodiments, protein models of HuN-Cor, fragments of HuN-Cor, and agents that interact with HuN-Cor or fragments of HuN-Cor (e.g., fragments of ETO) are constructed and approaches in combinatorial chemistry are used to develop agents that modulate HuN-Cor-dependent transcriptional repression. Accordingly, novel agents that interact with HuN-Cor are developed, screened in a HuN-Cor characterization assay (e.g., a transcriptional repression assay), and the identity of each agent and its performance in a HuN-Cor characterization assay or its effect on the modulation of HuN-Cor dependent transcriptional repression is recorded on software or hardware so as to create a library of HuN-Cor modulating agents. These libraries are used to identify more agents that modulate HuN-Cor-dependent transcriptional repression and are valuable clinical tools for manufacturing and selecting an appropriate pharmaceutical to treat a particular HuN-Cor-related disease.

In preferred embodiments, nucleic acids encoding fusion proteins having HuN-Cor or fragments thereof joined to a DNA binding protein are used as agents that modulate HuN-Cor dependent transcriptional repression. For example, constructs having nucleic acids encoding HuN-Cor or fragments thereof joined to a nucleic acid encoding a DNA binding protein (e.g., AML1CBF, MyoD, POU, GATA, and homeobox proteins) are embodiments. These fusion constructs are expressed in cells for the purpose of selectively inhibiting or repressing transcription of a specific gene. Further, the fusion protein encoded by such constructs are embodied in aspects of the invention and can be delivered to cells so as to selectively inhibit or repress transcription of a specific gene. Desirable fusion proteins include HuN-Cor protein sequences joined to proteins encoding DNA binding proteins (e.g., AML1/CBF, MyoD, POU, GATA, and homeobox proteins). Constructs encoding HuN-Cor fusion proteins and the HuN-Cor fusion proteins themselves have many uses in research and therapeutic and prophylactic applications.

The nucleic acid and protein-based embodiments are also used as biotechnological tools and probes for diagnostic assays. In some aspects, for example, the nucleic acid embodiments are used as nucleic acid probes for hybridization assays, cloning, or as primers for Polymerase Chain Reaction (PCR). Similarly, the protein-based embodiments are used, for example, to identify and isolate proteins that comprise transcriptional repression complexes. Preferred diagnostic assays concern supports (e.g., gene chips) that either have the nucleic acid based or protein based embodiments disposed thereon (e.g., in an addressable array). An example is provided infra, which describes the use of a gene chip having a nucleic acid embodiment to detect the presence or absence and concentration of a HuN-Cor nucleic acid in a biological sample.

In some diagnostic embodiments, nucleic acids complementary to full-length HuN-Cor or fragments of HuN-Cor that comprise sequence not found in the nucleic acid encoding N-Cor are used to identify HuN-Cor nucleic acids (e.g., mRNA) present in a biological sample. Depending on the type of biological sample (e.g., tissue or fluid) a concentration or expression level of nucleic acid encoding HuN-Cor that is present in healthy subjects but not in subjects afflicted with HuN-Cor-related disease (e.g., cancer) can be detected. That is, an individual having a HuN-Cor related disease can have a greater or less concentration or expression level of a nucleic acid encoding HuN-Cor when compared to a healthy individual. A HuN-Cor-disease state profile comprising a concentration range of a nucleic acid encoding HuN-Cor in a specific tissue or fluid can be created for healthy and diseased individuals and these HuN-Cor disease state profiles can be compared to the concentrations or expression levels of a nucleic acid encoding HuN-Cor detected in a tested individual so as to predict the disease state of that individual. Thus, in some embodiments, the term "HuN-Cor-disease state profile" refers to the concentration or expression level or concentration range or expression level range of a nucleic acid encoding HuN-Cor that is detected in a tissue or fluid of a subject.

Further, sophisticated HuN-Cor disease-state profiles can be created by recording the concentration or expression levels of a nucleic acid encoding HuN-Cor in biological samples obtained from various tissue or fluid sources from healthy and diseased subjects. The concentration ranges of a nucleic acid encoding HuN-Cor detected in the various tissues and fluids can also be expressed as ratios and a comparison of the ratios present in healthy and diseased subjects to a tested subject allows for a diagnostic determination of the tested subjects disease state. Thus, in other embodiments, the term "HuN-Cor-disease state profile" refers to the concentration or expression level or concentration range or expression level range of a nucleic acid encoding HuN-Cor that is detected in various tissues or fluids and a HuN-Cor-disease state profile can also comprise ratios created by comparing the concentration or expression level or concentration range or expression level range of a nucleic acid encoding HuN-Cor from various tissues or fluids. Desirably, addressable arrays comprising nucleic acid probes complementary to the full-length HuN-Cor or fragments of HuN-Cor that comprise sequence not found in the nucleic acid encoding N-Cor are used to create such HuN-Cor-disease state profiles and diagnose human diseases associated with greater or less than normal levels of HuN-Cor. Such arrays or individual probes are also components of diagnostic kits.

Similarly, a HuN-Cor-disease state profile comprising concentration ranges or levels of HuN-Cor in healthy and diseased individuals can be created and can be used to predict the disease state of an individual. In some embodiments, the term "HuN-Cor-disease state profile" refers to the concentration or expression level or concentration range or expression level range of a protein corresponding to HuN-Cor that is detected in a tissue or fluid. Thus, by comparing a HuN-Cor-disease state profile from a healthy individual and a subject afflicted with a HuN-Cor related disease, such as cancer, with the HuN-Cor disease state profile from a tested subject, a clinician can rapidly diagnose the tested subject's prevalence for a HuN-Cor related disease.

Further, sophisticated HuN-Cor disease-state profiles can be created by recording the levels of HuN-Cor in biological samples obtained from various tissue or fluid sources from healthy and diseased subjects. The concentration ranges of HuN-Cor detected in the various tissues and fluids can be expressed as ratios and a comparison of the ratios generated from healthy and diseased subjects to a tested subject allows for a diagnostic determination of the subject's disease state. Thus, in other embodiments, the term "HuN-Cor-disease state profile" refers to the concentration or expression level or concentration range or expression level range of HuN-Cor that is detected in various tissues or fluids and HuN-Cor-disease state profiles can comprise ratios created by comparing the concentration or expression level or concentration range or expression level range of HuN-Cor from various tissues or fluids. Desirably, addressable arrays comprising antibodies that recognize epitopes of HuN-Cor that correspond to sequence not found in N-Cor are used to create such HuN-Cor-disease state profiles and, thereby, diagnose human diseases associated with greater or less than normal levels of HuN-Cor. Such arrays or individual probes are also components of diagnostic kits.

In the therapeutic and prophylactic embodiments, HuN-Cor, polypeptide fragments corresponding to HuN-Cor, fusion proteins comprising HuN-Cor or polypeptide fragments thereof joined to a DNA binding protein, and nucleic acids encoding these molecules are incorporated into pharmaceuticals. These pharmaceuticals can be delivered by any conventional route including, but not limited to, topical, transdermal, parenteral, gastrointestinal, transbronchial, and transalveolar. In addition to the active ingredients mentioned above, the pharmaceutical embodiments can comprise carriers or other components to facilitate or enhance drug delivery. The pharmaceutical embodiments can be used to treat or prevent HuN-Cor-related diseases (e.g., cancers such as leukemia). An example is provided infra, which describes the use of nucleic acid and/or polypeptide embodiments to induce differentiation of leukemia cells. The section below describes the discovery of the HuN-Cor gene and HuN-Cor protein and its characterization as a molecule that recruits the assembly of transcriptional repressor complexes.

Identification and Isolation of the Gene Encoding HuN-Cor and HuN-Cor Protein

A yeast two-hybrid method was used to identify potential ETO-binding proteins. The ETO gene fused to the GAL4 DNA binding domain (DBD) was used as bait to screen a human fetal brain cDNA library fused to the GAL4 activation domain. By this strategy, putative ETO-binding proteins will recruit the GAL4 activation domain to the promoter of the reporter gene resulting in expression of the reporter. A clone that strongly interacted with ETO was isolated from the cDNA library. The sequence of this 2.4 kb insert cDNA, clone B2, had greater than 90% homology with that of the murine N-CoR. (Horlein et al., Nature 377: 397–403 (1995)). The ETO-interacting protein was named the human nuclear receptor co-repressor or "HuN-CoR".

Historically, N-CoR (Horlein et al., Nature 377: 397–403 (1995); Kurokawa et al., Nature 377: 451–454 (1995)) and a related corepressor known as SMRT (silencing mediator for retinoid and thyroid-hormone receptors) (Chen, J. D. and R. M. Evans, Nature 377: 454–457 (1995)) were identified as molecules that interact with DNA-bound nuclear receptors for thyroid hormone ($T_3R$) and retinoic acid (RAR). These receptors can heterodimerize with the retinoid-X receptor (RXR). The ligand binding domain (LBD) of $T_3R$ and RAR interacts with the murine N-CoR to repress basal (ligand-independent) transcription of target genes (Horlein et al., Nature 377: 397–403 (1995); Kurokawa et al., Nature 377: 451–454 (1995)). Histone deacetylation has been proposed as a major mechanism underlying this transcriptional repression, as a result of recruitment of a repressor complex including N-CoR (or SMRT), mSin3A, and HDAC1 (Heinzel et al., Nature 387: 43–48 (1997); Nagy et al., Cell 89: 373–380 (1997)).

Glutathione-S-transferase (GST) co-precipitation assays were then used to confirm that the ETO and the HuN-CoR proteins interact in vitro. (FIG. 1A). The B2 DNA fragment was inserted into pGEX-5X-1 in order to fuse the fragment with GST. GST and GST-B2 fusion proteins were expressed in E. Coli and purified. Equal amounts of protein were immobilized on glutathione beads and incubated with in vitro-translated ETO labelled with $S^{35}$-methionine. After extensive washing, the eluted proteins were subjected to electrophoresis and autoradiography. ETO was specifically precipitated by GST-B2, but not by GST alone. (FIG. 1A). This result confirmed the physical interaction between ETO and the B2 HuN-CoR fragment.

Figure 1B:
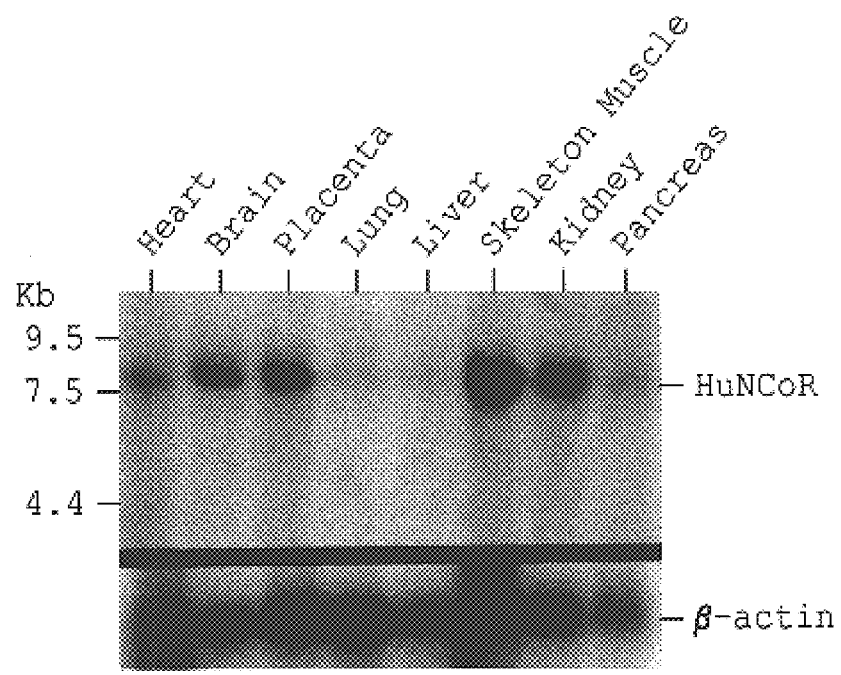

The B2 HuN-CoR fragment identified from the yeast two-hybrid assays was 2.4 kb in size. Using this fragment as a probe, Northern blot hybridization analysis revealed an approximately 8 kb transcript. (FIG. 1B). This result indicated that the HuN-CoR cDNA fragment isolated by the yeast two-hybrid screen was only a partial cDNA sequence. A human fetal brain cDNA library was then screened to clone the full-length HuN-CoR. Six overlapping fragments were obtained, which constituted the full-length HuN-CoR, encoding a 2,440 amino-acid polypeptide with 96% similarity and 92% identity to N-CoR. (FIG. 2A).

Figure 2B:
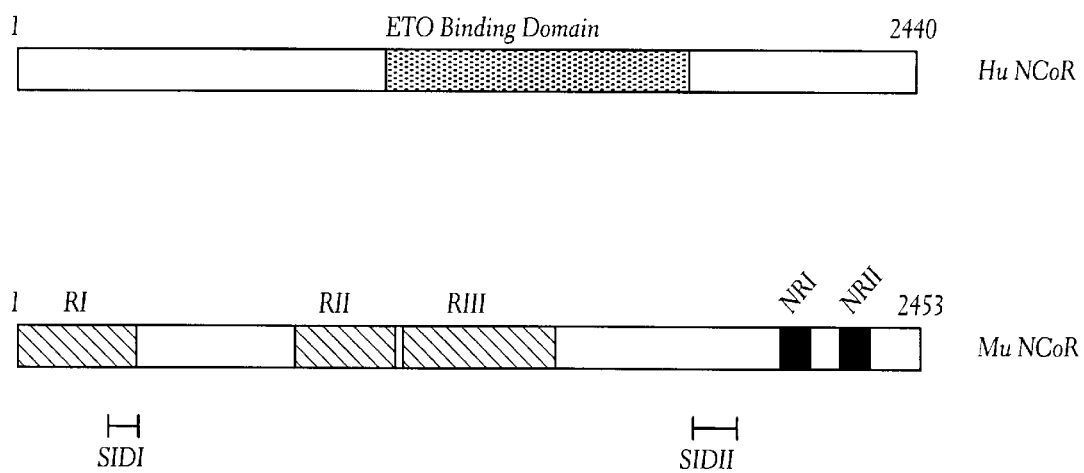
FIG. 2(A) Using B2 as a probe, a human fetal brain cDNA library was screened in order to obtain the full-length sequence of the ETO-binding protein, human nuclear receptor co-repressor (HuN-CoR). Shown is the complete amino acid sequence (GenBank Accession Number AF044209). (B) The structure of the murine N-CoR (Mu N-COR) can be divided into domains that mediate repression ($R_I$, $R_{II}$, $R_{III}$), interact with the nuclear receptor ($NR_I$, $NR_{II}$), or that interact with the Sin3 co-repressor complex ($SID_I$, $SID_{II}$). By comparison with the functional domains of Mu N-CoR, the ETO-binding domain of Hu N-CoR lies between $SID_I$ and $SID_{II}$ and roughly corresponds to $R_{III}$.

In functional assays, HuN-CoR acted similarly to N-CoR in suppressing RAR-RXR-induced transcriptional activation. The structure of the murine N-CoR can be divided into distinct functional domains that mediate repression (RI, RII, RIII) (Horlein et al., Nature 377: 397–403 (1995)), interact with the nuclear receptor (NRI, NRII) (Horlein et al., Nature 377: 397–403 (1995)), or that interact with the Sin3 co-repressor complex (SIDI, SIDII) (Heinzel et al., Nature 387: 43–48 (1997)). (FIG. 2B). The yeast two-hybrid analyses, described above, demonstrated that the region of the HuN-CoR that binds ETO includes residues 988 to 1,816. By comparison with the functional domains of N-CoR, the ETO-binding domain therefore lies between SIDI and SIDII and roughly corresponds to RIII. (FIG. 2B).

Figure 3A:
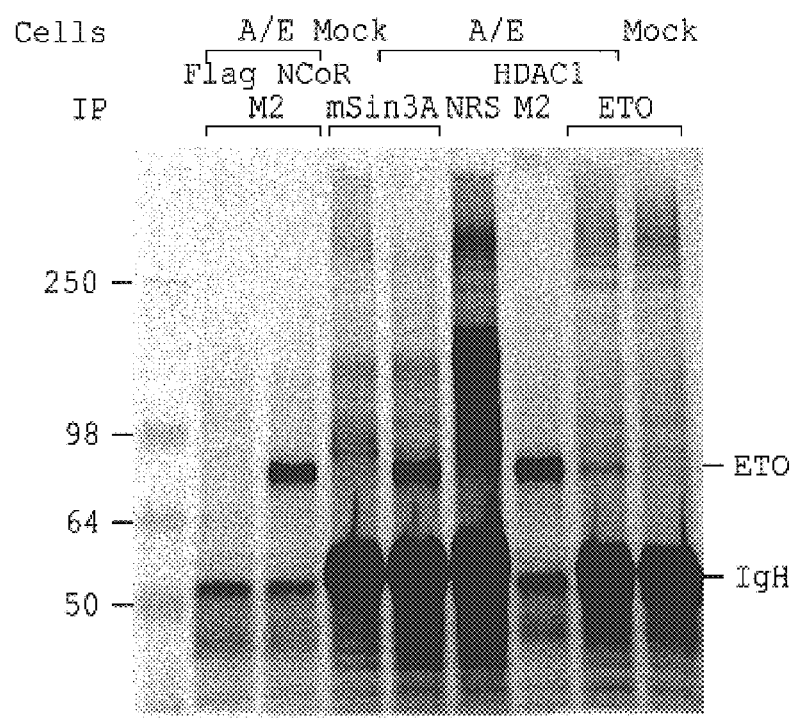
FIG. 3(A) ETO associates with the N-CoR/mSin3A/HDAC1 complex in vivo. Cells were transfected with ETO alone or with Flag, N-CoR/Flag or HDAC1/Flag. Immunoprecipitation (IP) was performed using either the M2 anti-FLAG antibody (against Flag, N-CoR/Flag or HDAC1/Flag) or antibody against mSin3A. Normal rabbit serum (NRS) was used as negative control for the IP antibody. Following immunoprecipitation, ETO specifically associated with the N-CoR/mSin3A/HDAC1 complex, as demonstrated by Western blot with an anti-ETO antibody. Cell lysates from ETO-transfected and untransfected (mock) cells, precipitated by anti-ETO antibody, were used as positive and negative controls, respectively (¼ amount of lysate used as for the other experiments). Molecular mass markers are shown in kilodaltons. (B) AML1/ETO (abbreviated A/A/E≅) associates with the N-CoR/mSin3A/HDAC1 complex in vivo. Cells were transfected with A/E, alone or with Flag, N-CoR/Flag, or HDAC1/Flag. Following IP, proteins were subjected to Western blotting using anti-AML1/RHD antibody. Proteins from lysates of A/E-transfected or mock-transfected cells precipitated by ETO antibody and blotted by AML1/RHD antibody were used as positive and negative controls for the AML1/ETO protein (14 amount of lysate used as for the other experiments). The doublet band (denoted by the double tick) seen in the figure may be due to translation at different ATG start codons.

Once it was determined that ETO interacted with a central domain of the HuN-CoR, experiments were performed to determine whether ETO was able to associate with other members of the co-repressor complex. Accordingly, 293 cells were transfected with a construct expressing ETO alone or with a plasmid expressing either the Flag epitope, N-CoR/Flag or HDAC1/Flag. Immunoprecipitation was then performed using either the M2 anti-FLAG antibody (against Flag, N-CoR/Flag or HDAC1/Flag) or an antibody against mSin3A. (FIG. 3A). Immunoprecipitation and Western blot with an anti-ETO antibody revealed that ETO specifically associated with the N-CoR/mSin3A/HDAC1 co-repressor complex. These results proved that the ETO protein forms a complex with N-CoR, mSin3A, and HDAC1 in vivo and established that HuN-Cor, mSin3A, and HDAC1 can form a transcriptional repressor complex.

Figure 3B:
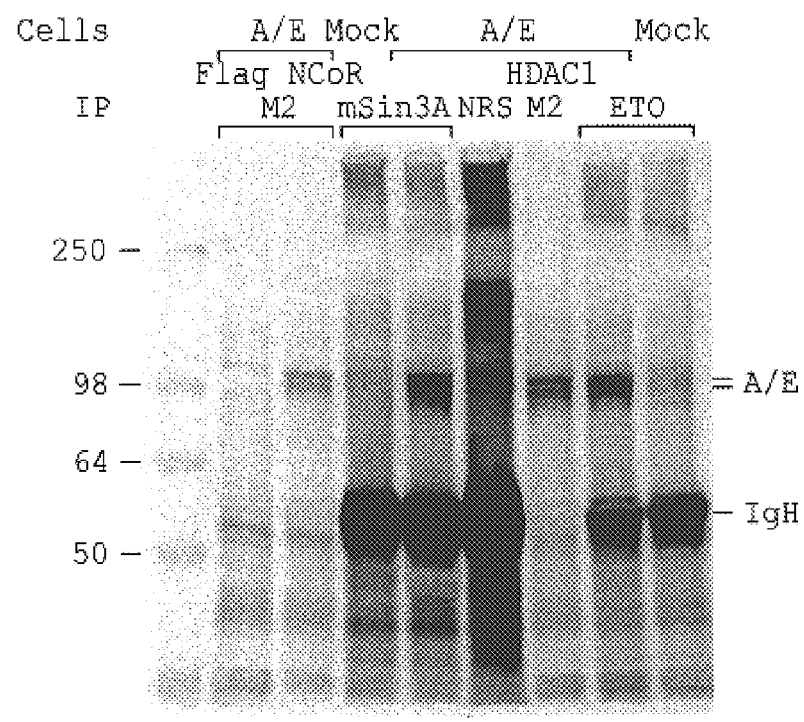

Because the AML1/ETO chimeric protein contains near full-length ETO protein, it was hypothesized that the AML1/ETO protein could associate with the co-repressor complex through ETO residues. To confirm this hypothesis, 293 cells were transfected with AML1/ETO, alone or with Flag, N-CoR/Flag, or HDAC1/Flag. (FIG. 3B). Cell lysates were prepared from transfected and mock-transfected 293 cells. Either the M2 antibody or an anti-mSin3A antibody were used for immunoprecipitation, after which, Western blotting was performed using an anti-AML1/RHD antibody. It was found that the AML1/ETO protein co-precipitated with N-CoR, mSin3A and HDAC1, which demonstrated that, indeed, the AML1/ETO protein bound to the complex in vivo.

Figure 4:
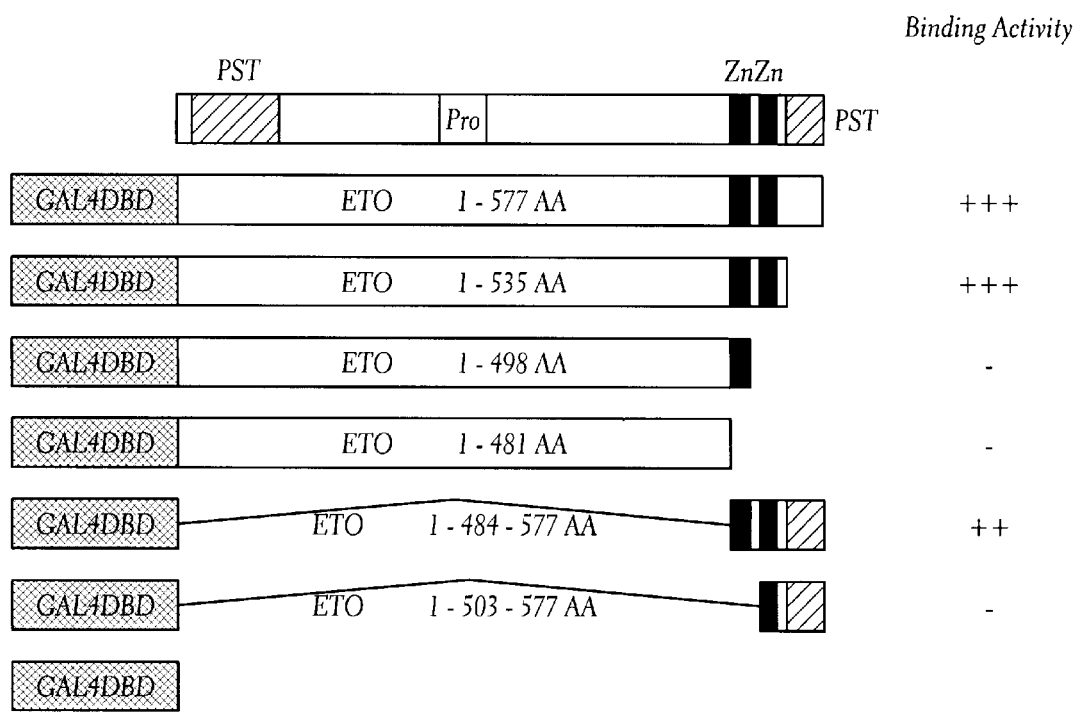
FIG. 4 To determine the HuN-CoR binding domain of ETO, a series of ETO truncation mutants were constructed and inserted into the pGBT9 vector. Yeast cells were co-transformed with the B2 plasmid and the ETO truncation mutants. β-galactosidase assays were used to test for binding activity in vivo (scored from A–≅to A+++≅). The structure of the ETO protein is shown in the schematic, with the proline/serine/threonine (PST)- and proline (Pro)-rich domains, as well as the two zinc finger motifs (Zn), indicated. Deletion of either one of the two zinc finger motifs in the ETO protein abrogated binding to the HuN-CoR, thus localizing a binding domain to these motifs.

To define the region of ETO that interacted with the HuN-CoR, a series of ETO truncation mutants were constructed and inserted into the pGBT9 vector. (FIG. 4). By yeast two-hybrid assays, it was determined that deletion of either zinc finger, located at the carboxy-terminus of the ETO protein, abrogated binding to the HuN-CoR. These results demonstrated that the HuN-CoR binding domain localized to the zinc finger motifs. The cysteine-histidine sequences within ETO=s zinc fingers are unusual and do not match those of previously-defined DNA-binding zinc fingers. (Evans, R. M. and S. M. Hollenberg, Cell 52: 1–3 (1988)). This Cys-His region is highly conserved, however, between ETO and its Drosophila homolog, the homeotic target gene nervy (Feinstein et al., Genetics 140: 573–586 (1995)), another Drosophila protein called DEAF-1 (Deformed epidermal autoregulatory factor-1) (Gross, C. T. and W. McGinnis, EMBO J. 15: 1961–1970 (1996)), and a gene involved in apoptosis known as RP-8 (Owens et al., Mol. Cell. Biol. 11: 4177–4188 (1991)).

Figure 5A:
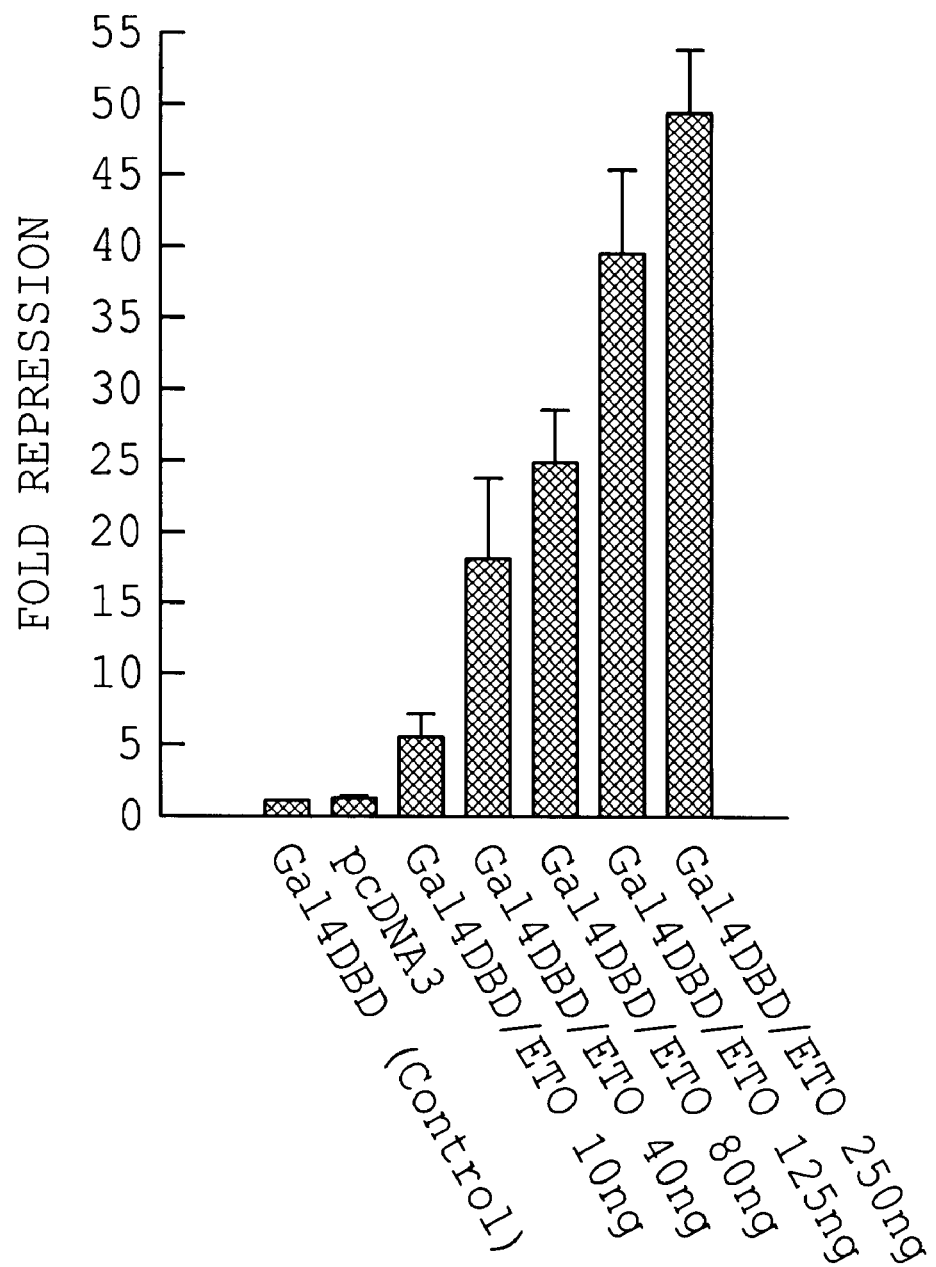
FIG. 5 In the mammalian expression plasmid GAL4 DBD/ETO, ETO is fused with the GAL4 DBD (amino acids 1–147). The firefly luciferase reporter gene is driven by the TK promoter with four copies of the GAL4 DNA binding site upstream. (A) ETO exhibited potent, dose-dependent, transcriptional repression. (B) GAL4 DBD alone partially relieved repression by GAL4 DBD/ETO, due to competition for GAL4 binding sites. When AML1/ETO or RAR∀ LBD, both driven by the CMV promoter, were cotransfected with GAL4 DBD/ETO, the repressive effects of ETO were almost completely abrogated. The AML1/ETO fusion and RAR∀ LBD may compete with ETO for HuN-CoR binding, leading to relief of repression.
Figure 5B:
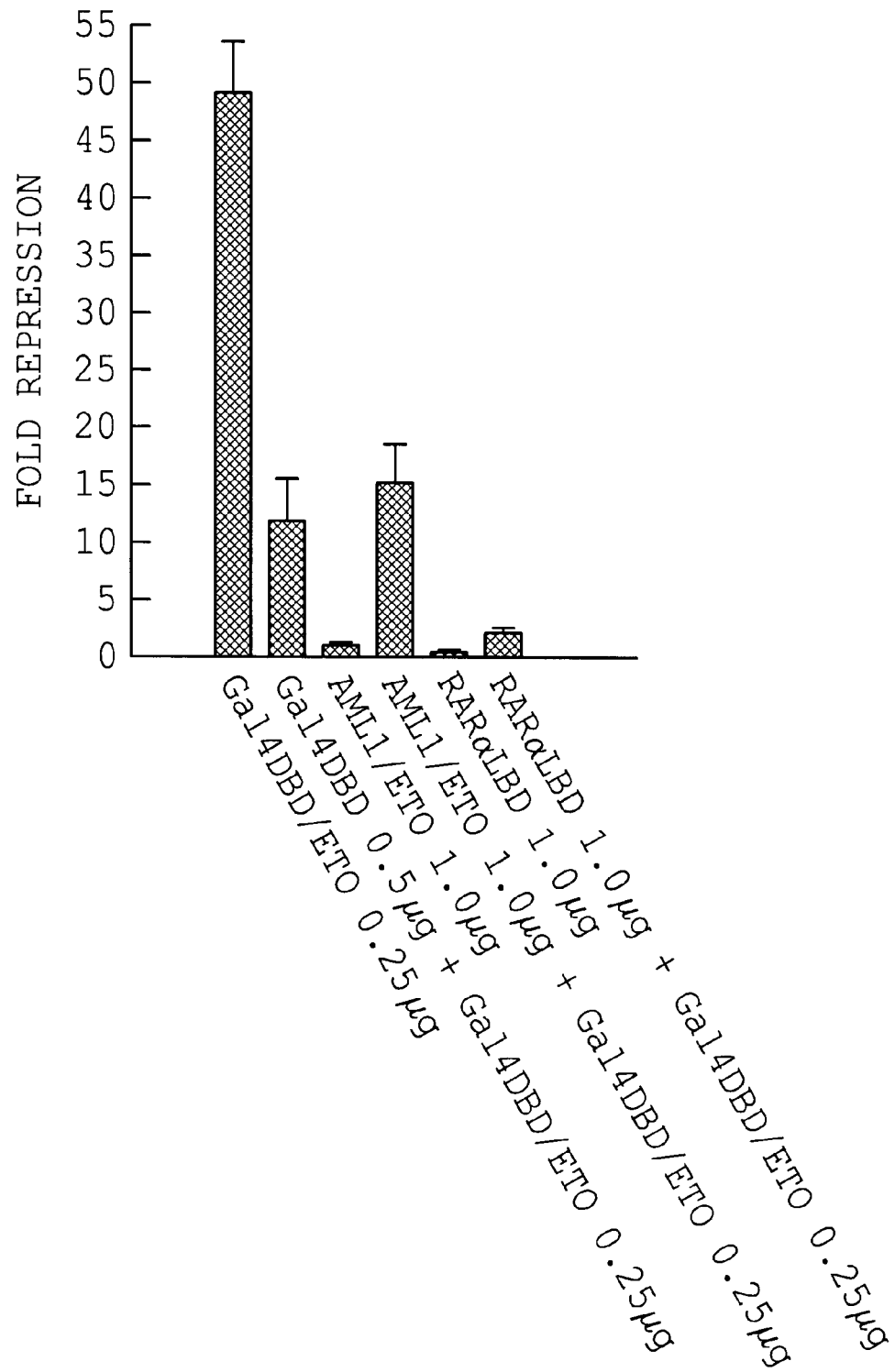

To determine the effects of ETO on regulation of transcription, the GAL4 DBD/ETO fusion was inserted into a mammalian expression vector. This vector was co-transfected with a luciferase reporter gene plasmid in which four copies of the GAL4 DNA binding site have been placed upstream of the reporter gene=s TK promoter. Through the GAL4 DBD, the ETO protein can be recruited to the regulatory region of the reporter gene. In this assay system, ETO exhibited a potent, dose-dependent transcriptional repression. (FIG. 5A). Co-transfection of a vector expressing the AML1/ETO fusion abrogated transcriptional repression by the GAL4 DBD/ETO fusion. (FIG. 5B).

The retinoic acid receptor-α (RARα) LBD is known to interact with the murine N-CoR via the NRI and NRuII domains (Horlein et al., *Nature* 377: 397–403 (1995); Kurokawa et al., *Nature* 377: 451–454 (1995)). It was reasoned that the RARα LBD also competes with the GAL4 DBD/ETO fusion for binding to the endogenous HuN-CoR complex. Consistent with this belief, repression by the GAL4 DBD/ETO fusion was almost completely blocked by co-transfection and addition of the RARα LBD (FIG. 5B). Although the ETO-binding site of the HuN-CoR does not overlap NRI and NRII, the RARα LBD/HuN-CoR complex can deplete HuN-CoR molecules, making them unavailable for binding to ETO.

The AML1/ETO chimeric fusion blocks trans-activation of AML1-responsive hematopoietic target genes. Downstream targets of AML1 include such important genes as those encoding myeloperoxidase, neutrophil elastase, interleukin-3 and granulocyte macrophage-colony stimulating factor (Meyers et al., *Mol. Cell. Biol.* 15: 1974–1982 (1995); Frank et al., *Oncogene* 11: 2667–2674 (1995)). The fusion also can block trans-activation induced by other members of the AML1 family of transcription factors that all bind the core enhancer sequence via the runt homology domain (Meyers et al., *Oncogene* 13: 303–312 (1996)). Recently, AML1 has been found to interact with the multifunctional transcriptional coactivator p300 (Kitabayashi et al., *EMBO J.* 17: 2994–3004 (1998)). Originally identified as a cellular protein that could bind to the adenovirus-E1a oncoprotein, p300 interacts with a histone acetyltransferase, P/CAF (Yang et al., *Nature* 382: 319–324 (1996)) and itself has acetyltransferase activity (Ogryzko et al., *Cell* 87: 953–959 (1996)), serving to regulate transcription through chromatin remodeling and recruitment of basal transcription factors. Disruption of AML1 function by the AML1/ETO fusion affects both transcription activation and cellular differentiation. It had previously been hypothesized that this functional block resulted from direct competition for AML1 binding sites. However, the experiments described above demonstrate that the HuN-CoR co-repressor complex mediates transcriptional repression by interacting with ETO.

Not wanting to limit the discovery described herein to any specific mechanism and offered only for exemplary purposes, it is believed that HuN-Cor mediates transcriptional repression in AML1/ETO individuals according to the following mechanism. The ETO portion of the AML1/ETO fusion interacts with the co-repressor complex. The AML1/ETO fusion contains only the runt homology domain of AML1 and lacks the carboxy-terminal region of AML1 that interacts with the coactivator p300 (Kitabayashi et al., *EMBO J.* 17: 2994–3004 (1998)). In place of this interaction, the runt DNA-binding domain instead recruits the HuN-CoR/mSin3/HDAC1 complex to the promoter of AML1-responsive target genes, resulting in histone deacetylation and transcriptional repression.

It is believed that a sequence-specific DNA-binding protein can have its function altered by fusion with a protein capable of recruiting the N-CoR/mSin3/histone deacetylase complex is similar to the model suggested for the PLZF-RARα variant of acute promyelocytic leukemia. (Hong et al., *Proc. Natl. Acad. Sci. USA.* 94: 9028–9033 (1997)). PLZF has also been found to interact autonomously with SMRT (as well as N-CoR, mSin3, and HDAC1), and both ETO and PLZF appear to function as transcriptional repressors in a ligand-independent manner. PLZF interacts with SMRT via the so-called POZ (pox viruses and zinc fingers) domain (Hong et al., *Proc. Natl. Acad. Sci. USA.* 94: 9028–9033 (1997)). The experiments described herein reveal that the HuN-CoR binding region of ETO can be mapped to its zinc finger motifs, a region that does not resemble a POZ domain.

The physiologic or developmental function of wild-type ETO in brain and hematopoietic tissues (where ETO is expressed) is unknown. ETO-=s *Drosophila* homolog, nervy, is expressed in segregating neuroblasts during embryogenesis, suggesting a regulatory role in early development (Feinstein et al., *Genetics* 140: 573–586 (1995)). ETO=s structure is typical for a transcription factor, but ETO has not yet been shown to bind DNA. In addition to their other homologies, both ETO and nervy also contain an area of similarity to the *Drosophila* coactivator, TAF110 (TATA-binding protein-associated factor 110). (Erickson et al., *Cancer Res.* 54: 1782–1786 (1994)). In an appropriate context, it is believed that ETO can have gene activation properties.

Many have hypothesized a link between chromatin remodeling and cancer. An AML-associated chromosomal translocation has been described that fuses histone acetyltransferase CBP to the zinc-finger domain of MOZ (monocytic-leukemia zinc-finger), for example. (Borrow et al., *Nature Gen.* 14: 33–41 (1996)). Both the Myc antagonists, Mad and Mxi1 (Heinzel et al., *Nature* 387: 43–48 (1997); Alland et al., *Nature* 387: 49–55 (1997); Laherty et al., *Cell* 89: 349–356 (1997)), and the retinoblastoma protein (Brehm et al., *Nature* 391: 597–601 (1998); Magnaghi-Jaulin et al., *Nature* 391: 601–605 (1998)) induce transcriptional repression through the recruitment of co-repressor factors. The fusion proteins of RARα associated with acute promyelocytic leukemia have also been found to interact with the histone deacetylase complex. (Hong et al., *Proc. Natl. Acad. Sci. USA.* 94: 9028–9033 (1997); Lin et al., *Nature* 391: 811–814 (1998); Grignani et al., *Nature* 391: 815–818 (1998)). The experiments described herein demonstrate that the ETO oncoprotein, as well as the AML1/ETO fusion protein, suppress transcription by recruitment of a multimolecular complex capable of remodeling chromatin into a repressive confirmation This pathway presents itself as a potential target for novel anti-cancer therapies. The next section discloses several software and hardware embodiments, as well as, computational methods that can be used to further characterize the HuN-Cor nucleic acid sequence and the HuN-Cor polypeptide sequence.

Software and Hardware Embodiments

The HuN-Cor nucleic acid sequence and the HuN-Cor protein sequence was entered onto a computer readable medium for recording and manipulation. It will be appreciated by those skilled in the art that a computer readable medium having the HuN-Cor nucleic acid sequence or the HuN-Cor protein sequence or both is useful for the determination of homologous sequences, structural and functional domains, and the construction of protein models for rational drug design. The functionality of a computer readable medium having the HuN-Cor nucleic acid sequence or the HuN-Cor protein sequence or both includes the ability to compare the sequence, using computer programs known in the art, so as to perform homology searches, ascertain structural and functional domains, develop protein models and conduct rational drug design.

The HuN-Cor nucleic acid sequence or the HuN-Cor protein sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on computer readable medium to generate manufactures comprising the nucleotide or polypeptide sequence information of this embodiment.

A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments also include systems, particularly computer-based systems that contain the sequence information described herein. The term "a computer-based system" refers to the hardware, software, and any database used to analyze the HUN-Cor nucleic acid sequence or the HuN-Cor protein sequence or both, or fragments of these biomolecules that comprise sequence not found in N-Cor or the nucleic acid encoding N-Cor. The computer-based system preferably includes the storage media described above, and a processor for accessing and manipulating the sequence data. The hardware of the computer-based systems of this embodiment comprise a central processing unit (CPU) and a data database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device may represent, for example, a floppy disk drive, a compact disk drive, a magnetic tape drive, etc. A removable storage medium, such as a floppy disk, a compact disk, a magnetic tape, etc. containing control logic and/or data recorded therein (e.g., the HuN-Cor nucleic acid sequence or the HuN-Cor protein sequence or both) can be inserted into the removable storage device. The computer system includes appropriate software for reading the control logic and/or the data from the removable medium storage device once inserted in the removable medium storage device.

The HuN-Cor nucleic acid sequence or the HuN-Cor protein sequence or both can be stored in a well known manner in the main memory, any of the secondary storage devices, and/or a removable storage medium. Software for accessing and processing the HuN-Cor nucleic acid sequence or the HuN-Cor protein sequence or both (such as search tools, compare tools, and modeling tools etc.) reside in main memory during execution.

As used herein, "a database" refers to memory that can store nucleotide or polypeptide sequence information, protein model information, and information on other peptides, chemicals, peptidomimetics, and other agents that interact with proteins. Additionally, a "database" refers to a memory access component that can access manufactures having recorded thereon nucleotide or polypeptide sequence information, protein model information and information on other peptides, chemicals, peptidomimetics, and other agents that interact with proteins. In some embodiments, a database stores a HuN-Cor disease-state profile comprising concentrations or expression levels or concentration ranges or expression level ranges of HuN-Cor or HuN-Cor or both detected in biological samples from different subjects (e.g., subjects with and without a disease related to HuN-Cor). In other embodiments, a database stores a HuN-Cor diseasestate profile comprising concentration ranges or levels of HuN-Cor detected in biological samples obtained from various tissue or fluid sources from diseased and healthy subjects. Such databases can store this information as ratios that compare the expression levels of HuN-Cor or HuN-Cor from the various tissue or fluid sources, for example. Many databases are known to those of skill in the art and several will be discussed infra.

The sequence data on HuN-Cor or HuN-Cor or both can be stored and manipulated in a variety of data processor programs in a variety of formats. For example, the sequence data can be stored as text in a word processing file, such as MicrosoftWORD or WORDPERFECT, an ASCII file, a html file, or a pdf file in a variety of database programs familiar to those of skill in the art, such as DB2, SYBASE, or ORACLE.

A "search program" refers to one or more programs that are implemented on the computer-based system to compare a nucleotide or polypeptide sequence with other nucleotide or polypeptide sequences and agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. A search program is used, for example, to compare regions of the HuN-Cor nucleic acid sequence or the HuN-Cor protein sequence or both that match sequences in nucleic acid and protein data bases so as to identify homologies and structural or functional motifs. Further, a search program is used to compare an unknown nucleic acid or protein sequence with the HuN-Cor nucleic acid sequence or the HuN-Cor protein sequence so as to identify homologies and related structural or functional domains. Additionally, a search program is used to compare a HuN-Cor-disease state profile from a tested subject to HuN-Cor-disease state profiles from diseased and healthy subjects present in a database.

A "retrieval program" refers to one or more programs that are implemented on the computer based system to identify a homologous nucleic acid sequence, a homologous protein sequence, or a homologous protein model. A retrieval program is also used to identify peptides, peptidomimetics and chemicals that interact with a nucleic acid sequence, a protein sequence, or a protein model stored in a database. Further a retrieval program is used to identify a disease state of an individual by obtaining a HuN-Cor disease-state profile from the database that matches the HuN-Cor-disease state profile from the tested subject. The discussion below describes embodiments that have a nucleic acid that encodes HuN-Cor or a fragment thereof Use of Nucleic Acids Encoding HuN-Cor or Fragments Thereof The cDNA sequence encoding HuN-Cor is provided in the sequence listing (SEQ. ID NO.: 1). The cDNA sequence encoding N-Cor is provided in the sequence listing (SEQ. ID NO.: 2). Full-length HuN-Cor and fragments of HuN-Cor that comprise a nucleotide sequence not present in N-Cor are embodiments. Further, embodiments include nucleic acids that complement full-length HuN-Cor and nucleic acids that complement fragments of HuN-Cor that comprise a nucleotide sequence not present in N-Cor. By comparing the nucleic acid sequences provided in SEQ. ID NOS.: 1 and 2, one of skill in the art can determine fragments of HuN-Cor that comprise nucleotide sequence not present in N-Cor. Further, nucleic acids that complement fragments of HuN-Cor that comprise sequence not present in N-Cor can be determined by comparing the nucleic acid sequences in SEQ. ID NOS.: 1 and 2.

Fragments of HuN-Cor and nucleic acids that complement HuN-Cor that contain a nucleotide sequence not present in N-Cor and their functional equivalents are desirably at least six nucleotides in length may be as much as 7,939 nucleotides in length. For example, the nucleic acid embodiments can have less than 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47,48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 828, 900, 1000, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6250, 6500, 6750, 7000, 7250, 7500, 7750, and 7939 consecutive nucleotides of a HuN-Cor cDNA sequence.

Desirably, however, the nucleic acid embodiments comprise at least 9, 12, 13, 14, 15, 16, 17, 18, or 19 consecutive nucleotides from Hue-Cor or a nucleic acid that complements HuN-Cor, as conditions dictate. More desirably, the nucleic acid embodiments comprise at least 20–30 consecutive nucleotides from HuN-Cor or a nucleic acid that complements HuN-Cor. In some cases, the nucleic acid embodiments comprise more than 30 nucleotides from the nucleic acids encoding HuN-Cor or a nucleic acid that complements HuN-Cor and in other cases, the nucleic acid embodiments comprise at least 40, at least 50, at least 75, at least 100, at least 150, or at least 200 consecutive nucleotides from the nucleic acids encoding HuN-Cor or a nucleic acid that complements HuN-Cor. Some preferred nucleic acid embodiments have a nucleic acid sequence that corresponds to a region of HuN-Cor, which interacts with members of a transcriptional repressor complex. The nucleic acid oligomers described above have biotechnological and diagnostic use, e.g., in nucleotide acid hybridization assays, Southern and Northern Blot analysis, etc. and the prognosis of HuN-Cor-related diseases. (See Example 3). Further, these embodiments can be used to treat and/or prevent HuN-Cor-related diseases (e.g., cancers such as leukemia). (See Example 2).

Some embodiments comprise recombinant nucleic acids having all or part of the HuN-Cor gene or recombinant nucleic acids that complement all or part of HuN-Cor. Desired embodiments comprise full-length HuN-Cor and fragments of HuN-Cor that comprise a nucleotide sequence not found in N-Cor and nucleic acids that complement full-length HuN-Cor and fragments of HuN-Cor that comprise a nucleotide sequence not found in N-Cor. A recombinant construct can be capable of replicating autonomously in a host cell. Alternatively, the recombinant construct can become integrated into the chromosomal DNA of the host cell. Such a recombinant polynucleotide comprises a polynucleotide of genomic or cDNA, of semi-synthetic or synthetic origin by virtue of human manipulation. Therefore, recombinant nucleic acids comprising sequences otherwise not naturally occurring are provided by the embodiments described herein. Although nucleic acids encoding HuN-Cor or nucleic acids having sequences that complement HuN-Cor as they appear in nature can be employed, they will often be altered, e.g., by deletion, substitution, or insertion and will be accompanied by sequence not present in humans.

The nucleic acid embodiments can also be altered by mutation such as substitutions, additions, or deletions that provide for sequences encoding functionally equivalent molecules. Due to the degeneracy of nucleotide coding sequences, other DNA sequences that encode substantially the same HuN-Cor amino acid sequence as depicted in SEQ. ID NO.: 3 can be used in some embodiments. These include, but are not limited to, nucleic acid sequences comprising all or portions of HuN-Cor or nucleic acids that complement all or part of HuN-Cor that have been altered by the substitution of different codons that encode a functionally equivalent amino acid residue within the sequence, thus producing a silent change.

In addition, recombinant HuN-Cor-encoding nucleic acid sequences and their complementary sequences can be engineered so as to modify processing or expression of HuN-Cor. For example, and not by way of limitation, the HuN-Cor gene can be combined with a promoter sequence and/or ribosome binding site, or a signal sequence may be inserted upstream of HuN-Cor-encoding sequences to permit secretion of HuN-Cor and thereby facilitate harvesting or bioavailability. Additionally, a given HuN-Cor nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis. (Hutchinson et al., J. Biol. Chem. 253:6551 (1978)). Further, nucleic acids encoding other proteins or domains of other proteins can be joined to nucleic acids encoding HuN-Cor so as to create a fusion protein. In preferred embodiments, HuN-Cor or portions of HuN-Cor are joined to nucleic acids encoding DNA binding proteins (e.g., AML1/CBF, MyoD, POU, GATA, and homeobox proteins). The resulting fusion proteins are used as biotechnological tools or pharmaceuticals or both, as will be discussed below.

The nucleic acid embodiments can also be used as biotechnological tools for isolation procedures and diagnostic assays. By using the HuN-Cor nucleic acid sequence disclosed in the sequence listing (SEQ ID NO.: 1), probes that complement HuN-Cor can be designed and manufactured by oligonucleotide synthesis. These probes can be disposed on a support (e.g., a gene chip) and used to detect the presence/absence and amounts of HuN-Cor nucleic acids in a biological sample. Example 3, provides one diagnostic approach that uses the nucleic acid embodiments in a gene chip array to detect the presence of HuN-Cor nucleic acids in a sample. The probes described above can also be used to screen cDNA or genomic libraries so as to isolate natural sources of the nucleic acid embodiments. Additionally, these probes can be used to isolate other nucleotide sequences capable of hybridizing to them.

Further, sequences from nucleic acids complementing HuN-Cor, or portions thereof can be used to make oligonucleotide primers by conventional oligonucleotide synthesis for use in isolation and diagnostic procedures. These oligonucleotide primers can be used, for example, to isolate the nucleic acid embodiments of this invention by amplifying the sequences resident in genomic DNA or other natural sources by using the Polymerase Chain Reaction (PCR) or other nucleic acid amplification techniques. Further, the nucleic acid embodiments can be used to modulate transcriptional repression (e.g., by upregulating or downregulating the expression of HuN-Cor) and, therefore, have several uses in addition to biotechnological research including therapeutic and prophylactic applications. The design and manufacture of pharmaceuticals that have a nucleic acid embodiments are within the scope of some aspects of the invention. Some of these pharmaceuticals are used to treat or prevent cancer (e.g., leukemia) and Example 2 describes experiments that verified that nucleic acids encoding regions of HuN-Cor can be used to induce differentiation of leukemia cells. Alternatively, the nucleic acids encoding HuN-Cor or fragments thereof are manipulated using conventional techniques in molecular biology to create recombinant constructs that express HuN-Cor or fragments of HuN-Cor. The discussion that follows describes several expression constructs and protein embodiments in greater detail.

HuN-Cor Polypeptides and Their Expression

HuN-Cor polypeptides or derivatives thereof, include but are not limited to, those containing as a primary amino acid sequence all of the amino acid sequence substantially as depicted in the sequence listing (SEQ. ID NO.: 3) and fragments of SEQ. ID. NO.: 3 at least three amino acids in length that comprise amino acid sequence not found in N-Cor, including altered sequences in which functionally equivalent amino acid residues are substituted for residues within the sequence resulting in a silent change. The amino acid sequence of N-Cor is provided in SEQ. ID NO.: 4 and by comparing SEQ. ID NOS.: 3 and 4, one of skill in the art can determine fragments of HuN-Cor that comprise an amino acid sequence not found in N-Cor. Accordingly, one or more amino acid residues within the HuN-Cor polypeptide of SEQ ID. NO.: 3 and fragments of SEQ. ID. NO.: 3 that comprise an amino acid sequence not found in N-Cor can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

Some HuN-Cor fragment embodiments have less than 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49,50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, 1300, 1400, 1500, 1600, 1700, 1800, 1900, 2000, 2100, 2200, 2300, 2400, and 2439 consecutive amino acids of HuN-Cor. In other embodiments, the HuN-Cor polypeptide of SEQ ID. NO.: 3 and fragments of SEQ. ID. NO.: 3 that comprise an amino acid sequence not found in N-Cor, or derivatives thereof are differentially modified during or after translation, e.g., by phosphorylation, glycosylation, cross-linking, acylation, proteolytic cleavage, linkage to an antibody molecule, membrane molecule, or other ligand. (Ferguson et al., Ann. Rev. Biochem. 57:285–320 (1988)). Preferred HuN-Cor fragments include a region of HuN-Cor that is involved in the assembly or stability of a transcription repressor complex. For example, a preferred polypeptide embodiment includes amino acid residues 988–1816 and/or amino acid residues 1551–1803 of HuN-Cor.

In several embodiments, the HuN-Cor polypeptide of SEQ ID. NO.: 3 and fragments of SEQ. ID. NO.: 3 that comprise an amino acid sequence not found in N-Cor are expressed in a cell line. Additional embodiments include isolated or purified HuN-Cor and fragments of HuN-Cor that comprise an amino acid sequence not found in N-Cor. The term "isolated" requires that the material be removed from its original environment (e.g., the natural environment if it is naturally occurring). For example, a naturally occurring nucleic acid or protein present in a living cell is not isolated, but the same nucleic acid or protein, separated from some or all of the coexisting materials in the natural system, is isolated. In accordance with this definition, HuN-Cor nucleic acid or HuN-Cor protein or nucleic acid or polypeptide fragments present in a cell lysate are "isolated", The term "purified" does not require absolute purity; rather it is intended as a relative definition. For example, recombinant nucleic acids and proteins are routinely purified to electrophoretic homogeneity, as detected by ethidum bromide staining or Coomassie staining, and are suitable in several assays despite having the presence of contaminants.

To express the proteins encoded by HuN-Cor or portions thereof, nucleic acids containing the coding sequence for HuN-Cor or fragments of HuN-Cor that comprise an amino acid sequence not found in N-Cor are obtained and cloned into a suitable expression vector such that the coding region is operably linked to a heterologous promoter. The nucleic acid encoding the protein or polypeptide to be expressed is operably linked to a promoter in an expression vector using conventional cloning technology. The expression vector can be in any of the mammalian, yeast, amphibian, insect, parasite, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767. Further, a secretory leader sequence can be incorporated so as to facilitate purification of the protein.

The following is provided as one exemplary method to express the proteins encoded by the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for PstI incorporated into the 5'primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII. The ligated product is transfected into a suitable cell line, e.g., mouse NIH 3T3 cells, using Lipofectin (Life Technologies, Inc., Grand Island, N.Y.) under conditions outlined in the product specification. Positive transfectants are selected after growing the transfected cells in 600 µg/ml G418 (Sigma, St. Louis, Mo.). Preferably the expressed protein is released into the culture medium, thereby facilitating purification.

Alternatively, nucleic acids encoding HuN-Cor and fragments of HuN-Cor that comprise a nucleotide sequence not found in N-Cor can be cloned into pED6dpc2 and the resulting pED6dpc2 constructs can be transfected into a host cell, such as COS 1 cells. Methotrexate resistant cells are selected and expanded. Preferably, the protein expressed is released into the culture medium thereby facilitating purification.

Another embodiment utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide that has a high affinity for divalent cations. Using a nickel-chelating resin (Invitrogen), the recombinant protein can be purified in one step and the leader can be subsequently removed by cleavage with enterokinase.

One preferred vector for the expression of HuN-Cor and fragments of HuN-Cor that comprise an amino acid sequence not found in N-Cor is the pBlueBacHis2 Xpress. The pBlueBacHis2 Xpress vector is a Baculovirus expression vector containing a multiple cloning site, an ampicillin resistance gene, and a lac z gene. By one approach, the HuN-Cor nucleic acid, or portion thereof is cloned into the pBlueBacHis2 Xpress vector and SF9 cells are infected. The expression protein is then isolated or purified according to the manufacturer's instructions. Several other cultured cell lines having recombinant constructs or vectors comprising HuN-Cor or portions thereof are embodiments and their manufacture would be routine given the present disclosure.

Proteins in the culture medium can also be separated by gel electrophoresis. The separated proteins are then detected using techniques such as Coomassie or silver staining or by using antibodies against the protein. Coomassie, silver staining, and immunolabeling of proteins are techniques familiar to those skilled in the art. If desired, the proteins can also be ammonium sulfate precipitated or separated based on size or charge prior to electrophoresis.

The protein encoded by HuN-Cor or portion thereof can also be purified using standard immunochromatography techniques. In such procedures, a solution containing the protein, such as the culture medium or a cell extract, is applied to a column having antibodies against the protein attached to the chromatography matrix. The protein is allowed to bind the immunochromatography column. Thereafter, the column is washed to remove non-specifically bound proteins. The specifically bound protein is then released from the column and recovered using standard techniques.

If antibody production is not possible, Hun-Cor or portion thereof can be incorporated into expression vectors designed for use in purification schemes employing chimeric polypeptides. In such strategies, the coding sequence of Hun-Cor or portion thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites can be engineered between the β-globin gene or the nickel binding polypeptide and the Hun-Cor cDNA such as enterokinase. Thus, the two polypeptides of the chimera can be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biology*, L. G. Davis, M. D. Dibner, and J. F. Battey, ed., Elsevier Press, N.Y., 1986) and many of the methods are available from Stratagene, Life Technologies, Inc., or Promega. HuN-Cor polypeptides may additionally be produced from the construct using in vitro translation systems, such as the In vitro Express™ Translation Kit (Stratagene).

In addition to isolating or purifying HuN-Cor and fragments of HuN-Cor that comprise an amino acid sequence not found in N-Cor by using recombinant DNA techniques, HuN-Cor and fragments of HuN-Cor that comprise an amino acid sequence not found in N-Cor can be prepared by chemical synthesis methods (such as solid phase peptide synthesis) using methods known in the art such as those set forth by Merrifield et al., J. Am. Chem. Soc. 85:2149 (1964), Houghten et al., Proc. Natl. Acad. Sci. USA, 82:51:32 (1985), and Stewart and Young (solid phase peptide synthesis, Pierce Chem Co., Rockford, Ill. (1984). Such polypeptides can be synthesized with or without a methionine on the amino terminus. Chemically synthesized HuN-Cor and fragments of HuN-Cor that comprise an amino acid sequence not found in N-Cor can be oxidized using methods set forth in these references to form disulfide bridges. HuN-Cor and fragments of HuN-Cor that comprise an amino acid sequence not found in N-Cor can be employed as biologically active or immunological substitutes for natural, purified HuN-Cor and fragments of HuN-Cor that comprise an amino acid sequence not found in N-Cor.

Following synthesis or expression and isolation or purification of the proteins encoded by HuN-Cor or a portion thereof, the isolated or purified proteins can be used to generate antibodies and tools for identifying agents that interact with HuN-Cor and fragments of HuN-Cor that comprise an amino acid sequence not found in N-Cor. Antibodies that recognize HuN-Cor and fragments of HuN-Cor that comprise an amino acid sequence not found in N-Cor have many uses including, but not limited to, biotechnological applications, therapeutic/prophylactic applications, and diagnostic applications. Such antibodies include, but are not limited to, polyclonal, monoclonal, chimeric, single chain, Fab fragments and fragments produced by a Fab expression library. Neutralizing antibodies, i.e., those that inhibit formation of a transcriptional repressor complex, are especially preferred for diagnostics and therapeutics.

For the production of antibodies, various hosts including goats, rabbits, rats, mice, etc may be immunized by injection with HuN-Cor or any portion, fragment or oligopeptide that retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum* are potentially useful adjuvants.

Peptides used to induce specific antibodies can have an amino acid sequence consisting of at least five amino acids, preferably at least 10 or 15 amino acids. Desirably, short stretches of amino acids encoding fragments of HuN-Cor are fused with those of another protein such as keyhole limpet hemocyanin and antibody is produced against the chimeric molecule. While antibodies capable of specifically recognizing HuN-Cor can be generated by injecting into mice synthetic 5-mer, 10-mer, and 15-mer peptides that corresponds to a protein sequence of HuN-Cor, a more diverse set of antibodies can be generated by using recombinant or purified HuN-Cor and fragments of HuN-Cor that comprise an amino acid sequence not found in N-Cor.

To generate antibodies to HuN-Cor and fragments of HuN-Cor that comprise an amino acid sequence not found in N-Cor, substantially pure HuN-Cor or a fragment of HuN-Cor that comprises amino acids not found in N-Cor is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to HuN-Cor or a fragment of HuN-Cor, desirably fragments of HuN-Cor that comprise an amino acid sequence not found in N-Cor, can be prepared using any technique that provides for the production of antibody molecules by continuous cell lines in culture. These include but are not limited to the hybridoma technique originally described by Koehler and Milstein (Nature 256:495–497 (1975), the human B-cell hybridoma technique (Kosbor et al. Immunol Today 4:72 (1983); Cote et al Proc Natl Acad Sci 80:2026–2030 (1983), and the EBV-hybridoma technique Cole et al. Monoclonal Antibodies and Cancer Therapy, Alan R. Liss Inc, New York N.Y., pp 77–96 (1985). In addition, techniques developed for the production of "chimeric antibodies", the splicing of mouse antibody genes to human antibody genes to obtain a molecule with appropriate antigen specificity and biological activity can be used. (Morrison et al. Proc Natl Acad Sci 81:6851–6855 (1984); Neuberger et al. Nature 312:604–608(1984); Takeda et al. Nature 314:452–454(1985). Alternatively, techniques described for the production of single chain antibodies (U.S. Pat. No. 4,946,778) can be adapted to produce HuN-Cor-specific single chain antibodies. Antibodies can also be produced by inducing in vivo production in the lymphocyte population or by screening recombinant immunoglobulin libraries or panels of highly specific binding reagents as disclosed in Orlandi et al., Proc Natl Acad Sci 86: 3833–3837 (1989), and Winter G. and Milstein C; Nature 349:293–299 (1991).

Antibody fragments that contain specific binding sites for HuN-Cor can also be generated. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity Huse W. D. et al. Science 256:1275–1281.(1989).

By one approach, monoclonal antibodies to HuN-Cor of fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21–2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunologic* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980).

Antibody preparations prepared according to either protocol are useful in quantitative immunoassays that determine concentrations of antigen-bearing substances in biological samples; they are also used semiquantitatively or qualitatively (e.g., in diagnostic embodiments that identify the presence of HuN-Cor in biological samples). Additionally, HuN-Cor and fragments of HuN-Cor that comprise an amino acid sequence not found in N-Cor, can be used to induce antibody production in humans. That is, HuN-Cor and fragments of HuN-Cor that comprise an amino acid sequence not found in N-Cor whether made chemically or as detailed above, can be used as an antigen or vaccine so as to elicit an immune response in a subject. The next section describes the use of agents comprising nucleic acids encoding HuN-Cor (HuN-Cor) and polypeptides corresponding to HuN-Cor or fragments thereof to modulate transcriptional repression.

Modulation of HuN-Cor-dependent Transcriptional Repression

The experiments described above demonstrate that HuN-Cor efficiently associates with other proteins including ETO, AML1/ETO, HDAC1, and Sin3 to form transcriptional repressor complexes. From this discovery, it is clear that HuN-Cor is involved in the assembly of many different transcriptional repressor complexes. For this reason, the term "transcriptional repressor complex" is intended to refer to any complex having HuN-Cor that is involved in the repression of transcription. In some embodiments, nucleic acids encoding HuN-Cor, nucleic acids complementary to HuN-Cor, and polypeptide fragments of HuN-Cor proteins are used to inhibit the formation of a transcriptional repressor complex. In other embodiments, nucleic acids encoding HuN-Cor are used to enhance transcriptional repression. Accordingly, these embodiments are used to modulate (enhance or inhibit) transcriptional repression. (See Example 2). In preferred embodiments fusion proteins comprising a DNA binding domain joined to HuN-Cor or a polypeptide fragment of HuN-Cor are used to modulate transcriptional repression of a specific gene.

Several embodiments are provided that inhibit the association of HuN-Cor in a transcriptional repressor complex ("HuN-Cor inhibitory agents") in a cell and, thus, reduce HuN-Cor-dependent transcriptional repression. One embodiment of an HuN-Cor inhibitory agent, for example, is an antisense oligonucleotide or ribozyme that hybridizes to nucleic acid encoding various regions of HuN-Cor. By "antisense oligonucleotide" is meant a nucleic acid or modified nucleic acid including, but not limited to DNA, RNA, modified DNA or RNA (including branched chain nucleic acids and 2' O-methyl RNA) and PNA (polyamide nucleic acid).

Several ribozymes are known to those of skill in the art can also be easily designed to hybridize to nucleic acid sequence encoding HuN-Cor and thereby inhibit the production of functional protein. Desirably, antisense oligonucleotides or ribozymes that hybridize to the start codon of HuN-Cor are used. In one embodiment, full length antisense HuN-Cor is used to significantly reduced HuN-Cor-dependent transcriptional repression. Many other antisense oligonucleotides or ribozymes that interfere with the formation of a complex comprising HuN-Cor can be designed and screened by the methods detailed previously.

The antisense nucleic acids should have a length and melting temperature sufficient to permit formation of an intracellular duplex having sufficient stability to inhibit the expression of the MnRNA in the duplex. Strategies for designing antisense nucleic acids suitable for use in gene therapy are disclosed in Green et al., *Ann. Rev. Biochem.*, 55:569–597 (1986) and Izant and Weintraub, *Cell*, 36:1007–1015 (1984). In some strategies, antisense molecules are obtained from a nucleotide sequence encoding HuN-Cor by reversing the orientation of the coding region with respect to a promoter so as to transcribe the opposite strand from that which is normally transcribed in the cell. Antisense molecules and ribozymes can be prepared by any method known in the art for the synthesis of RNA molecules. These include techniques for chemically synthesizing oligonucleotides such as solid phase phosphoramidite chemical synthesis.

Alternatively, RNA molecules can be generated by in vitro and in vivo transcription of DNA sequences encoding HuN-Cor. Such DNA sequences can be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues. Further, oligonucleotides that are complementary to the mRNA encoding HuN-Cor can be synthesized in vitro. Thus, antisense nucleic acids are capable of hybridizing to the HuN-Cor mRNA to create a duplex. In some embodiments, the antisense sequences can contain modified sugar phosphate backbones to increase stability and make them less sensitive to RNase activity. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine that are not as easily recognized by endogenous endonucleases. Further examples are described by Rossi et al., *Pharmacol. Ther.*, 50(2):245–254, (1991).

Various types of antisense oligonucleotides complementary to the HuN-Cor mRNA can be used. In one preferred embodiment, stable and semi-stable antisense oligonucleotides described in International Application No. PCT WO94/23026 are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides. In another preferred embodiment, the antisense oligodeoxynucleotides described in International Application No. WO 95/04141 are used. In yet another preferred embodiment, the covalently cross-linked antisense oligonucleotides described in International Application No. WO 96/31523 are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522 can also be used. These molecules are stable to degradation and contain at least one transcription control recognition sequence that binds to control proteins and are effective as decoys therefor. These molecules can contain "hairpin" structures, "dumbbell" structures, "modified dumbbell" structures, "cross-linked" decoy structures and "loop" structures. In another preferred embodiment, the cyclic double-stranded oligonucleotides described in European Pat. Application No. 0572 287 A2 are used. These ligated oligonucleotide "dumbbells" contain the binding site for a transcription factor and inhibit expression of the gene under control of the transcription factor by sequestering the factor. Use of the closed antisense oligonucleotides disclosed in International Application No. WO 92/19732 are also contemplated. Because these molecules have no free ends, they are more resistant to degradation by exonucleases than are conventional oligonucleotides. These oligonucleotides can be multifunctional, interacting with several regions that are not adjacent to the target mRNA.

The appropriate level of antisense nucleic acids required to inhibit gene expression can be determined using in vitro expression analysis. The antisense molecule can be introduced into the cells expressing HuN-Cor by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector can be any of a variety of expression vectors known in the art, including retroviral or viral vectors, vectors capable of extrachromosomal replication, or integrating vectors. The vectors can be DNA or RNA.

The antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher can be possible after testing the toxicity of the oligonucleotide in laboratory animals. It is additionally contemplated that cells from a vertebrate, such as a mammal or human, are removed, treated with the antisense oligonucleotide, and reintroduced into the vertebrate.

Ribozymes can also be used to reduce or eliminate HuN-Cor expression. Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of aspects of the invention, are engineered hammerhead motif ribozyme molecules that can specifically and efficiently catalyze endonucleolytic cleavage of a sequence encoding HuN-Cor, for example. Specific ribozyme cleavage sites within any potential RNA target are initially identified by scanning the target molecule for ribozyme cleavage sites that include the following sequences, GUA, GUU and GUC. Once identified, short RNA sequences of between 15 and 20 ribonucleotides corresponding to the region of the target gene containing the cleavage site can be evaluated for secondary structural features that may render the oligonucleotide inoperable. The suitability of candidate targets can also be evaluated by testing accessibility to hybridization with complementary oligonucleotides using ribonuclease protection assays. Delivery of antisense and ribozyme agents by transfection and by liposome are quite well known in the art.

Another embodiment of an HuN-Cor inhibitory agent suitable for liposome mediated transfer is a polypeptide that interferes with the association of a transcriptional repressor complex comprising HuN-Cor or a nucleic acid encoding such a polypeptide. One such polypeptide comprises a sequence of ETO that interacts with HuN-Cor (e.g., a zinc finger domain of ETO, or homolog, derivative, or fragment thereof). (See Example 2). Polypeptide fragments that inhibit the association of HuN-Cor or the association of HuN-Cor with an interacting protein such as ETO, AML1/ETO, HDAC1, and Sin3 can be rapidly engineered and identified given the present disclosure. The screening of polypeptide fragments and deletion mutant proteins that inhibit the association of a complex having HuN-Cor would be routine given the present disclosure and assays described herein. For example, polypeptide HuN-Cor inhibitory agents can be identified by their ability to disrupt the formation of the transcriptional repressor complex by employing conventional affinity chromatography techniques, sandwich assays, ELISA assays, or other binding assays known to those of skill in the art. Alternatively, a screening method wherein the polypeptide HuN-Cor inhibitory agent is delivered to cells in culture by liposome-mediated transfer and cell lysates are analyzed by immunoprecipitation and Western blot can rapidly evaluate the polypeptide's ability to inhibit the association of a transcriptional repressor complex having HuN-Cor.

In another embodiment, concentrations of HuN-Cor in a cell are raised so as to enhance HuN-Cor-dependent transcriptional repression. There may be many ways to raise the concentration of HuN-Cor in a cell. Liposome-mediated transfer, is one approach to deliver HuN-Cor protein to a cell. Alternatively, the concentration of HuN-Cor can be raised in a cell by transfecting constructs encoding HuN-Cor. A construct for use in the transfection of HuN-Cor into cells in culture was described previously and many others can be developed by those of skill in the art. Retroviral constructs for the delivery of nucleic acid encoding HuN-Cor in a subject are also contemplated and many retroviral vectors that can be engineered to produce HuN-Cor are known. Agents that enhance the association of a transcriptional repressor complex having HuN-Cor, including an agent that raises the concentration of HuN-Cor in a cell, "HuN-Cor enhancing agents", can be rapidly screened for their ability to promote the formation of the complex having HuN-Cor by employing a method wherein the HuN-Cor enhancing agent is delivered to cells in culture by liposome-mediated transfer or transfection and cell lysates are analyzed by immunoprecipitation and Western blot. Other embodiments of HuN-Cor inhibitory or enhancing agents (collectively refered to as "HuN-Cor modulating agents") include antibodies, peptidomimetics, and chemicals that inhibit or enhance HuN-Cor-dependent transcriptional repression. Some embodiments of these HuN-Cor inhibitory agents include antibodies, peptidomimetics, and chemicals that bind to amino acid residues of HuN-Cor that are not present in N-Cor. Regions of HuN-Cor essential for the association of interacting proteins are also desirably blocked by antibodies, peptidomimetics, and chemicals.

Several other methods for identifying agents that modulate the formation of a complex having HuN-Cor and, concomitantly, modulate HuN-Cor-dependent transcription ("HuN-Cor modulating agents") can be used. One embodiment encompasses an in vitro transcription assay comprising natural, synthetic, mutant, recombinant, and/or multimerized derivatives of HuN-Cor. Many in vitro transcription assays are known to those of skill in the art and the inclusion of natural, synthetic, mutant, recombinant, and/or multimerized derivatives of HuN-Cor or a fusion protein comprising HuN-Cor joined to a DNA binding domain in these assays provides a method to quickly analyze transcriptional repression. For example, a reporter gene construct that encodes a detectable transcriptional product and has a transcriptional control element that is responsive to a transcriptional activation complex is used as a template for run-off transcripts generated by nuclear extracts spiked with HuN-Cor in the presence and absence of an HuN-Cor modulating agent. Run-off transcripts are then detected by conventional methods and the influence of the HuN-Cor modulating agent on transcription is determined. In some embodiments, mutant HuN-Cor or a nucleic acid encoding mutant HuN-Cor is delivered to cells as the HuN-Cor modulating agent. Several different HuN-Cor mutants are made and are tested for their ability to repress transcription in the presence and absence of HuN-Cor. Additionally, by employing immunoprecipitation, the ability of the mutant HuN-Cor proteins to form stable transcriptional repressor complexes is also assessed. The mutants identified as forming the most stable complexes are used as HuN-Cor enhancing agents and the mutants identified as forming the most weak transcriptional repressor complexes are used as HuN-Cor inhibiting agents. In this manner, HuN-Cor modulating agents are screened and identified Several methods of molecular modeling, combinatorial chemistry, and rational drug design are described in the next section.

Methods of Rational Drug Design

Combinatorial chemistry is the science of synthesizing and testing compounds for bioactivity en masse, instead of one by one, the aim being to discover drugs and materials more quickly and inexpensively than was formerly possible. In some embodiments, search programs are employed to compare regions of HuN-Cor that modulate transcriptional repression with other molecules, such as peptides, peptidomimetics, and chemicals so that therapeutic interactions of the molecules can be predicted and new derivative molecules can be designed. In other embodiments, search programs are employed to compare regions of molecules that interact with HuN-Cor and, thereby modulate transcriptional repression, with other molecules such as peptides, peptidomimetics, and chemicals, so that therapeutic interactions of the molecules can be predicted and new derivative HuN-Cor modulating agents can be designed. (Schneider, *Genetic Engineering News December*: page 20 (1998), Tempczyk et al., *Molecular Simulations Inc. Solutions* April (1997), and Butenhof, *Molecular Simulations Inc. Case Notes* (August 1998)). This process of directed combinatorial chemistry is referred to as "rational drug design", Libraries of molecules that resemble HuN-Cor or interact with HuN-Cor and, thereby inhibit or enhance the function of HuN-Cor ("modulate" HuN-Cor activity) can be created. In some contexts, the term "HuN-Cor modulating agent" includes HuN-Cor, polypeptide fragments corresponding to HuN-Cor, fusion proteins comprising HuN-Cor or polypeptide fragments of HuN-Cor, nucleic acids encoding these molecules, peptidomimitecs, chemicals, and other molecules that modulate HuN-Cor-dependent transcriptional repression (e.g., ETO and fragments thereof).

One goal of rational drug design is to produce structural analogs of biologically active polypeptides of interest or of small molecules with which they interact (e.g., agonists, antagonists, null compounds) in order to fashion drugs that are, for example, more or less potent forms of the molecule. (See, e.g., Hodgson, *Bio. Technology* 9:19–21 (1991)). Rational drug design has been used to develop HIV protease inhibitors and agonists for five different somatostatin receptor subtypes. (Erickson et al., *Science* 249:527–533 (1990) and Berk et al., *Science* 282:737 (1998)).

By starting with the sequence or protein models of HuN-Cor or ETO, and/or fragments thereof, polypeptides having two-dimensional and/or three-dimensional homology can be rapidly identified. In a two-dimensional approach, a percent sequence identity can be determined by standard methods that are commonly used to compare the similarity and position of the amino acid of two polypeptides. Using a computer program such as BLAST or FASTA, two polypeptides are aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{\begin{array}{c}[\text{length of the longer sequence within the matched span} + \\ \text{number of gaps introduced into the longer} \\ \text{sequence in order to align the two sequences}]\end{array}} \times 100$$

Accordingly, the protein sequence corresponding to HuN-Cor or ETO is compared to known sequences on a protein basis. Protein sequences corresponding to HuN-Cor or ETO are compared, for example, to known amino acid sequences found in Swissprot release 35, PIR release 53 and Genpept release 108 public databases using BLASTP with the parameter W=8 and allowing a maximum of 10 matches. In addition, the protein sequences encoding HuN-Cor or ETO are compared to publicly known amino acid sequences of Swissprot using BLASTX with the parameter E=0.001. The candidate polypeptides may have the following degrees of homology to HuN-Cor, for example: 50%, 51%, 52%, 53%, 54%, 55%, 56%, 57%, 58%, 59%, 60%, 61%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 93%, 94%, 95%, 96%, 97%, 98%, and 99%. The candidate polypeptides having greater than or equal to 50% homology are identified and are subsequently examined using the functional assays described herein. Candidate polypeptides that can interact with other proteins (e.g., Sin 3, HDAC1, ETO, and AML1/ETO) to modulate the formation of a transcriptional repressor complex and thereby effect transcription are, thus, identified.

Additionally, a search program is used to compare the three-dimensional structure of HuN-Cor or ETO or fragments thereof with other known three-dimensional structures so as to identify HuN-Cor modulating agents that modulate transcriptional repression. In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure may be determined through the use of techniques of neutron diffraction, or by nuclear magnetic resonance (NMR). (See, e.g., Moore, W. J., Physical Chemistry, $4^{th}$ Edition, Prentice-Hall, N.J. (1972)).

Alternatively, the protein model embodiments are constructed using computer-based protein modeling techniques.

By one approach, the protein folding problem is solved by finding target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of a polypeptide of interest (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A fall-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszwdi et al., Proteins:Structure, Function, and Genetics, Supplement 1:38–42 (1997)).

In one approach, a three-dimensional structure of a polypeptide of interest (e.g., HuN-Cor or ETO, and/or fragments thereof or another HuN-Cor modulating agent) is determined by x-ray crystallography, NMR, or neutron diffraction and computer modeling, as described above. Useful protein models of the polypeptide of interest can also be gained by computer modeling alone. Combinatorial chemistry is then employed to design derivatives of the polypeptide of interest based on the three-dimensional models. The candidate HuN-Cor modulating agents are then tested in functional assays. The assays, described herein and assays that evaluate repression of transcription in the presence of HuN-Cor or fragments thereof that will be apparent to one of skill in the art given the disclosure herein (referred to collectively as "HuN-Cor characterization assays") are performed on the HuN-Cor modulating agents and groups of HuN-Cor modulating agents based on the potency of modulation of transcriptional repression are identified and recorded on a computer readable media. Further cycles of modeling and HuN-Cor characterization assays are employed to more narrowly define the parameters needed in a HuN-Cor modulating agent that elicits a desired response.

For example, a HuN-Cor modulating agent can be manufactured and identified as follows. First, a molecular model of one or more HuN-Cor modulating agents or portions of HuN-Cor modulating agents are created using one of the techniques discussed above or as known in the art. HuN-Cor modulating agents that are known to interact with HuN-Cor include antibodies, ETO, AML1/ETO, Sin 3, HDAC1 and fragments thereof. Next, chemical libraries and databases are searched for molecules similar in structure to the known HuN-Cor modulating agents. Identified candidate HuN-Cor modulating agents are then screened in the HuN-Cor characterization assays, described above, and the agents that produce the desired modulation of transcription are used as templates for further library construction. Libraries of HuN-Cor modulating agents are synthesized on solid support beads by split-and-pool synthesis, a multistage process for producing very large numbers of compounds. The support-bound agents are then used in HuN-Cor characterization assays or "free mixtures" are created by cleaving the agent from the support and these free mixtures are screened in the HuN-Cor characterization assays. Compounds that produce desirable responses are identified, recorded on a computer readable media, and the process is repeated to select for optimal HuN-Cor modulating agents.

Each HuN-Cor modulating agent and its response in a HuN-Cor characterization assay is recorded on a computer readable media and a database or library of HuN-Cor modulating agents and respective responses in the HuN-Cor characterization assay is generated. These databases or libraries are used by researchers to identify important property differences between active and inactive molecules so that compound libraries are enriched for HuN-Cor modulating agents that have favorable characteristics. Further, enrichment can be achieved by using approaches in dynamic combinatorial chemistry. (See e.g., Angnew, Chem. Int. Ed., 37:2828 (1998)). For example, a target biomolecule, such as HuN-Cor, is joined to a support and is bound by the HuN-Cor modulating agents from the libraries generated above. The HuN-Cor resin bound with one or more candidate HuN-Cor modulating agents is removed from the binding reaction, the HuN-Cor modulating agents are eluted from the support, and are identified. Cycles of immobilized target binding assays are conducted, classes of HuN-Cor modulating agents that exhibit desired binding characteristics are identified, and this data is recorded on a computer readable media and is used to select more HuN-Cor modulating agents that produce a desired modulation of transcriptional repression.

In addition, a peptide of interest (e.g., HuN-Cor, ETO, and/or fragments thereof or a HuN-Cor modulating agent) can be analyzed by an alanine scan (Wells, Methods in Enzymol. 202:390–411 (1991)). In this technique, an amino acid residue is replaced by alanine, and its affect on the peptide's activity is measured by functional assays, such as the HuN-Cor characterization assays described herein. Each of the amino acid residues of the peptide is analyzed in this manner and the regions important for a specific modulation of transcriptional repression are identified. Subsequently, these functionally important regions are recorded on a computer readable medium, stored in a first database in a computer system, and a search program is employed to generate protein models of the functionally important regions. Once protein models of the functionally important regions have been generated, a second database comprising one or more libraries having peptides, chemicals, peptidomimetics and other agents is accessed by a search program and individual agents are compared to the protein models to identify agents that comprise homologous regions or domains that resemble the identified functionally important regions. Agents identified by the approach above are then tested in the HuN-Cor characterization assays and are used to construct multimeric agents and/or are incorporated into pharmaceuticals, as detailed below.

In another embodiment, computer modeling and the sequence-to-structure-to-function paradigm is exploited to identify more HuN-Cor modulating agents that modulate transcriptional repression. By this approach, first the structure of a HuN-Cor modulating agent having a known response in a HuN-Cor characterization assay (e.g., HuN-Cor, and fragments thereof, antibodies to HuN-Cor, ETO, AML1/ETO, Sin 3 or HDAC1) is determined from its sequence using a threading algorithm, which aligns the sequence to the best matching structure in a structural database. Next, the protein's active site (i.e., the site important for a desired response in the HuN-Cor characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998)).

The FFFs are built by itteratively superimposing the protein geometries from a series of functionally related proteins with known structures. The FFFs are not overly specific, however, and the degree to which the descriptors can be relaxed is explored. In essence, conserved and functionally important residues for a desired inflammatory response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained.

By using this computational protocol, genome sequence data bases such as maintained by various organizations including: http://www.tigr.org/tdb; http://www.genetics.wisc.edu: http://genome-www.stanford.edu/~ball: http://hiv-web.lanl.gov; http://wwwncbi.nlm.nih.gov; http://www.ebi.ac.uk; http://pasteur.fr/other/biology: and http://www-genome.wi.mit.edu, can be rapidly screened for specific protein active sites and for identification of the residues at those active sites that resemble a desired molecule. Several other groups have developed databases of short sequence patterns or motifs designed to identify a given function or activity of a protein. These databases, notably Prosite (http://expasy.hcuge.ch/sprot(prosite.html: Blocks (http://www.blocks.fhcrc.org ); and Prints (http://www.biochem.ucl.ac.uk/bsm/dbbrowser/PRINTS/PRINTS.html), use short stretches of sequence information to identify sequence patterns that are specific for a given function; thus they avoid the problems arising from the necessity of matching entire sequences. In this manner, new HuN-Cor modulating agents are rationally selected for further identification by HuN-Cor characterization assays, as described above. Rounds or cycles of functional assays on the molecules and derivatives thereof and further FFF refinement and database searching allows an investigator to more narrowly define classes of HuN-Cor modulating agents that produce a desired modulation of transcriptional repression.

Many computer programs and databases can be used with the embodiments described herein to identify agents that modulate transcriptional repression. The following list is intended not to limit the invention but to provide guidance to programs and databases that are useful with the approaches discussed above. The programs and databases that may be used include, but are not limited to: MacPattem (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Libraries of information on HuN-Cor modulating agents with their corresponding response in HuN-Cor characterization assays can be generated by performing the rational drug design approaches above in conjunction with the HuN-Cor characterization assays. A record of the results for each HuN-Cor modulating agent is generated and groups of HuN-Cor modulating agents are identified and stored on a computer readable media. Databases of this information are valuable to investigators and clinicians for selecting the type of HuN-Cor modulating agent-based pharmaceutical to treat or elicit a particular transcriptional response. Preferable libraries are created by performing the assays above on HuN-Cor and fragments thereof. The next section describes in greater detail the manufacture and use of HuN-Cor fusion proteins and an assay that evaluates the ability of a Hun-Cor fusion protein to repress transcription.

Gene Specific Transcriptional Repression

Small differences in the levels of a transcription factor, such as a homeobox protein, can specify cell fate during development. Threshold responses are often determined at the level of transcription. Cell-specific and spatially localized patterns of gene expression depend on combinations of sequence-specific activators and repressors that bind to extensive cis-regulatory regions. Coactivators and corepressors can mediate communication between diverse upstream regulatory proteins and the core RNA polymerase II transcription complex. Molecules that specifically alter these patterns of communication can be constructed and used to alter patterns of development. This novel class of gene-specific transcriptional repressor agents can be used to study gene regulation and developmental biology and can be used as the active ingredient in prophylactics and therapeutics that treat diseases that are characterized by over-producing genes and abnormal patterns of development.

In preferred embodiments, the HuN-Cor modulating agents comprise a fusion protein having HuN-Cor or a polypeptide corresponding to a fragment of HuN-Cor joined to a DNA binding protein. Additionally, nucleic acids encoding such fusion proteins are embodiments. Preferably, regions of HuN-Cor that mediate transcriptional repression are joined to a sequence-specific DNA binding protein, such as the DNA binding domain of a transcription factor. Preferred DNA binding domains that are joined to HuN-Cor or a fragment of HuN-Cor include, but are not limited to, AML1/CBF, MyoD, POU, GATA, and homeobox proteins. For example, conventional techniques in molecular biology can be used to fuse a nucleic acid encoding MyoD to a nucleic acid encoding HuN-Cor. This insert can be cloned into an expression vector so as to create a construct that produces a MyoD/HuN-Cor fusion protein. The MyoD/HuN-Cor fusion protein can then be used to shut-off the expression of specific muscle genes. Such constructs or fusion proteins can be incorporated into pharmaceuticals and used to treat diseases associated with an abnormal expression of muscle genes.

Similarly, a construct having a nucleic acid encoding a DNA binding domain of a homeobox protein or the GATA factor fused to HuN-Cor can be used to alter embryonic development. The repression and overexpression of homeobox genes and the resulting phenotypic changes have been well characterized in the literature. (Wright et al. *TIBs* 14:52–56 (1989) and (Gehring *Gene* 135:215–221 (1993)). The 180 nucleotides of the homeobox encode a 60 amino acid homeodomain, which is conserved in many different proteins. (Wright et al. *TIBs* 14:52–56 (1989)). Peptides corresponding to only the homeodomain bind to specific sequences in DNA and three dimensional NMR has proven directly the existence of the helix-turn-helix in a homeodomain peptide. Gain- and loss-of-function mutants of homeobox genes have been tested in transgenic mice. (Gehring *Gene* 135:215–221 (1993)). Disruption of the gene encoding HOX C8, for example, resulted in posterior to anterior transformations, e.g., the conversion of a lumbar segment to a thoracic segment with an additional rib was observed. Additionally, gene-transfer experiments between mouse and *Drosophila* have revealed that HOX B6 of the mouse can induce antennal legs when ectopically expressed in *Drosophila*. The available evidence indicates that homeobox genes encode transcriptional regulators that specify body plan by regulating the activity of the large set of target genes. Transcriptional repression of such genes can be accomplished by using a fusion protein comprising a homeobox DNA binding domain joined to HuN-Cor. These agents can be used as gene-specific tools for the study homeobox gene loss-of-function mutations, for example.

In addition to homeobox genes, other transcription factors, such as the GATA family of transcription factors, have been shown to be important in anterior or posterior embryonic development. (See Sykes et al., *Development* 125:4595–4605 (1998)). GATA factors have been implicated in the development of ventral mesoderm and repression of GATA activity by injection of a dominant-interfering GATA mutant leads to dorsalisation. Further, the expression of genes such as Vent-1 and Went-8 are dependent upon GATA activity and, therefore, patterns of expression of these genes are markers for the suppression of GATA activity. The use of a construct encoding a fusion protein comprising the DNA binding domain of a GATA factor joined to HuN-Cor or a polypeptide fragment encoding HuN-Cor is provided as an example of a gene-specific transcriptional repression agent.

Accordingly, the GATA/HuN-Cor agents can be created by making a construct comprising the DNA binding domain of GATA, the highly conserved zinc finger domain, and HuN-Cor or a fragment thereof using conventional techniques in molecular biology. The region comprising the zinc finger domain of GATA (amino acid 263–380) in X GATA 2 can be amplified by PCR and subcloned into an appropriate expression plasmid. (See Xon et al. *Proc. Natl. Acad. Sci. USA* 88:10642–10646 (1991)). A second construct comprising three GATA binding domains from the mouse a α 1-globin promoter upstream of a minimal promoter from the rabbit β-globin gene is joined to a reporter such as luciferase. The construction of this reporter construct has been described in Sykes et al. The reporter construct and either the GATA/HuN-Cor construct or a control construct comprising the zinc finger domain of GATA joined to the repressor domain from the *Drosophila* engrailed protein or wild-type GATA are microinjected into *Xenopus* oocytes. The engrailed domain extends from amino acids to 298 and a control construct can be made as described in the literature. (See, e.g., Sykes et al., and Badiani et al., *Genes Dev.*, 8:770–782 (1994)).

Culture and microinjection of *Xenopus* embryos are conducted as described by Walmsley et al., *Development*, 101:815–827 (1987)). Briefly, embryos are injected at the 4-cell stage into two adjacent blastomers. Oocytes are injected with 2–10 ng of mRNA into the cytoplasm, and cultured overnight at 18° C. Oocytes are then injected with 5 ng of reporter DNA, targeting the injection to the germinal vesicle. To reduce non-specific initiation from cryptic cites, 20 ng of plasmid DNA (pGEM7) is co-injected in each case. After 24 hours, luciferase assays are performed on the oocytes extracts according to the manufacturers instructions (Promega). As described in the literature, injection of the construct having the zinc finger domain of GATA joined to the repressor domain from the *Drosophila* engrailed protein will induce formation of a secondary axes that is incomplete in that it lacks head and notochord structures yet contains a neural tube, ectopic muscle, and an ectopic gut lumen. Similarly, injection of the construct comprising the zinc finger domain of GATA joined to HuN-Cor will induce formation of an incomplete secondary axes that lacks head and notochord structures yet contains a neural tube, ectopic muscle and an ectopic gut lumen.

A second assay for evaluating the GATA/HuN-Cor agent involves the ability of the agent to rescue UV-ventralization. In these experiments, embryos are UV-irradiated at the 1-cell stage and are injected at the 4cell stage with 50 pg–10 ng of a construct comprising the zinc finger domain of GATA joined to HuN-Cor. UV treatment of embryos can be performed by placing them in a quartz petri dish and irradiating the vegetal poles for 2–3 minutes with a UV lamp suspended 7 cm below. The extent of dorsoventral axis formation can be quantified according to the Dorso-Anterior Index (DAI; Kao and Elinson *Dev. Biol.* 127:64–77 (1988)). Injection of the GATA/HuN-Cor construct, as well as a control construct comprising the zinc finger domain of GATA joined to the repressor domain from the *Drosophila* engrailed protein, are able to rescue trunk and tail axial development, but do not result in head formation. Neural tube and muscle are observed but no notochord are observed. These experiments will demonstrate that a construct comprising a DNA binding domain joined to HuN-Cor can effectively repress the transcription of genes involved in ventral cell fate.

Additionally, the lack of expression of genes associated with ventralizing properties can be analyzed by whole-mount in situ hybridization. (See, Bertwistle et al., *Mech. Dev.* 57:199–214 (1996)). After injection of 50 pg–10 ng of a construct comprising the zinc finger domain of GATA joined to HuN-Cor, the expression of homeobox transcription factors that are known to have ventralising properties, including but not limited to, Vent-1, Vent-2, Went-8, and BMP-4 are monitored. Injection of 50 pg of a construct comprising zinc finger domain of GATA joined to the repressor domain of the *Drosophila* protein engrailed can be used as a positive control. The expression of Vent-1 and Went-8 is repressed in oocytes injected with either the control construct or the construct comprising the GATA binding domain joined to HuN-Cor. In addition to whole-mount in situ hybridization, reverse transcriptase-PCR using primers described in Sykes et al. can be used to quantitate the level of transcriptional repression induced by the GATA/HuN-Cor construct.

While the experiments detailed above provide an elegant approach to demonstrate that fusion proteins comprising HuN-Cor repress transcription of specific genes, modifications of these HuN-Cor characterization assays can be used to evaluate the ability of any fusion protein comprising a DNA binding protein joined to HuN-Cor to repress transcription. Accordingly, a general HuN-Cor characterization assay to evaluate such fusion proteins involves co-transfection of a first construct comprising a DNA binding domain joined to HuN-Cor and a second construct comprising one or more binding sites for the DNA binding protein joined to a minimal promoter and a reporter such as luciferase, chloramphenicol acetyl transferase (CAT), or green fluorescent protein (GFP). The two constructs are transfected into an appropriate cell line and the reporter signal generated is evaluated according to techniques known in the art. Additionally, a third construct comprising sequence encoding the wild-type transcription factor that binds to the DNA binding element joined to the reporter construct can be transfected and competition between the construct having HuN-Cor and the wild-type transcription factor can be evaluated. In this manner, the efficacy of fusion constructs comprising HuN-Cor joined to a DNA binding protein are rapidly evaluated. Further, approaches in high throughput screening can be applied so as to automate the methods detailed above.

Many of the HuN-Cor modulating agents are provided in biotechnological tools, diagnostics, and pharmaceuticals as multimeric or multimerized agents or both that can be joined to a support. The next section describes the preparation of multimeric supports and multimerized HuN-Cor modulating agents that comprise HuN-Cor or fragments of HuN-Cor, complementary nucleic acids to HuN-Cor, HuN-Cor or fragments of HuN-Cor, antibodies or antibody fragments that recognize epitopes of HuN-Cor, and HuN-Cor fusion proteins.

Preparation of Multimeric Supports and Multimerized HuN-Cor Modulating Agents

A useful biotechnological tool or a component to a prophylactic or therapeutic agent provides HuN-Cor or fragments of HuN-Cor, complementary nucleic acids to HuN-Cor, HuN-Cor or fragments of HuN-Cor, antibodies or antibody fragments that recognize epitopes of HuN-Cor, and HuN-Cor fusion proteins in such a form or in such a way that a sufficient affinity or modulation of transcriptional repression is achieved. While a natural monomeric agent (that is, an agent that presents a discrete molecule, thus, carrying only one binding epitope or domain) is sufficient to enhance transcriptional repression or inhibit transcriptional repression, a synthetic agent or a multimeric agent (e.g., an agent that presents multiple molecules, thus, having several binding epitopes or domains) often times has greater ability to modulate transcriptional repression. It should be noted that the term "multimeric" refers to the presence of more than one molecule on an agent, for example, several individual molecules of an antibody joined to a support, as distinguished from the term "multimerized" that refers to an agent that has more than one molecule joined as a single discrete compound molecule on a support, for example several antibody molecules joined to form a single compound molecule that is joined to a support.

A multimeric agent (synthetic or natural) that modulates transcriptional repression is obtained by joining HuN-Cor, fragments of HuN-Cor, complementary nucleic acids to HuN-Cor, HuN-Cor, fragments of HuN-Cor, antibodies or antibody fragments that recognize epitopes of HuN-Cor, and HuN-Cor fusion proteins (collectively referred to as "HuN-Cor modulating agents") to a macromolecular support. HuN-Cor modulating agents including peptidomimetics and chemical molecules that resemble these ligands are also joined to supports so as to create the multimeric agents of the invention. A "support" is also termed a carrier, a resin or any macromolecular structure used to join or immobilize a HuN-Cor modulating agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, Duracyte® artificial cells, and others.

In several embodiments, the macromolecular support has a hydrophobic surface that interacts with a portion of the HuN-Cor modulating agent by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, the HuN-Cor modulating agent is covalently bound to carriers including proteins and oligo/polysaccarides (e.g. cellulose, starch, glycogen, chitosane or aminated sepharose). In these later embodiments, a reactive group on a HuN-Cor modulating agent, such as a hydroxy or an amino group, is used to join to a reactive group on the carrier so as to create the covalent bond. Embodiments also comprise a support with a charged surface that interacts with the HuN-Cor modulating agent. Additional embodiments comprise a support that has other reactive groups that are chemically activated so as to attach a HuN-Cor modulating agent, such as a peptide or chemical compound. For example, cyanogen bromide activated matrices, epoxy activated matrices, thio and thiopropyl gels, nitrophenyl chloroformate and N-hydroxy succinimide chloroformate linkages, or oxirane acrylic supports are used. (Sigma).

Inorganic carriers, such as silicon oxide material (e.g. silica gel zeolite, diatomaceous earth or aminated glass) to which the HuN-Cor modulating agent is covalently linked through a hydroxy, carboxy or amino group and a reactive group on the carrier are also embodiments. Carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine and Chromosorb® (Johns-Manville Products, Denver Colo.). Conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, the administration of a "naked" carrier (i.e., lacking an attached HuN-Cor modulating agent) that has the capacity to attach a HuN-Cor modulating agent that modulates transcriptional repression inside the body of a subject is performed. By this approach, a "prodrug-type" therapy is administered in which the naked carrier is provided separately from the desired HuN-Cor modulating agent and, once both are in the body, the carrier and the HuN-Cor modulating agent assemble into a multimeric complex and modulate transcriptional repression.

In another embodiment, linkers, such as 8 linkers (generated from the flexible arms of 8 phage), of an appropriate length are inserted between the HuN-Cor modulating agent and the support so as to encourage greater flexibility in the HuN-Cor modulating agent and thereby overcome any steric hindrance that is presented by the support. The determination of an appropriate length of linker that allows for optimal binding and modulation of transcriptional repression, is made by screening the HuN-Cor modulating agents with varying linkers in the HuN-Cor characterization assays described in the present disclosure.

A composite support comprising more than one type of HuN-Cor modulating agent is also an embodiment. A "composite support" is a carrier, a resin, or any macromolecular structure used to join or immobilize two or more different HuN-Cor modulating agents that modulate the transcriptional repression. The composite supports are also constructed by utilizing hydrophobic interactions and covalent linkages formed through reactive groups, as detailed above. Further, linkers, such as 8 linkers, of an appropriate length between the HuN-Cor modulating agents and the support are inserted in some embodiments so as to encourage greater flexibility in the molecule and overcome steric hindrance. The determination of an appropriate length of linker that allows for optimal binding and modulation of transcriptional repression, is made by screening the HuN-Cor modulating agents with varying linkers in the HuN-Cor characterization assays detailed in the present disclosure.

In some embodiments, a composite support comprises a support joined to HuN-Cor proteins or polypeptide fragments thereof and one or more proteins associated in a transcriptional repressor complex including, but not limited to, ETO, AML1/ETO, HDAC1, and Sin3. According to the methods mentioned above, natural, synthetic, mutant, recombinant, or multimerized derivatives of HuN-Cor and a protein such as, ETO, AML1/ETO, HDAC1, and Sin3, or polypeptide fragments thereof are bound to the composite support. By one approach, ETO protein or AML1/ETO is joined to a support and HuN-Cor is associated with the ETO or AML1/ETO in a manner that maintains the native conformation of the HuN-Cor protein. Alternatively, HuN-Cor is joined to the support and ETO and AML1 is joined in a manner that maintains native protein conformation. Further, ETO and AML1/ETO and HuN-Cor protein or polypeptide fragments thereof can be crosslinked to each other and joined to the support so as to provide greater stability and durability of the ETO or AML1/ETO-HuN-Cor complex. The aforementioned composite supports can provide high affinity for interacting proteins involved in a transcriptional activation complex and would be particularly useful as a biotechnological tool. Additionally, natural, synthetic, mutant, recombinant, or multimerized derivatives of HuN-Cor fusion proteins can be engineered using conventional techniques and are useful in applications that seek to identify the interacting proteins of a transcriptional repression complex and have application in therapeutic and phrophylactic pharmaceuticals.

In other embodiments, the multimeric and composite supports discussed above have attached multimerized HuN-Cor modulating agents so as to create a "multimerized-multimeric support" and a "multimerized-composite support", respectively. An embodiment of a multimerized HuN-Cor modulating agent, for example, is obtained by creating an expression construct having two or more nucleotide sequences encoding the HuN-Cor modulating agent protein or fragments thereof joined together by using conventional techniques in molecular biology. The expressed fusion protein is one embodiment of a multimerized agent and is then joined to a support. A support having many such multimerized agents is termed a multimerized-multimeric support. The multimerized form of the HuN-Cor modulating agent can be advantageous for many applications because of the ability to obtain an agent with a better ability to modulate transcriptional repression. The incorporation of linkers or spacers, such as flexible 8 linkers, between the protein domains that make-up the multimerized agent can also be advantageous for some embodiments. The insertion of 8 linkers of an appropriate length between protein binding domains, for example, encourages greater flexibility in the molecule and overcomes steric hindrance between the several proteins. Similarly, the insertion of linkers between the multimerized HuN-Cor modulating agent and the support encourages greater flexibility and reduces steric hindrance presented by the support. The determination of an appropriate length of linker that allows for optimal binding and modulation of transcriptional repression can be accomplished by screening the HuN-Cor modulating agents with varying linkers in the HuN-Cor characterization assays detailed in this disclosure. In a similar fashion composite-multimerized-multimeric supports with and without linkers can be constructed by joining more than one different multimerized HuN-Cor modulating agent to a support. The next section describes several diagnostic embodiments.

Diagnostic Embodiments

Healthy subjects have different concentrations of HuN-Cor or different expression levels of HuN-Cor in various tissues and fluids than subjects afflicted with a HuN-Cor-related disease, such as cancer. Accordingly, several diagnostic and prognostic tools that detect the concentration and expression level of nucleic acids encoding HuN-Cor and the concentration and expression level of HuN-Cor in various tissues and fluids are used to determine whether an individual is suffering from a HuN-Cor-related disease or is likely to suffer from a HuN-Cor-related disease in the future.

Generally, the diagnostics and methods of use thereof can be classified according to whether the diagnostic detects the concentration or expression level of HuN-Cor nucleic acid or HuN-Cor protein in a biological sample (e.g., a sample having nucleic acids or proteins or both). Accordingly, the concentration and expression level of HuN-Cor in a biological sample, for example, can be determined by monitoring the amount of RNA in the sample. A concentration of RNA encoding HuN-Cor in a sample that is outside the range considered to be acceptable for healthy individuals (e.g., higher or lower) indicates the existence or predilection to a HuN-Cor related disease. Further, a detection of a concentration of DNA encoding HuN-Cor in a biological sample that is outside the range considered to be acceptable for healthy individuals (e.g., higher or lower) indicates the existence or predilection to a HuN-Cor related disease. Similarly, the concentration and expression level of HuN-Cor in a biological sample can be determined by monitoring the amount of HuN-Cor protein in the sample. A concentration of HuN-Cor in a sample that is outside the range considered to be acceptable for healthy individuals (e.g., higher or lower) indicates the existence or predilection to a HuN-Cor related disease.

To determine if the concentration or expression level of HuN-Cor or HuN-Cor in a subject is aberrant, a biological sample from one or more tissues or fluids is obtained. Several methods known to those in the art can be employed to obtain tissues and fluids from various sources in the body including but not limited to phlebotomy and tissue biopsy. Once a biological sample from a subject in need of testing is obtained, many different techniques can be used to detect the concentration and expression level of HuN-Cor or HuN-Cor including, but not limited to, antibody-based detection techniques (e.g., ELISA, sandwich assays, immunoprecipitation, and immunoblots), bacteriophage display techniques, hybridization techniques (e.g., Southern and Northern), and enzymatic digestion (e.g., RNAse protection) techniques. Some of these techniques can involve disposing the proteins and/or nucleic acids present in the biological sample on a support, and contacting the support with detection reagents such as antibodies to HuN-Cor or nucleic acid probes complementary to HuN-Cor mRNA. Desirably, the levels of expression or concentration of HuN-Cor or HuN-Cor or both from diseased and healthy individuals are compared to the level detected in the subject tested.

In preferred embodiments, the nucleic acid embodiments are attached to a support (e.g., a gene chip) in an ordered array wherein a plurality of nucleic acid probes are attached to distinct regions of the support that do not overlap with each other. Preferably, such an ordered array is designed to be "addressable" wherein the distinct locations of the probe are recorded and can be accessed as part of an assay procedure. (See Example 3).

In some embodiments, addressable nucleic acid arrays comprise a plurality of nucleic acid probes that complement HuN-Cor. These probes are joined to a support in different known locations. The knowledge of the precise location of each nucleic acid probe makes these "addressable" arrays particularly useful in binding assays. For example, an addressable array can comprise a support having several regions to which are joined a plurality nucleic acid probes that complement HuN-Cor. The nucleic acids from a preparation of several biological samples from a plurality of human subjects or a plurality of tissues or fluids from a single subject are labeled by conventional approaches (e.g., radioactivity or flourescence) and the labeled samples are applied to the array under conditions that permit hybridization If a nucleic acid in the samples hybridizes to a probe on the array, then a signal will be detected at a position on the support that corresponds to the location of the hybrid. Since the identity of each labeled sample is known and the region of the support on which the labeled sample was applied is known, an identification of the presence, concentration, and/or expression level can be rapidly determined. That is, by employing labeled standards of a known concentration of a nucleic acid encoding HuN-Cor, (e.g., RNA), an investigator can accurately determine the concentration of a nucleic acid encoding HuN-Cor in a sample and from this information can assess the expression level of HuN-Cor. Conventional methods in densitometry can also be used to more accurately determine the concentration or expression level of a nucleic acid encoding HuN-Cor. These approaches are easily automated using technology known to those of skill in the art of high throughput diagnostic analysis.

Additionally, an opposite approach to that presented above can be employed. Nucleic acids present in biological samples (e.g., tissues or fluids from one or more subjects or one or more sources in a subject's body) can be disposed on a support so as to create an addressable array. Preferably, the samples are disposed on the support at known positions that do not overlap. The presence of nucleic acids encoding HuN-Cor in each sample is determined by applying labeled nucleic acid probes that complement nucleic acids that encode HuN-Cor and detecting the presence of a signal at locations on the array that correspond to the positions at which the biological samples were disposed. Because the identity of the biological sample and its position on the array is known, an identification of the presence, concentration, and/or expression level of a nucleic acid encoding HuN-Cor is rapidly determined. That is, by employing labeled standards of a known concentration of a nucleic acid encoding HuN-Cor, (e.g., RNA), an investigator can accurately determine the concentration of a nucleic acid encoding HuN-Cor in a sample and from this information can assess the expression level of HuN-Cor. Conventional methods in densitometry can also be used to more accurately determine the concentration or expression level of a nucleic acid encoding HuN-Cor. These approaches are also easily automated using technology known to those of skill in the art of high throughput diagnostic analysis.

Any addressable array technology known in the art can be employed with this aspect of the invention. One particular embodiment of polynucleotide arrays is known as Genechips™, and has been generally described in U.S. Pat. No. 5,143,854; PCT publications WO 90/15070 and 92/10092. These arrays are generally produced using mechanical synthesis methods or light directed synthesis methods, which incorporate a combination of photolithographic methods and solid phase oligonucleotide synthesis. (Fodor et al., *Science*, 251:767–777, (1991)). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and diagnostic information. Examples of such presentation strategies are disclosed in PCT Publications WO 94/12305, WO 94/11530, WO 97/29212 and WO 97/31256.

A wide variety of labels and conjugation techniques are known by those skilled in the art and can be used in various nucleic acid assays. There are several ways to produce labeled nucleic acids for hybridization or PCR (Polymerase Chain Reaction) including, but not limited to, oligolabeling, nick translation, end-labeling, or PCR amplification using a labeled nucleotide. Alternatively, a nucleic acid encoding HuN-Cor, or any portion of it, can be cloned into a vector for the production of an mRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

For diagnostic and prognostic purposes, nucleic acid probes having a sequence complementary to a nucleic acid encoding HuN-Cor or a portion thereof can be used to detect and quantitate gene expression in biological samples including, but not limited to biopsied tissues or biological fluids, as discussed above. Preferably, nucleic acid probes that are complementary to mRNA encoding HuN-Cor are used to screen for polynucleotides present in blood. RNA-detection-based diagnostic assays, such as Northern hybridization, Northern dot blots, RNA in situ hybridization, and ELISA assays, are particularly useful to distinguish between the absence, presence, and excess expression of HuN-Cor and to monitor regulation of HuN-Cor levels during therapeutic intervention.

Included in the scope of the embodiments described herein are the use of oligonucleotide sequences, antisense RNA and DNA molecules, and PNAs that complement HuN-Cor sequences for the determination of HuN-Cor concentrations and expression levels in the cells of a subject by RNA-based detection techniques. These forms of polynucleotide sequences encoding HuN-Cor or fragments thereof can also be used for the diagnosis of conditions or diseases with which aberrant expression of HuN-Cor is associated. For example, polynucleotide sequences complementary to mRNA encoding HuN-Cor can be used in hybridization or PCR assays of fluids or tissues from biopsies to detect and quantify HuN-Cor expression and, upon comparison with the expression levels or concentrations of healthy individuals or other diseased individuals or both, the disease state or predilection to disease of the tested subject can be determined. The form of such qualitative and/or quantitative methods can include Northern analysis, dot blot or other membrane-based technologies; PCR technologies; dip stick, pin, chip, and ELISA technologies. All of these techniques are well known in the art and are the basis of many commercially available diagnostic kits.

In one aspect, RNA probes complementary to HuN-Cor mRNA are used in assays that detect activation or induction associated with disease (e.g., cancer). Accordingly, the nucleotide sequence encoding HuN-Cor or a fragment thereof is used to design suitable RNA probes. The RNA probes are labeled by methods known in the art and are added to a DNAse treated fluid or tissue sample from a subject under conditions suitable for the formation of hybridization complexes. Hybridization complexes are isolated or the sample is treated with an agent that removes unhybridized nucleic acids. After an incubation period, the sample is washed with a compatible fluid a that optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with RNA in the sample, and the presence of elevated levels of RNA encoding HuN-Cor or a portion thereof in the sample indicates the presence of a HuN-Cor-related disease, such as cancer.

Such assays can also be used to evaluate the efficacy of a particular therapeutic treatment regime in animal studies, in clinical trials, or in monitoring the treatment of an individual patient. In order to provide a basis for the diagnosis of disease, a normal or standard profile for HuN-Cor expression in isolated cells, extracts, or tissue is desirably established. This is accomplished by combining body fluids or cell extracts taken from healthy subjects with RNA probes encoding HuN-Cor, or a portion thereof, under conditions suitable for hybridization. Standard hybridization can be quantified by comparing the values obtained for healthy and diseased subjects with a dilution series of HuN-Cor RNA run in the same experiment where a known amount of substantially purified HuN-Cor is used. Standard values obtained from samples from healthy and diseased subjects are then compared with values obtained from samples from the tested subjects. Deviation between standards and the values obtained for the subject tested establishes the presence or predilection for a HuN-Cor-related disease.

Additionally, PCR methods that can be used to quantitate the concentration and expression level of a particular molecule include radiolabeling (Melby P. C. et al. J Immunol Methods 159:235–44 (1993)) or biotinylating nucleotides (Duplaa C. et al. Anal Biochem 212:229–236 (1993)), coamplification of a control nucleic acid, and standard curves onto which the experimental results are interpolated. Quantitation of multiple samples can be processed more rapidly by running the assay in an ELISA format where the oligomer of interest is presented in various dilutions and a spectrophotometric or calorimetric response gives rapid quantitation. A definitive diagnosis of this type can allow health professionals to create a disease state profile for a patient, begin aggressive treatment for the HuN-Cor-related disease, and prevent further worsening of the condition. Similarly, further assays and reference to the changing disease state profile can help clinicians monitor the progress of a patient during treatment. That is, once a disease state is established, a therapeutic agent is administered and an initial disease state profile is generated. The assays above can be repeated on a regular basis to evaluate whether the values in the subject's disease state profile progresses toward or returns back to the initial disease state profile. Successive treatment profiles can be used to show the efficacy of treatment over a period of several days or several months.

As mentioned above, PCR technology can be used to identify and quantitate concentration and expression levels of HuN-Cor. For amplification of mRNAs, it is within the scope of the present invention to reverse transcribe mRNA into cDNA followed by PCR (RT-PCR); or to use a single enzyme for both steps as described in U.S. Pat. No. 5,322, 770, or to use Reverse Transcriptase Asymmetric Gap Ligase Chain Reaction (RT-AGLCR), as described by Marshall R. L. et al. (*PCR Methods and Applications* 4:80–84, 1994)).

A variety of PCR techniques are familiar to those skilled in the art. For a review of PCR technology, see Molecular Cloning to Genetic Engineering White, B A. Ed. in *Methods in Molecular Biology* 67: Humana Press, Totowa (1997) and the publication entitled "PCR Methods and Applications," Cold Spring Harbor Laboratory Press (1991). In each of these PCR procedures, PCR primers on either side of the HuN-Cor sequence to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188.

The primers are selected to be substantially complementary to a portion of the sequence of HuN-Cor mRNA and a portion of the sequence that complements the sequence of HuN-Cor mRNA, thereby allowing the sequences between the primers to be amplified. The length of the primers for use with aspects of the present invention can range from 8 to 100 nucleotides, preferably from 8 to 50, 8 to 30 or more preferably 8 to 25 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions may be empirically determined by one of skill in the art.

The spacing of the primers determines the length of the segment to be amplified. In the context of the present invention amplified segments carrying nucleic acid sequence encoding fragments of HuN-Cor can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for HuN-Cor can be of any sequence that allows the specific amplification of any DNA fragment carrying nucleic acid sequence unique HuN-Cor. Amplification primers can be labeled or immobilized on a solid support as described above.

The presence of HuN-Cor protein can be detected by screening for the presence of the protein using conventional assays. For example, monoclonal antibodies immunoreactive with HuN-Cor can be used to screen biological samples for the presence, concentration, and expression level of HuN-Cor and, thereby, provide diagnostic information about HuN-Cor-related diseases. Such immunological assays can be done in many convenient formats.

In one embodiment, antibodies are used to immunoprecipitate HuN-Cor from solution and, in another embodiment, antibodies are used to react with HuN-Cor on Western or Imnnunoblots of a polyacrylamide gel. In desirable embodiments, antibodies are used to detect HuN-Cor in paraffin or frozen sections, using immunocytochemical techniques. Favored embodiments for detecting HuN-Cor include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530.

In preferred protein-based diagnostic embodiments, the antibodies described herein are attached to a support in an ordered array wherein a plurality of antibodies are attached to distinct regions of the support that do not overlap with each/other. As with the nucleic acid-based arrays, the protein-based arrays are ordered arrays that are designed to be "addressable" such that the distinct locations are recorded and can be accessed as part of an assay procedure.

In some embodiments, addressable antibody arrays comprise a plurality of antibodies that recognize HuN-Cor. These probes are joined to a support in different known locations. The knowledge of the precise location of each probe makes these "addressable" arrays particularly useful in binding assays. For example, an addressable array can comprise a support having several regions to which are joined a plurality antibody probes that recognize HuN-Cor. Proteins from a preparation of several biological samples from a plurality of human subjects or a plurality of tissues or fluids from a single subject are labeled by conventional approaches (e.g., radioactivity, colorimetrically, or fluorescently) and the labeled samples are applied to the array under conditions that permit binding. If a protein in the samples binds to an antibody probe on the array, then a signal will be detected at a position on the support that corresponds to the location of the antibody-protein complex. Since the identity of each labeled sample is known and the region of the support on which the labeled sample was applied is known, an identification of the presence, concentration, and/or expression level is rapidly determined. That is, by employing labeled standards of a known concentration of HuN-Cor, an investigator can accurately determine the protein concentration of HuN-Cor in a sample and from this information can assess the expression level of HuN-Cor.

Conventional methods in densitometry can also be used to more accurately determine the concentration or expression level of HuN-Cor. These approaches are easily automated using technology known to those of skill in the art of high throughput diagnostic analysis.

In another embodiment, an opposite approach to that presented above can be employed. Proteins present in biological samples (e.g., tissues or fluids from one or more subjects or one or more sources in a subject's body) can be disposed on a support so as to create an addressable array. Preferably, the protein samples are disposed on the support at known positions that do not overlap. The presence of a protein encoding HuN-Cor in each sample is then determined by applying labeled antibody probes that recognize epitopes of HuN-Cor and detecting a signal at locations on the array that correspond to the positions at which the biological samples were disposed. Because the identity of the biological sample and its position on the array is known, an identification of the presence, concentration, and/or expression level HuN-Cor is rapidly determined. That is, by employing labeled standards of a known concentration of HuN-Cor, an investigator can accurately determine the concentration of HuN-Cor in a sample and from this information can assess the expression level of HuN-Cor. Conventional methods in densitometry can also be used to more accurately determine the concentration or expression level of HuN-Cor. These approaches are also easily automated using technology known to those of skill in the art of high throughput diagnostic analysis. As detailed above, any addressable array technology known in the art can be employed with this aspect of the invention so as to display the protein arrays on the chips in an attempt to maximize antibody binding patterns and diagnostic information.

As discussed above, a detection of an aberrant concentration or expression level of HuN-Cor can provide a diagnosis of a subject's disease state or predilection to disease and this information allows health professionals to create a disease state profile for a patient, begin aggressive treatment for the HuN-Cor-related disease, and prevent further worsening of the condition. Similarly, further assays and reference to the changing disease state profile can help clinicians monitor the progress of a patient during treatment. That is, once a disease state is established, a therapeutic agent is administered and an initial disease state profile is generated. The assays above can be repeated on a regular basis to evaluate whether the values in the subject's disease state profile progresses toward or returns back to the initial disease state profile. Successive treatment profiles can be used to show the efficacy of treatment over a period of several days or several months.

Additional embodiments include the preparation of diagnostic kits comprising detection components such as antibodies specific for HuN-Cor or nucleic acid probes for detecting RNA encoding HuN-Cor. The detection component will typically be supplied in combination with one or more of the following reagents. A support capable of absorbing or otherwise binding RNA or protein will often be supplied. Available supports for this purpose include, but are not limited to, membranes of nitrocellulose, nylon or derivatized nylon that can be characterized by bearing an array of positively charged substituents, and Genechips™ or their equivalents. One or more enzymes, such as Reverse Transcriptase and/or Taq polymerase, can be furnished in the kit, as can dNTPs, buffers, or non-human polynucleotides like calf-thymus or salmon-sperm DNA. Results from the kit assays can be interpreted by a healthcare provider or a diagnostic laboratory. Alternatively, diagnostic kits are manufactured and sold to private individuals for self-diagnosis. The section below describes several embodiments that have therapeutic and/ or prophylactic application.

Therapeutic and Prophylactic Applications

Many of the HuN-Cor modulating agents are suitable for the treatment of subjects either as a preventive measure to avoid HuN-Cor-related diseases, or as a therapeutic to treat subjects already afflicted with a HuN-Cor-related disease. Although anyone could be treated with the HuN-Cor modulating agents as a prophylactic, the most suitable subjects are people at risk for HuN-Cor related diseases. Such subjects include, but are not limited to, individuals with a family history of certain forms of cancer including, but not limited to, leukemia.

The pharmacologically active compounds described herein can be processed in accordance with conventional methods of galenic pharmacy to produce medicinal agents for administration to patients, e.g., mammals including humans. The HuN-Cor modulating agents can be incorporated into a pharmaceutical product with and without modification. Further, the manufacture of pharmaceuticals or therapeutic agents that deliver the HuN-Cor modulating agent or a nucleic acid sequence encoding a HuN-Cor modulating agent by several routes are aspects of the invention. For example, and not by way of limitation, pharmaceuticals that comprise DINA, RNA, and viral vectors having sequence encoding HuN-Cor or a polypeptide fragment of HuN-Cor are embodiments. Nucleic acids encoding a desired HuN-or modulating agent can be administered alone or in combination with other HuN-Cor modulating agents.

The compounds described herein can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfumer oil, fatty acid monoglycerides and diglycerides, pentaerythritol fatty acid esters, hydroxy methylcellulose, polyvinyl pyrrolidone, etc. Many more suitable vehicles are described in *Remmington's* Pharmaceutical Sciences, 15th Edition, Easton:Mack Publishing Company, pages 1405–1412 and 1461–1487 (1975) and The National *Formulary* XIV, 14th Edition, Washington, American Pharmaceutical Association (1975). The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation having a HuN-Cor modulating agent can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). In this vein, N-Cor modulating agents, which resemble HuN-Cor modulating agents except that they correspond to N-Cor peptides and nucleic acids encoding N-Cor peptides, may be used in experiments with mice to determine suitable doses in mammals. The data obtained from these assays is then used in formulating a range of dosage for use with humans. The dosage of such compounds lies preferably within a range of circulating concentrations that include the ED50 with no toxicity. The dosage varies within this range depending upon type of HuN-Cor modulating agent, the dosage form employed, sensitivity of the organism, and the route of administration.

Normal dosage amounts of various HuN-Cor modulating agents can vary from approximately 1 to 100,000 micrograms, up to a total dose of about 10 grams, depending upon the route of administration. Desirable dosages include, for example, less than 250 μg, 500 μg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5 g, 6 g, 7 g, 8 g, 9 g, and 10 g.

In some embodiments, the dose of HuN-Cor modulating agent preferably produces a tissue or blood concentration or both from approximately 0.1 μM to 500 mM. Desirable doses produce a tissue or blood concentration or both of about 1 to 800 μM. Preferable doses produce a tissue or blood concentration of greater than about 10 μM to about 5004 μM. Preferable doses are, for example, the amount of HuN-Cor modulating agent required to achieve a tissue or blood concentration or both of less than 10 μM, 15 μM, 20 μM, 25 μM, 30 μM, 35 μM, 40 μM, 45 μM, 50 μM, 55 μM, 60 μM, 60 μM, 65 μM, 70 μM, 75 μM, 80 μM, 85 μM, 90 μM, 95 μM, 100 μM, 110 μM, 120 μM, 130 μM, 140 μM, 145 μM, 150 μM, 160 μM, 170 μM, 180 μM, 190 μM, 195 μM, 200 μM, 220 μM, 240 μM, 250 μM, 260 μM, 280 μM, 300 μM, 320 μM, 340 μM, 360 μM, 380 μM, 400 μM, 420 μM, 440 μM, 460 μM, 480 μM, and 500 μM. Although doses that produce a tissue concentration of greater than 500μM are not preferred, they can be used with some embodiments. A constant infusion of the HuN-Cor modulating agent can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the HuN-Cor modulating agents include, but are not limited to, topical, transdermal, parenteral, gastrointestinal, transbronchial, and transalveolar. Topical administration is accomplished via a topically applied cream, gel rinse, etc. containing a peptide. Transdermal administration is accomplished by application of a cream, rinse, gel, etc. capable of allowing the HuN-Cor modulating agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of HuN-Cor modulating agent-containing compounds suitable for topical application include, but not limited to, physiologically acceptable implants, ointments, creams, rinses, and gels. Any liquid, gel, or solid, pharmaceutically acceptable base in which the HuN-Cor modulating agents are at least minimally soluble is suitable for topical use. Suitable compositions for such use include, but are not limited to, vaginal or anal suppositories, creams, and douches.

Compositions of the HuN-Cor modulating agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al.

Compositions of the HuN-Cor modulating agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the HuN-Cor modulating agents.

Compositions of the HuN-Cor modulating agents suitable for transbronchial and transalveolar administration include, but not limited to, various types of aerosols for inhalation. Devices suitable for transbronchial and transalveolar administration of the HuN-Cor modulating agents are also embodiments. Such devices include, but are not limited to, atomizers and vaporizers. Many forms of currently available atomizers and vaporizers can be readily adapted to deliver HuN-Cor modulating agents.

Compositions of the HuN-Cor modulating agents suitable for gastrointestinal administration include, but are not limited to, pharmaceutically acceptable powders, pills or liquids for ingestion and suppositories for rectal administration. Due to the ease of use, gastrointestinal administration, particularly oral, is a preferred embodiment.

Other embodiments include methods of treating and preventing HuN-Cor-related diseases including, but not limited to, cancers such as leukemia Example 2 describes experiments that were performed on leukemia cells to determine if HuN-Cor modulating agents could be used as cancer therapeutics. As described infra, it was discovered that HuN-Cor modulating agents induced leukemia cells to differentiate. It is well understood in the art that the differentiation of leukemia cells can inhibit the progression of the cancer.

Some of the therapeutic embodiments can be practiced by identifying an animal in need of a HuN-Cor modulating agent and then is providing said animal an amount of the HuN-Cor modulating agent that is effective to modulate the repression of transcription. In preferred embodiments, the animal is provided a HuN-Cor modulating agent that corresponds to or resembles a region of HuN-Cor that interacts with a transcriptional complex (e.g., a region of HuN-Cor that corresponds to amino acid residues 988–1,816 and/or amino acid residues 1551–1803 and nucleic acids that encode these molecules). In other preferred embodiments, the animal is provided a HuN-Cor modulating agent that corresponds to or resembles a region of ETO that interacts with a transcriptional complex (e.g., a region of ETO that corresponds to a zinc finger motif and nucleic acids that encode these molecules). The nucleic acid and protein sequence of a region of ETO that corresponds to one or both zinc finger motifs can be discerned by one of skill in the art from the sequence provided in GenBank Accession number S78158 or in Era et al., *Genes Chromosomes Cancer* 13: 25–33 (1995).

In some embodiments, an animal in need of a HuN-Cor modulating agent can be identified by the diagnostic approaches described supra. For example, animals that express too much or too little HuN-Cor can be animals in need of a HuN-Cor modulating agent. Additionally, subjects that have cancer or are at risk of contracting cancer (e.g., individuals with a family history of cancers such as leukemia) are animals in need that can be identified by conventional techniques including, but not limited to, clinical diagnosis and genetic testing. Once an animal in need is identified, they are provided an amount of HuN-Cor modulating agent that is sufficient to modulate (inhibit or enhance) the repression of transcription. A discussed above, this amount may vary according to the type of HuN-Cor-related disease, the patient, and the HuN-Cor modulating agent. In this regard, the dosages described for the pharmaceutical embodiments can be suitable for the methods of treating and preventing HuN-Cor related diseases. Example 1 describes several of the materials and methods used to perform the experiments discussed above.

EXAMPLE 1

This example describes many of the materials and methods that were used to discover the embodiments described herein.

Two-hybrid Methodology:

The entire cDNA coding region of human ETO (MTG8a) was generated by polymerase chain amplification (PCR) using pCRIVETO as a template. The amplified fragment was inserted into the pGBT9 plasmid (Clontech). DNA sequencing was performed to confirm the in-frame fusion between ETO and the GAL4 DNA binding, domain (DBD). A human fetal brain cDNA library (Clontech) inserted into the pGAD10 plasmid containing the GAL4 activation domain was screened using the pGBT9-ETO cDNA as bait HF7c yeast cells were transformed with pGBT9-ETO and the library plasmid DNA and grown on Trp⁻, Leu⁻ and His⁻ selective medium plates. The colonies were transferred onto filter paper and frozen in liquid nitrogen to lyse the yeast cells. β-galactosidase assays (performed multiple times to exclude false positives) were performed to identify potential positive colonies. Plasmids were extracted from yeast and used to transform E. coli HB101 cells. Plasmids extracted from E. coli were then analyzed by DNA sequencing.

In vitro Protein Interaction Analysis: Glutathione S-Transferase (GST) Pull Down Assay:

The B2 insert was recovered and cloned into pGEX-5X-1 (Pharmacia), creating an in-frame fusion to GST. GST and GST-B2 fusion proteins were expressed in BL21 E. coli cells, and equal amounts of each were immobilized onto glutaihione sepharose beads. The beads were incubated for 12 hours with $S^{35}$-labelled full-length ETO protein produced by in vitro translation (Promega). The beads were washed with cell lysis buffer (10 mM Tris-HCl, 150 mM NaCl, 1 mM EDTA, 1% NP40, 1% deoxycholic acid, 10 μg/ml leupeptin, 1 μg/ml pepstatin, 1 μg/ml aprotinin, 1 mM PMSF) three times. Proteins, eluted by glutatione elution buffer, were subjected to SDS- polyacrylamide gel electrophoresis (PAGE) and autoradiography.

Cloning of the Full Length HuN-Cor cDNA:

Using the B2 insert fragment as a probe, human fetal brain cDNA libraries (D. Tagle, NIH) were screened. A total of six overlapping fragments were obtained and analyzed by automated DNA sequencing (Perkin Elmer).

Immunoprecipitation and Western Blot Experiments:

293 cells were transfected by calcium phosphate co-precipitation with mammalian expression plasmids expressing ETO or AML1/ETO (S. Hiebert, Vanderbilt) alone or with Flag epitope-tagged HDAC1 (S. Schreiber, Harvard University) or Flag-tagged N-CoR (M. G. Rosenfeld, University of California, San Diego). The cells were cultured for two days post-transfection, collected, resuspended in cell lysis buffer (PBS containing 0.1% NP40, 1 mM EDTA, 1 g/ml pepstatin, 1 mM PMSF) and sonicated. Cell lysates were obtained after centrifugation at 10,000 rpm for 2 minutes. The M2 monoclonal antibody against the Flag epitope (Sigma), rabbit polyclonal antibody against mSin3A (Santa Cruz Biotechnology), or rabbit polyclonal antibody against ETO (Calbiochem) and 20 μl protein A/G agarose were added to cell lysates. Immunoprecipitation was performed at 4° C. for 12 hours. Following centrifugation, washing with cell lysis buffer, and denaturation, immunoprecipitate proteins were applied to SDS-PAGE gels for electrophoresis. Proteins were transferred onto nitrocellulose membranes, and blocking was performed in TBST buffer (10 mM Tris-HCl, 150 mM NaCl, 0.05% Tween-20) containing 5% non-fat milk. Western blotting was done with rabbit polyclonal antibodies against either AML1/runt homology domain (RHD) (Calbiochem) or ETO. Proteins were visualized by anti-rabbit IgG conjugated with alkaline phosphatase (Promega).

Construction of ETO Truncation Expression Plasmids:

Carboxy-terminal deletions of pGBT9/ETO were constructed (Erase-a-Base System, Promega). PCR was applied using pCRII/ETO (12) as a template, the unique antisense primer 5'-CGC GGA TCC CAG TTC TGA GTT CAC GTC-3' (SEQ. ID NO.: 5), and the following sense primers: 5'-CG GAA TTC TCA AGC GAG AGT TGC TGG-3' (SEQ. ID NO.: 6) (to amplify ETO amino acids 484–578) and 5'-CG GAA TTC AAC ACA GCC CGA TAC TGT-3' (SEQ. ID NO.: 7) (to amplify ETO amino acids 503–578). The amplified fragments were ligated into the pGBT9 vector (fused in-frame with the GAL4 DBD).

Mammalian Expression Vector Construction:

To construct an expression vector for ETO, PCR was performed using pCRII/ETO as template with the following primers: 5'-GCTCT AGAACCTGATCGTACTGA G-3' (SEQ. ID NO.: 8) and 5'-CGGGGTACCTCGCGTTGGTT GTGTT-3' (SEQ. ID NO.: 9). PCR fragments were inserted into the pFA-CMV plasmid (Stratagene) to create GAL4 DBD/ETO.

Mammalian Cell Transfection:

Transfections of CV-1 (ATCC) cells were performed with varying amounts (indicated in FIG. 5) of GAL4 DBD/ETO, 2.0 μg of the luciferase reporter plasmid, 1.0 μg of the CMX-β-galactosidase plasmid (R. Evans and D. Chen, Salk Institute) as an internal control, and varying amounts of the pUC19 plasmid to maintain equal amounts of transfected DNA among the different experimental groups. The reporter plasmid contains four copies of the GAL4 binding site upstream of the TK promoter (B. O'Malley, Baylor Medical School). The RARα LBD plasmid was from R. Evans and D. Chen. Luciferase activity was normalized by β-galactosidase determinations. The example below describes experiments that verified that HuN-Cor modulating agents can be used to induce differentiation of leukemia cells.

EXAMPLE 2

This example describes experiments that verified that HuN-Cor modulating agents can be used to treat or prevent cancer (e.g., leukemia). The t(8;21), found in 30% of FAB M2 leukemias, produces the chimeric fusion protein AML1-ETO. The ETO component of this fusion has been shown to interact with the nuclear receptor co-repressor (N-CoR) complex, which includes Sin3 and the histone deacetylase HDAC1. Consequently, the transcription of genes normally regulated by AML1 may be repressed by AML1-ETO, thus blocking differentiation pathways. Operating on this premise, experiments were designed, using expression constructs that encode the interacting domains of ETO and N-CoR, to determine whether the interaction between AML1-ETO S and N-CoR could be disrupted and whether such a disruption could initiate differentiation and apoptosis programs in AML 1-ETO leukemia cells.

Initially, a yeast two hybrid analysis was performed to identify the regions of HuN-Cor and/or N-Cor that are involved in binding ETO. This assay revealed that two domains of HuN-Cor and/or N-Cor (amino acid residues 988–1126 and 1551–1803) were involved in binding to ETO. Sequences encoding the zinc-finger domains of ETO (ETOZn) and the ETO-interacting domain of N-CoR (NCoREID) were then inserted into the retroviral vector pLEGFP-N1 (Clontech), creating fusions with the enhanced green fluorescent protein, GFP. The retroviral vectors were constructed by PCR amplification with primers that incorporated XhoI digestion sites.

The t(8;21) containing leukemia cell-line Kasumi-1 was then transduced with either ETOZn, NCoREID or insert-less pLEGFP-N1 (negative control) vectors. Flow cytometry was then used to specifically analyze transduced cells that stained for GFP, CD13-PE (a marker of myelomonocytic differentiation) expression, and annexin-PE (a marker of apoptosis). It was found that 89±7% of ETOZn and 87±10% of NCoREID transduced cells were positive for CD13 expression, compared to 35±17% of pLEGFP-N1 transduced cells (p<0.005, t-test). In addition, 97±2% of ETOZn and 97±2% of NCoREID transduced cells were positive for annexin staining. In other experiments, ETOZn and NCoR-EID had no effect on the t(15;17) containing cell-line NB4, which verifies the specificity of the above experiments.

These results demonstrate that the interaction between AML1-ETO and NCoR is crucial to the differentiation block and viability of the t(8;21) containing cell line Kasumi-1. Further, these results establish that HuN-Cor modulating agents can be used to specifically disrupt the protein-protein interactions that allow for the assembly and stability of a transcriptional complex having HuN-Cor and ETO and, thereby, inhibit the proliferation of leukemia cells, as demonstrated by the induction of differentiation and apoptosis.

The example below describes a diagnostic assay that can be used to detect the presence or absence or amount of a HuN-Cor nucleic acid in a sample.

EXAMPLE 3

The following describes a diagnostic assay that employs the nucleic acid embodiments described herein to detect the presence or absence, and concentration of a HuN-Cor nucleic acid in a biological sample. Accordingly, a probe is first prepared by adding the following reagents to a test tube:

2 µl polyA+RNA (1–3 µg/reaction) obtained from the biological sample
1 µl anchored oligo dT primer (1 µg/µl)
2 µl dH$_2$O The reagents are mixed gently, heated at 70° C. for 5 min. and chilled on ice for 2 min. Next, the following are added to the tube:

6 µl 5×MMLV RT (reverse transcriptase) buffer
1.5 µl 10 mM dGTP
1.5 µl 10 mM dTTP
1.5 µl 10 mM dATP
3 µl 50 µM dCTP
10 µl $^{33}$P-dCTP (>2500 µCi/mmol)

The reagents are again mixed, quickly spin in microfuge for 30 sec., and incubated at 42° C. for 3 min. Subsequently, 1.5 µl of MMLV-RT (Promega) is added and the reaction is allowed to proceed at 42° C. for 5 min. Approximately, 1 µl of 10 mM dCTP and continue incubation at 42° C. for 1 hr. The reaction is terminated by heating at 65° C. for 10 min. after adding:

1.5 µl 1N NaOH
1.0 µl 0.2M EDTA

The reaction is then neutralized by adding 1.5 µl 1N HCL and the reaction is passed through a G50 spin column to remove unincorporated nucleotides. Approximately, 1 µl of the labeled probe is counted by scintillation to estimate the labeling efficiency and the counts are desirably about 10 million cpm per µl from a total volume of 30 µl. Before using the probe, an equal volume of formamide is added and the mixture is heated at 95° C. for 5 min. and then chilled on ice for 3 min.

Once the probe is prepared, the prehybridization is set up. A hybridization chamber is obtained and a gene chip (e.g., a SmartArray chip) having a nucleic acid embodiment disposed thereon (e.g., a HuN-Cor nucleic acid or fragment thereof or complement thereto) is placed face down onto the chamber. If necessary, the gene chip is positioned in the middle of the chamber by pressing the chip downward, evenly and firmly. Next, the chip is prehybridized in hybridization buffer that is approximately 42° C. For some hybridization chambers and gene chips assemblages (e.g., a SmartArray chip assemblage), only 500 µl of heated buffer is added to the chamber through one of the ports on the hybridization chamber and the chamber is filled to about 90%, leaving an air-space sufficient in size to allow agitation of the hybridization buffer during incubation. The surface area around the port is dried with a piece of Kimwipe and an adhesive seal is placed onto each port and depressed when both seals are in place. Next the chips having a nucleic acid embodiment are placed into a plastic bag and the entire unit is inserted into a hybridization bottle and rotated at low speed (6 rpm) in a 42° C. oven for 30 min.

Following the prehybridization, the probe is added and the hybridization reaction is allowed to occur. Accordingly, the denatured probe is added into 500 µl of hybridization solution that has been brought up to 42° C. The gene chip is placed on a clean, flat surface and both seals are removed with forceps. The pre-hybridization solution is then removed from a port using a pipetman. The pre-heated hybridization solution is then added into the chamber, leaving an air bubble to allow agitation and the ports are dried and cleaned completely. Two new seals are then placed onto the ports, as described above. The hybridization reaction is allowed to occur at 42° C. for 3 hr. to overnight.

After hybridization, the chip is washed. First, the seals are removed and the hybridization solution is withdrawn. The hybridization chamber is removed with forceps and the slide is placed immediately into 2×SSC/0.1% SDS. The slides should not be allowed to dry. The slides are washed twice at 42° C. for 10 min per wash in this buffer. Next, the slides are washed twice in 0.25×SSC/0.1% SDS at 42° C. for 10 min per wash. The excess wash buffer is removed from the slide and the back of the slide is dried with a Kimwipe. Next, the gene chip is wrapped with plastic wrap and exposed to xray film or, preferably, a phosphoimager. The presence of a HuN-Cor RNA in the biological sample will be detected as a black spot on the array. A phosphoimager is preferred because the concentration of probe bound to the HuN-Cor target nucleic acid can be determined if a saturating amount of target is used. Desirably, control samples are also analyzed so that the concentration of HuN-Cor RNA in a sample can be more accurately accessed. For example, the hybridization described above can be performed in parallel with other hybridizations that began the probe preparation step with a known quantity of HuN-or RNA.

Although the invention has been described with reference to embodiments and examples, it should be understood that various modifications can be made without departing from the spirit of the invention. All references cited herein are hereby expressly incorporated by reference.

What is claimed is:

1. A purified or isolated nucleic acid comprising the sequence of SEQ ID NO: 1 or a full complement thereof.

2. A purified or isolated nucleic acid selected from the group consisting of nucleotides 3202–3618 of SEQ ID NO: 1 and nucleotides 4891–5649 of SEQ ID NO: 1.

3. A purified or isolated nucleic acid comprising at least 13 consecutive bases of the sequence of SEQ ID NO: 1 or a full complement thereof, wherein the nucleic acid has a nucleotide sequence not found in SEQ ID NO: 2.

4. A purified or isolated nucleic acid encoding a polypeptide having the sequence of SEQ ID NO: 3.

5. A purified or isolated nucleic acid encoding a polypeptide selected from the group consisting of amino acid residues 988–1126 of SEQ ID NO: 3 and 1551–1803 of SEQ ID NO: 3.

6. A gene chip array wherein the improvement comprises a purified or isolated nucleic acid comprising at least 13 consecutive bases of the sequence of SEQ ID NO: 1 or a full complement thereof, wherein the nucleic acid has a nucleotide sequence not found/in SEQ ID NO: 2.

* * * * *

UNITED STATES PATENT AND TRADEMARK OFFICE
CERTIFICATE OF CORRECTION

| | |
|---|---|
| PATENT NO. | : 6,949,624 B1 |
| APPLICATION NO. | : 09/632033 |
| DATED | : September 27, 2005 |
| INVENTOR(S) | : Liu et al. |

It is certified that error appears in the above-identified patent and that said Letters Patent is hereby corrected as shown below:

In Col. 92, Line 55 (approx.), Claim 6, delete "found/in" and insert -- found in --.

Signed and Sealed this

Twentieth Day of February, 2007

JON W. DUDAS
*Director of the United States Patent and Trademark Office*

SEQUENCE LISTING

<160> NUMBER OF SEQ ID NOS: 9

<210> SEQ ID NO 1
<211> LENGTH: 7940
<212> TYPE: DNA
<213> ORGANISM: Artificial Sequence
<220> FEATURE:
<223> OTHER INFORMATION: cDNA encoding human nuclear receptor co-
      Represser (HuN-Cor)

<400> SEQUENCE: 1

| | | | | | | |
|---|---|---|---|---|---|---|
| ccaagatggc | ggccaaggtg | gcgaagcagc | agccgcggcg | gcggcggcgg | ctggagtgag | 60 |
| cgtccgactc | gccgcgccga | acgaggtccc | ggtgtagggc | cgcgcgccgt | ggccgcgtcc | 120 |
| cactcctcag | gccggggcgc | acgtcggctc | ccacgcttag | ccagctcccg | gtggtttcct | 180 |
| agaaacatga | ttgtttattg | gcattgatct | cacagtctgg | tgaggacttc | tttactgata | 240 |
| atgtcaagtt | caggttatcc | tcccaaccaa | ggagcattca | gcacagaaca | aagtcgttat | 300 |
| cctcctcact | ctgtccagta | tacatttccc | aacacccgcc | accagcagga | gttcgcagtc | 360 |
| cctgattatc | gttcctctca | tcttgaagtg | agtcaggcat | cacagctttt | gcagcaacag | 420 |
| cagcagcaac | agcttcgaag | gcgaccttcc | ttgctttcag | aatttcaccc | aggttctgac | 480 |
| aggcctcaag | aaaggagaac | tagttatgaa | ccgtttcatc | aggcccatc | cccagtggat | 540 |
| catgattcac | tggaatcgaa | gcgaccacgt | ctggaacagg | tttctgattc | tcattttcag | 600 |
| cgtgtcagtg | ctgcggtttt | gcctttagtg | cacccgctgc | cagaagggct | gagggcttct | 660 |
| gcagatgcta | gaaggatcc | agcattcgga | ggcaaacatg | aagctccatc | ctctccaatt | 720 |
| tcggggcaac | catgtggaga | tgatcaaaat | gcttcacctt | caaaactctc | aaaggaagag | 780 |
| ttaatacaga | gtatggatcg | tgtagatcga | gaaattgcaa | agtagaaca | gcagatcctt | 840 |
| aaactgaaaa | agaaacaaca | acagcttgaa | gaagaggcag | ctaaacctcc | tgagcctgag | 900 |
| aagcccgtgt | cccctcctcc | tgtggagcag | aaacaccgca | gtattgtcca | aattatttat | 960 |
| gatgagaatc | ggaaaaaagc | agaagaagct | cataaaattt | ttgaaggtct | tggcccaaaa | 1020 |
| gttgaactgc | cactgtataa | ccagccatca | gataccaagg | tgtaccatga | aacatcaag | 1080 |
| acaaaccagg | tgatgaggaa | aaaactcatt | ttattttta | aaagaagaaa | tcatgcaaga | 1140 |
| aaacaaaggg | aacaaaaaat | ctgccagcgt | tatgatcagc | tcatggaggc | atgggagaaa | 1200 |
| aaagtggaca | gaatagaaaa | taatcctcgg | aggaaagcta | agaaagcaa | acaagggaa | 1260 |
| tactatgaaa | agcagtttcc | agaaattcga | aaacaaagag | aacagcaaga | agatttcag | 1320 |
| cgagttgggc | agagggggagc | tggtctttca | gccaccattg | ctaggagtga | gcatgagatt | 1380 |
| tctgaaatta | ttgatgggct | ctctgagcag | gagaataatg | agaaacaaat | gcggcagctc | 1440 |
| tctgtgattc | cacctatgat | gtttgatgca | gaacaaagac | gagtcaagtt | cattaacatg | 1500 |
| aatgggctta | tggaggaccc | tatgaaagtg | tataaagata | ggcagtttat | gaatgttttgg | 1560 |
| actgaccatg | aaaaggagat | ctttaaggac | aagtttatcc | agcatccaaa | aaactttgga | 1620 |
| ctaattgcat | catacttgga | gaggaagagt | gttcctgatt | gtgttttgta | ttactattta | 1680 |
| accaagaaaa | atgagaatta | taagccctc | gtcagaagga | attatgggaa | acgcagaggc | 1740 |
| agaaaccagc | aaattgctcg | accctcgcaa | gaagaaaaag | tagaagaaaa | agaagaggat | 1800 |
| aaagcagaaa | aaacagaaaa | aaagaagaa | gaaagaaag | atgaagagga | aaagatgaa | 1860 |
| aaagaagact | ccaagaaaaa | taccaaggaa | aaggacaaga | tagatggtac | agcagaagaa | 1920 |

```
actgaggaaa gagagcaagc cacaccccgg gggcgaaaga ctgccaacag tcagggccgc    1980
cgtaagggcc ggatcaccag gtccatgaca acgaagctg cagctgccag tgctgcagcc     2040
gcagcggcta ctgaagagcc cccaccacct ctgccaccgc caccagaacc catttctaca    2100
gagcctgtgg agacctctcg atggacagaa gaagaaatgg aagttgctaa aaaaggtcta    2160
gtagaacatg gtcgtaactg ggcagcaatt gctaaaatgg tgggaacgaa aagtgaagct    2220
caatgtaaaa acttctattt taactataaa aggcgacaca atcttgacaa cctcttacag    2280
cagcataaac agaaaacttc acgaaaacct cgtgaagagc gagatgtgtc tcaatgtgaa    2340
agtgtcgctt ccactgtttc tgctcaggag gatgaagata ttgaagcctc caatgaagaa    2400
gaaaatccag aagacagcga agttgaagct gtcaagccca gcgaggacag tcctgaaaat    2460
gctacttctc gaggaaacac agaacctgcg gttgagcttg agcccaccac ggaaactgca    2520
cccagtacat ctccctcctt agcagttcca agtacaaaac cagctgaaga tgaaagtgtg    2580
gagacccagg tgaatgacag catcagtgct gagacagcag agcagatgga tgtagatcag    2640
caggagcaca gtgctgaaga gggttctgtt tgtgatcccc cacccgctac caaagctgac    2700
tctgtggacg ttgaagtgag ggtgccagaa aaccatgcat ctaaagttga aggtgataat    2760
accaaagaaa gagacttgga tagagccagt gagaaggtgg aacctagaga tgaagatttg    2820
gtggtagctc agcaaataaa tgcccaaagg cccgagcccc agtcagacaa tgattccagt    2880
gccacgtgca gcgctgatga ggatgtggat ggagagccag agaggcagag aatgtttcct    2940
atggactcaa agccttcact gttaaaccccc actggatcta tactcgtctc atctccgtta    3000
aaaccaaatc cactggatct gccacagctt cagcatcgag ctgctgttat cccaccaatg    3060
gtatcctgca ccccatgtaa cataccaatt ggaaccccag tgagcggcta tgctctctac    3120
cagcgacaca ttaaagcaat gcatgagtca gcactcctgg aggagcagcg gcagagacaa    3180
gaacagatag atttggaatg tagaagttct acaagtccat gtggcacatc caagagtcca    3240
aacagagagt gggaagtcct tcagcctgct ccacatcaat tgataactaa tctccctgaa    3300
ggcgttcggc ttccgacaac tcgaccaacc aggccaccgc cccctctcat cccgtcatcc    3360
aaaaccacag tggcttcaga aaaaccatct tttataatgg gaggctccat ctcacaggga    3420
acaccaggca cttatttgac ttctcataat caggcttcct acactcaaga acacccaag     3480 ccgtcagtag gatctatctc tcttggactg ccacggcaac aggaatctgc caaatcagct    3540
actttgccct acatcaagca ggaagaattt tctccccgaa gccaaaactc acaacctgag    3600
ggtctgttgg tcagggccca acatgaaggt gtagtcagag gtaccgcagg agccatacaa    3660
gaaggaagta taactcgggg aactccaacc agcaaaattt cagtggagag cattccatcc    3720 ctacgggct ctatcactca gggcacccccg gctctgcccc agactggcat accaacagag    3780
gctttggtga agggtccat ttcgagaatg cccattgaag acagcagtcc tgagaaaggc    3840
agagaggaag ctgcatccaa aggccatgtt atttatgaag gcaaaagtgg acatatcttg    3900
tcatatgata atattaagaa tgcccgagaa gggactagga gtccaagaac agctcatgaa    3960
atcagtttaa agagaagcta tgaatcagtg aaggaaata taaagcaagg gatgtcaatg    4020
agggagtctc ctgtatcagc accgttagag gggctgatat gccgagcatt acccaggggg    4080
agtcctcatt ctgacctcaa agaaggact gtattgtctg gctccataat gcagggaca     4140 ccaagagcaa caactgaaag ctttgaagat ggccttaaat atcccaaaca aattaaaagg    4200
gaaagtcctc ccatacgagc atttgaaggt gccattacca aaggaaaacc atatgatggc    4260
atcaccacca tcaaagaaat ggggcgttcc attcatgaga ttccaaggca agatatttta    4320
```

-continued

```
actcaggaaa gtcggaaaac tccagaagtg gtccagagca cacggccgat aattgagggt      4380
tccatttccc agggcacacc aataaagttt gacaacaact caggtcaatc tgccatcaaa      4440
cacaatgtca atccttaat cacggggcct agcaaactat cccgtggaat gcctccgctg       4500
gaaattgtgc cagagaacat aaaagtggta gaacgggaa aatatgagga tgtgaaagca       4560
ggcgagaccg tgcgttccccg gcacacgtca gtggtaagct ctggcccctc cgttcttagg     4620
tccacactgc atgaagctcc caaagcacaa ctgagccctg ggatttatga tgacaccagt     4680
gcacggagga cccctgtgag ttatcaaaac accatgtcca gaggctcacc catgatgaac     4740
agaacttctg atgttacaat tcctcctaac aagtctacca atcatgaaag gaaatcgaca     4800
ctgaccccta cccagaggga agtatccca gcgaagtctc cagtgcctgg ggtggaccct     4860
gtcgtgagcc acagtccgtt tgatccccat cacagaggca gcactgcagg cgaggtttat     4920
tggagccacc tgcccacgca attggatcca gccatgcctt tcacagggc tttggatcct      4980
gcagcggctg cttacctgtt tcagagacag cttcaccaa ctccaggtta cccaagtcag      5040
tatcagcttt acgcaatgga gaacacaaga cagacaatct aaatgatta cattaccctca    5100
caacagatgc aagtgaactt gcgtccagat gtggccagag gactctcccc aagagagcag    5160
ccactgggtc tcccataccc agcaacgaga ggaatcattg acctgaccaa tatgcctcca     5220
acaatttag tgcctcatcc aggggaaca agcactcctc ccatggacag aatcacttat      5280
attcctggta cacagattac tttccctccc aggccgtaca actctgcttc catgtctcca     5340
ggacacccaa cacccttgc agctgctgca agtgctgaga gggaacggga acgggagcgg    5400
gagaaggagc gggagcggga acggattgct gcagcttcct ccgacctcta cctgcggcca     5460
ggctcagaac agcctggccg acctggcagt catggatatg ttcgctcccc ttccccttca      5520
gtaagaactc aggagaccat gttgcaacag agacccagtg ttttccaagg aaccaatgga    5580
accagtgtaa tcacacccttt ggatccaact gctcagctac gaatcatgcc actgcctgct    5640
gggggcccctt caataagcca aggcctgcca gcctcccgtt acaacactgc tgcggatgcc    5700
ctggctgctc ttgtgatgc tgcagcttct gcaccccaga tggatgtgtc caaaacaaaa     5760
gagagtaagc atgaagctgc caggttagaa gaaaatttga gaagcaggtc agcagcagtt    5820
agtgaacagc agcagctaga gcagaaaacc ctggaggtgg agaagagatc tgttcagtgt    5880
ttatacactt cttcagcctt tccaagtggc aagccccagc ctcattcttc agtagtttat     5940
tctgaggctg ggaaagataa agggcctcct ccaaaatcca gatatgagga agagctaagg     6000
accagaggga agactaccat tactgcagct aacttcatag acgtgatcat cacccggcaa    6060
attgcctcgg acaaggatgc gagggaacgt ggctctcaaa gttcagactc ttctagtagc    6120
ttatcttctc acaggtatga aacacctagc gatgctattg aggtgataag tcctgccagc    6180
tcacctgcgc caccccagga gaaactgcag acctatcagc cagaggttgt taaggcaaat    6240
caagcggaaa atgatcctac cagacaatat gaaggaccat tacatcacta tcgaccacag    6300
caggaatcac catctcccca caacagctg cccccttctt cacaggcaga gggaatgggg    6360
caagtgccca ggaccatcg gctgatcaca cttgctgatc acatctgtca aattatcaca    6420
caagattttg ctagaaatca agtttcctcg cagactcccc agcagcctcc tacttctaca     6480
ttccagaact caccttctgc tttggtatct acacctgtga ggactaaaac atcaaaccgt    6540
tacagcccag aatcccaggc tcagtctgtc catcatcaaa gaccaggttc aagggtctct    6600
ccagaaaatc ttgtggacaa atccagggga agtaggcctg gaaaatcccc agagaggagt    6660
```

| | |
|---|---:|
| cacgtctctt ccgagccta cgagcccatc tccccacccc aggttccggt tgtgcatgag | 6720 |
| aaacaggaca gcttgctgct cttgtctcag aggggcgcag agcctgcaga gcagaggaat | 6780 |
| gatgcccgct caccagggag tataagctac ttgccttcat tcttcaccaa gcttgaaaat | 6840 |
| acatcaccca tggttaaatc aaagaagcag gagattttc gtaagttgaa ctcctctggt | 6900 |
| ggaggtgact ctgatatggc agctgctcag ccaggaactg agatctttaa tctgccagca | 6960 |
| gttactacgt caggctcagt tagctctaga ggccattctt ttgctgatcc tgccagtaat | 7020 |
| cttgggctgg aagacattat caggaaggct ctcatgggaa gctttgatga caaagttgag | 7080 |
| gatcatggag ttgtcatgtc ccagcctatg ggagtagtgc ctggtactgc caacacctca | 7140 |
| gttgtgacca gtggtgagac acgaagagag gaaggggacc catcacctca ttcaggagga | 7200 |
| gtttgcaaac caaagctgat cagcaagtca acagcagga atctaagtc tcctataccct | 7260 |
| gggcaaggct acttaggaac ggaacggccc tcttcagtct cctctgtaca ttcagaaggg | 7320 |
| gattaccata ggcagacgcc agggtgggcc tgggaagaca ggccctcttc aacaggctca | 7380 |
| actcagtttc cttataaccc tctgactatg cggatgctca gcagtactcc accaacaccg | 7440 |
| attgcatgtg ctccctctgc ggtgaaccaa gcagctcctc accaacagaa caggatctgg | 7500 |
| gagcgagagc ctgccccact gctctcagca cagtacgaga ccctgtcgga tagtgatgac | 7560 |
| tgaactgcac aaagtgaggg gaacaggggtg caggagaggg atctctagtt tttgtggttt | 7620 |
| aatttttagt agcaggtcaa aaacctgccc tcctgtgact tattccctga acttttcag | 7680 |
| gagagccagc ccacagatga tgaagaaatg atggaagttc atttggagag tcaaatggga | 7740 |
| aaaaaacaaa caaaaaactg cctttgatac aggcaattca gtggactata ataatagtgg | 7800 |
| agggttgaga tgtagagttt ttaaaaagtg aacagttgct gttcttacat ctgtaaagaa | 7860 |
| aaccataatg tctttaaatc actcttctgt aaatagatga ccttttttgca gtgtaaaaaa | 7920 |
| aaaaaaaaaa aaaaaaaaaa | 7940 |

```
<210> SEQ ID NO 2
<211> LENGTH: 7780
<212> TYPE: DNA
<213> ORGANISM: Artificial Sequence
<220> FEATURE:
<223> OTHER INFORMATION: cDNA encoding murine nuclear receptor co-
      receptor (N-Cor)
<220> FEATURE:
<221> NAME/KEY: misc_feature
<222> LOCATION: (1)...(7780)
<223> OTHER INFORMATION: n = A,T,C or G

<400> SEQUENCE: 2
```

| | |
|---|---:|
| ccgtggactt cagcggggag cgtctgcaaa ggcccccgac gtcctgagtg atttcctaga | 60 |
| agcatggttt tttgttgccc ttgacctccc agcctggtga ggcctctgtc ctgagaatgt | 120 |
| caagttcagg ttatcctccc aaccaggggg cgttcagcac agagcagagt cgctacccctt | 180 |
| cgcactcggt tcagtacacc tttcccagcg cccgtcacca gcaggaattt gcagtccctg | 240 |
| actaccgttc ttctcatctt gaagtcagtc aggcgtcaca gctcttgcag cagcagcagc | 300 |
| agcagcagct tcgcagacgg ccttccctgc tttccgagtt tcacccgggt tccgacaggc | 360 |
| cccaggaaag gagaagtgga tacgagcagt tccacccggg ccccttccccg gtggaccatg | 420 |
| actcgctgga gtccaagcgg cctcgcctgg agcaggtttc cgactccac ttccagcgca | 480 |
| tcagtgctgc cgtcctccct ttggtgcaca cgctgccaga aggactgagg tcttctgcca | 540 |
| atgctaagaa ggatccggca tttggagtca aacatgaagc tccttcctct cccctctctg | 600 |

```
ggcagccatg cggagatgat cagaatgcct caccttcaaa actgtcaaag gaagagctga      660
tacagagcat ggatcgtgtc gatcgagaaa ttgcgaaagt agaacagcag atccttaaac      720
tgaaaaagaa gcagcaacag ctcgaagaag aagctgctaa accccagag cctgagaagc       780 ctgtgtcccc tcctcccgtg gagcagaagc accgaagtat tgtccaaatc atttatgacg      840
agaatcggaa aaaagcagaa gaagctcata aatatttga aggtcttggc ccaaaagttg       900
aactgccgct ctacaaccag ccgtcagata ccaaggtgta ccacgagaac atcaagacaa      960
accaggtgat gaggaaaaaa ctcatttat tttttaaaag aagaaatcat gcaagaaaac      1020
aaagggaaca aaaaatctgc caacgttatg atcagctcat ggaagcatgg gagaaaaag     1080 tggacagaat agaaaataat cctcggagga aagctaaaga aagcaaaaca agggaatact    1140
atgaaaagca gtttccagaa attcgaaaac aaagagaaca gcaagaaaga tttcagcgag    1200
ttggtcagag gggagctggt ctttcagcca ccattgctag gagtgagcat gagatttctg    1260
aaattattga tggtctttct gaacaggaga ataatgagaa gcaaatgcgt cagctttctg    1320
tgattccacc tatgatgttt gatgcagaac aaagaagggt caaattcatc aatatgaatg    1380
ggctgatgga ggatccaatg aaggtttata agcacagaca gtttatgaat gtttggactg    1440
accatgaaaa ggagatcttt aaggacaagt ttatccagca tccaaaaaac tttggactaa    1500
ttgcatccta tttggaaagg aagagtgttc ctgattgtgt tttatattac tatttaacca    1560
agaaaaatga gaattataag gccctcgtga aaggaatta tggaaaacgc agaggcagaa     1620
atcagcagat tgcccgtccc tcacaagaag aaaaagtaga agaaaaggaa gaggataaag    1680
cagaaaaaac agagaaaaag gaagaagaaa agaaggatga tgaagaaaaa gatgataagg    1740
aagactctaa agaacaaacc aaggaaaagg acagaacgga agccacagca gaagaacctg    1800
aagaaagaga gcaggtcact ccaaggggc gaaagactgc taacagccaa ggccgcggga    1860
agggccgggt caccaggtcg atgacaagtg aagctgcagc tgccaatgct gctgctgcag    1920
ccactgagga gccccgcca cccctgccgc caccaccaga gcccatttct acagaacctg    1980
ttgagacttc aagatggaca gaagaagaaa tggaagttgc taaaaaaggc ctggtagaac    2040
atggtcgtaa ctgggcagcc attgctaaaa tggtgggaac taaaagtgaa gcccagtgca    2100
aaaacttcta ttttaactat aaaagacggc ataatcttga caacctttg cagcaacata     2160 aacagaaagc ttcacggaaa ccccgtgagg aacgagatgt atctcagtgt gaaagtgttg    2220
cttccactgt ttctgcccaa gaggatgaag atattgaagc tcaaatgag gaggaaaatc      2280 cagaagatag tgaaggtgct gaaaatagtt ctgatacaga aagtgctccc tctccttcac    2340
cagttgaagc tgccaagtcc agtgaagaca gcagtgaaaa tgctgcttct cgaggaaaca    2400
ccgagcctgt ggctgagctt gaggccacca ctgaccctgc accctgtgca tctccctctt    2460
cagcagttcc aaccacaaaa ccagcagaaa gggaaagcgt ggaggcccag gtgaccgaca    2520
gcgccagtgc cgagaccgca gagccgatgg acgtagacca tgaggagtgc ggtgccgagg    2580
gcagttctgt tcttgatcca ccagccccta ccaaagccga ctccgtggac ccagaaatgc    2640
aggtaccaga aaatactgcg tctaaaggtg aaggggatgc caaggaaaga gacttggaga    2700
gcaccagtga gaagacagag gctagagatg aagacgtggt agtggctgaa cagatcgaga    2760
ggcctgagcc acagtcagac gacgactcca gtgccacttg cagtgcggat gagggtgtgg    2820
atggagagcc agagaggcag agagtgtttc ccatggatgc aaagccttca ttgttaactc    2880
ctcctggatc tatcctaatc tcatccccta ttaaaccaaa cctattggat ctgccacagc    2940
ttcagcatcg agctgctgtt attccaccaa tggtttcttg cactccatgt aatataccaa    3000
```

```
ttggaacgcc cgtaagtggc tatgctcttt accaacggca cattaaggcc atgcatgagt    3060
cagcactcct ggaggagcag cggcagaggc aagaacaggt agacttggaa tgcagaagct    3120
ctacaagccc atgcagcact tctaagagtc caaacaggga gtgggaagtc ctccaacctg    3180
ctccgcatca agtgataact aaccttcctg aagggttcg gcttccaaca acacgaccaa     3240
ccaggccacc acctcccctc atcccatcat ctaaaaccac agtggcatca gaaaaaccat    3300
cctttataat gggagggtct atctcacagg gaactcctgg cacttacttg tcttctcata    3360
atcaggctta tccacaagaa gcccctaagc cctccgtggg gtctatctct ctgggattgc    3420
cccggcagca ggagtctacc aaagcagctc ctttgaccta catcaagcag aagaatttt    3480 ctccgagaag ccaaaactca aacctgaggg gtttattggt cagagcgcag catgaaggtg    3540
tggtcagagg cactgcaggg gctgtccaag aaggaagtat aactcgggga actccagcca    3600
gcaaaatctc agtggagacc atttcatcgt tgcggggctc tattacccag ggaccccag     3660 ctctgcccca ggctggaata ccaacagagg ctttggtgaa gggacctgtc tccaggatgc    3720
ctattgaaga aagcagtcct gagaaggtca gagaggaagc tgcatccaag gccatgtta    3780 tctatgaagg caaaagtgga catatcttat catatgataa tattaagaat gcccgagaag    3840
ggactcggag tccaagaaca gctcatgaaa tgagttaaa aagaagctat gaggcagtgg     3900
aaggaagtat aaagcaaggc atgtcgatga gggagtctcc tgtgtcagca cctttagagg    3960
gtctgatatg ccgagcatta cccaggggga gccctcattc tgacctcaaa gagaggactg    4020
tgctgtctgg ttccataatg cagggcacac caagagccac agcggaaagc tttgaggacg    4080
gccttaaata ccccaaacag ataaaaaggg agagccctcc catccgagca tttgaaggtg    4140
ccattaccaa aggaaaacca tacgatggta tcaccaccat caaagaaatg gggcgctcca    4200
tccatgaaat cccacggcaa gatattctaa ctcaggaaag ccggaaaact ccagaagtgg    4260
tccagagcac gaggccaata attgagggtt ccatttccca gggcacacca ataaaatttg    4320
acaacaactc aggtcaatca gctatcaaac acaatgtgaa gtccttaatc acaggcccta    4380
gcaaactacc ccgtggaatg ctggaaattg taccagagaa cataaaagta gtagaacggg    4440
gaaaatatga ggatgtgaaa gcaggcgagc cagtgcgagc ccggcacacg tcagtggtga    4500
gctctggccc ctccgttctc aggtctacac ttcacgaagc tcccaaagca cagctgagcc    4560
cgggactcta tgatgacagc agcgctcgca ggactcctgt gagctaccag aacaccatat    4620
ccagaggctc ccccatgatg aacagaactt ctgatgtttc ttccagcaag tctgccagtc    4680
atgaaaggaa atcaactctg acccaaccc aaagagaaag tataccagcc aagtctccag    4740 tgcccgggt ggatcccatc gtgagtcaca gcccatttga tcctcatcac aggagtagcg     4800
ctgcaggaga ggtttatcgg agccacctac ccacgcactt ggatccagct atgccctttc    4860
acagggcttt ggatcctgct gctgcttacc tgttacagag acagctttca ccaaccccag    4920
gatacccaag tcagtaccag ctctatgcaa tggagaatac aaggcagaca atcctcaacg    4980
attacattac ctcacagcag atgcaggtga atctgcgccc tgatgtcacc aggggactgt    5040
ccccacgaga gcagccactg ggctccctt acccagctac aagaggaatc attgacctga    5100
ccaatatgcc tccaacaatc ttagtgcctc atgcaggggg aacgagcacc cctcccatgg    5160
acaggatcac gtatattcct ggtacacagg ttactttccc tcccaggcca tataacgctg    5220
cttctctgtc tccaggacac ccaacacacc ttgcagcagc tgcaagtgct gagagggaac    5280
gagaacggga aagggagaag gagcgcgaac gtgagcgcga gcgtgagcgt gaacgtgaac    5340
```

```
gcgaaaggat cgctgctgct cccgctgacc tctacctacg accaggttca gaacagccag   5400
gccgccctgg cagccacgga tatgttcgct cccctccccc ttcagtaaga actcaggaga   5460
ccatcctgca acagagaccc agtgttttcc agggcaccaa tggaaccagt gtaatcacac   5520
ctttggaccc aactgctcag ctacgcatca tgccactgcc ttctgggggc ccttccataa   5580
gtcaaggcct gccagcctcc cgttacaaca ctgctgcgga tgccctggct gctcttgtgg   5640
atgctgcagc ttctgcaccc cagatggatg tttccaaaac aaaagagagt aagcatgaag   5700
ctgccaggtt agaagaaaat ttgagaagca ggtcagcagc agttagtgaa cagcagcagc   5760
tagagcagaa aaacctggag gtggagaaga gatctgttca gtgtgtgtgc acttcttcag   5820
cccttccaag tggcaaggcc cagcctcatg cctcagtagt gtattctgag gctgggaaag   5880
ataaagggcc tcctccaaaa tccagatatg aggaagagct aaggacccga gggaagacta   5940
ccattactgc agctaacttc atagacgtga tcatcacccg gcaaattgcc tcggacaagg   6000
atgcgaggga acgtggctct caaagttcag actcttctag tagcttgtct tctcacaggt   6060
atgaaacggc tagtgatgcc attgaggtga taagtcccgc cagctcacct gcaccacccc   6120
aggaaaagcc acaggcctat cagccagaca tggttaaggc aaatcaagca gaaaatgagt   6180
ccactcgaca gtatgaaggt ccactgcatc attatcggtc ccagcaggaa tcaccatctc   6240
cacagcaaca gccaccactg cccccatctt cccagtcaga gggaatggga caggtgccca   6300
ggacccatcg actgatcaca cttgctgacc acatctgtca aattatcaca caagattttg   6360
ctagaaatca agttccctcg caggcttcta cttctacatt ccaaacttca ccatctgctt   6420
tgtcatccac acctgtaaga actaaaacct caagccgcta cagcccagaa tcacagtctc   6480
agactgtctt gcatcccaga ccaggtccta gagtctctcc agaaaatctt gtggataaat   6540
cccggggaag caggcctgga aaatctccag agaggagtca tatcccatca gagccctatg   6600
agcccatctc cccaccccaa ggccctgctg tgcatgagaa gcaggacagc atgttgctct   6660
tgtcacagag gggagtggac cctgctgagc aaaggagtga ttctcgatca ccaggaagta   6720
taagctactt gccttcattc ttcaccaagc ttgaaagcac atcacccatg gttaaatcaa   6780
agaaacagga aattttcgt aagttgaact cttctggtgg aggtgactct gatatggcag   6840
ctgctcagcc aggaacagag atcttcaatc tgccagcagt taccacatca ggtgcagtga   6900
gctcaagaag ccattctttt gctgatcccg ccagtaacct tggtctagaa gacatcatca   6960
gaaaggctct catgggaagt tttgatgata agttgaaga tcatggtgtt gtcatgtccc   7020
atcctgtggg cattatgcct ggtagtgcca gcacctcagt ggtgacgagc agcgaggcac   7080
ggagagatga aggggagcca tcacctcatg caggagtatg caaaccaaag ctgatcaaca   7140
aatcaaacag caggaagtct aaatctccta ttcctgggca aagctattta ggaactgaaa   7200
ggccttcttc tgtctcctct gtgcattcag aaggtgatta ccacaggcag acaccaggat   7260
gggcatggga agatcggccc tcttcaacag gttctactca gttcccttac aaccctctga   7320
ccatacggat gctcagcagt acaccaccta cacagatcgc atgcgcccca tctgccatca   7380
cccaagcagc tccacatcaa cagaaccgca tctgggagag ggagcctgcc ccgctcctct   7440
cagcgcagta tgagacactg tctgatagtg acgactgagc tgtgctggga gagcgctctg   7500
gctttggttt ttattgaaga tttaaaaaaa aaaaaaaga aaattattct gccctcccat   7560
gatttgtgcc cagagacttc tcaggagagc caggccatgg atgaggaaga aatgatggaa   7620
attcatttgg aaaatcaaat gggaaaaaac aaacnaaaaa actgcctcta atacaggcac   7680
ttcaatggat tataacagtg gcgggttgaa gtgtagagtt tttttnangt ggacaattct   7740
```

-continued

```
tgttcttaca tctgtttgta aagaaaacca tgatgtcttt                          7780
```

<210> SEQ ID NO 3
<211> LENGTH: 2440
<212> TYPE: PRT
<213> ORGANISM: Homo sapiens

<400> SEQUENCE: 3

```
Met Ser Ser Ser Gly Tyr Pro Pro Asn Gln Gly Ala Phe Ser Thr Glu
 1               5                  10                  15
Gln Ser Arg Tyr Pro Pro His Ser Val Gln Tyr Thr Phe Pro Asn Thr
                20                  25                  30
Arg His Gln Gln Glu Phe Ala Val Pro Asp Tyr Arg Ser Ser His Leu
            35                  40                  45
Glu Val Ser Gln Ala Ser Gln Leu Leu Gln Gln Gln Gln Gln Gln Gln
        50                  55                  60
Leu Arg Arg Arg Pro Ser Leu Leu Ser Glu Phe His Pro Gly Ser Asp
65                  70                  75                  80
Arg Pro Gln Glu Arg Arg Thr Ser Tyr Glu Pro Phe His Pro Gly Pro
                85                  90                  95
Ser Pro Val Asp His Asp Ser Leu Glu Ser Lys Arg Pro Arg Leu Glu
            100                 105                 110
Gln Val Ser Asp Ser His Phe Gln Arg Val Ser Ala Ala Val Leu Pro
        115                 120                 125
Leu Val His Pro Leu Pro Glu Gly Leu Arg Ala Ser Ala Asp Ala Lys
    130                 135                 140
Lys Asp Pro Ala Phe Gly Gly Lys His Glu Ala Pro Ser Ser Pro Ile
145                 150                 155                 160
Ser Gly Gln Pro Cys Gly Asp Asp Gln Asn Ala Ser Pro Ser Lys Leu
                165                 170                 175
Ser Lys Glu Glu Leu Ile Gln Ser Met Asp Arg Val Asp Arg Glu Ile
            180                 185                 190
Ala Lys Val Glu Gln Gln Ile Leu Lys Leu Lys Lys Lys Gln Gln Gln
        195                 200                 205
Leu Glu Glu Glu Ala Ala Lys Pro Pro Glu Pro Glu Lys Pro Val Ser
    210                 215                 220
Pro Pro Pro Val Glu Gln Lys His Arg Ser Ile Val Gln Ile Ile Tyr
225                 230                 235                 240
Asp Glu Asn Arg Lys Lys Ala Glu Glu Ala His Lys Ile Phe Glu Gly
                245                 250                 255
Leu Gly Pro Lys Val Glu Leu Pro Leu Tyr Asn Gln Pro Ser Asp Thr
            260                 265                 270
Lys Val Tyr His Glu Asn Ile Lys Thr Asn Gln Val Met Arg Lys Lys
        275                 280                 285
Leu Ile Leu Phe Phe Lys Arg Arg Asn His Ala Arg Lys Gln Arg Glu
    290                 295                 300
Gln Lys Ile Cys Gln Arg Tyr Asp Gln Leu Met Glu Ala Trp Glu Lys
305                 310                 315                 320
Lys Val Asp Arg Ile Glu Asn Asn Pro Arg Arg Lys Ala Lys Glu Ser
                325                 330                 335
Lys Thr Arg Glu Tyr Tyr Glu Lys Gln Phe Pro Glu Ile Arg Lys Gln
            340                 345                 350
Arg Glu Gln Gln Glu Arg Phe Gln Arg Val Gly Gln Arg Gly Ala Gly
        355                 360                 365
```

```
Leu Ser Ala Thr Ile Ala Arg Ser Glu His Glu Ile Ser Glu Ile Ile
    370                 375                 380

Asp Gly Leu Ser Glu Gln Glu Asn Asn Glu Lys Gln Met Arg Gln Leu
385                 390                 395                 400

Ser Val Ile Pro Pro Met Met Phe Asp Ala Glu Gln Arg Arg Val Lys
                405                 410                 415

Phe Ile Asn Met Asn Gly Leu Met Glu Asp Pro Met Lys Val Tyr Lys
            420                 425                 430

Asp Arg Gln Phe Met Asn Val Trp Thr Asp His Glu Lys Glu Ile Phe
        435                 440                 445

Lys Asp Lys Phe Ile Gln His Pro Lys Asn Phe Gly Leu Ile Ala Ser
    450                 455                 460

Tyr Leu Glu Arg Lys Ser Val Pro Asp Cys Val Leu Tyr Tyr Tyr Leu
465                 470                 475                 480

Thr Lys Lys Asn Glu Asn Tyr Lys Ala Leu Val Arg Arg Asn Tyr Gly
                485                 490                 495

Lys Arg Arg Gly Arg Asn Gln Gln Ile Ala Arg Pro Ser Gln Glu Glu
            500                 505                 510

Lys Val Glu Glu Lys Glu Asp Lys Ala Glu Lys Thr Glu Lys Lys
        515                 520                 525

Glu Glu Glu Lys Lys Asp Glu Glu Lys Asp Glu Lys Glu Asp Ser
    530                 535                 540

Lys Glu Asn Thr Lys Glu Lys Asp Lys Ile Asp Gly Thr Ala Glu Glu
545                 550                 555                 560

Thr Glu Glu Arg Glu Gln Ala Thr Pro Arg Gly Arg Lys Thr Ala Asn
                565                 570                 575

Ser Gln Gly Arg Arg Lys Gly Arg Ile Thr Arg Ser Met Thr Asn Glu
            580                 585                 590

Ala Ala Ala Ala Ser Ala Ala Ala Ala Ala Thr Glu Glu Pro Pro
        595                 600                 605

Pro Pro Leu Pro Pro Pro Glu Pro Ile Ser Thr Glu Pro Val Glu
    610                 615                 620

Thr Ser Arg Trp Thr Glu Glu Glu Met Glu Val Ala Lys Lys Gly Leu
625                 630                 635                 640

Val Glu His Gly Arg Asn Trp Ala Ala Ile Ala Lys Met Val Gly Thr
                645                 650                 655

Lys Ser Glu Ala Gln Cys Lys Asn Phe Tyr Phe Asn Tyr Lys Arg Arg
            660                 665                 670

His Asn Leu Asp Asn Leu Leu Gln Gln His Lys Gln Lys Thr Ser Arg
        675                 680                 685

Lys Pro Arg Glu Glu Arg Asp Val Ser Gln Cys Glu Ser Val Ala Ser
    690                 695                 700

Thr Val Ser Ala Gln Glu Asp Glu Asp Ile Glu Ala Ser Asn Glu Glu
705                 710                 715                 720

Glu Asn Pro Glu Asp Ser Glu Val Glu Ala Val Lys Pro Ser Glu Asp
                725                 730                 735

Ser Pro Glu Asn Ala Thr Ser Arg Gly Asn Thr Glu Pro Ala Val Glu
            740                 745                 750

Leu Glu Pro Thr Thr Glu Thr Ala Pro Ser Thr Pro Ser Leu Ala
        755                 760                 765

Val Pro Ser Thr Lys Pro Ala Glu Asp Glu Ser Val Glu Thr Gln Val
770                 775                 780
```

-continued

```
Asn Asp Ser Ile Ser Ala Glu Thr Ala Glu Gln Met Asp Val Asp Gln
785                 790                 795                 800

Gln Glu His Ser Ala Glu Gly Ser Val Cys Asp Pro Pro Ala
            805                 810                 815

Thr Lys Ala Asp Ser Val Asp Val Glu Val Arg Val Pro Glu Asn His
            820                 825                 830

Ala Ser Lys Val Glu Gly Asp Asn Thr Lys Glu Arg Asp Leu Asp Arg
            835                 840                 845

Ala Ser Glu Lys Val Glu Pro Arg Asp Glu Asp Leu Val Val Ala Gln
            850                 855                 860

Gln Ile Asn Ala Gln Arg Pro Glu Pro Gln Ser Asp Asn Asp Ser Ser
865                 870                 875                 880

Ala Thr Cys Ser Ala Asp Glu Asp Val Asp Gly Glu Pro Glu Arg Gln
            885                 890                 895

Arg Met Phe Pro Met Asp Ser Lys Pro Ser Leu Leu Asn Pro Thr Gly
            900                 905                 910

Ser Ile Leu Val Ser Ser Pro Leu Lys Pro Asn Pro Leu Asp Leu Pro
            915                 920                 925

Gln Leu Gln His Arg Ala Ala Val Ile Pro Pro Met Val Ser Cys Thr
930                 935                 940

Pro Cys Asn Ile Pro Ile Gly Thr Pro Val Ser Gly Tyr Ala Leu Tyr
945                 950                 955                 960

Gln Arg His Ile Lys Ala Met His Glu Ser Ala Leu Leu Glu Glu Gln
            965                 970                 975

Arg Gln Arg Gln Glu Gln Ile Asp Leu Glu Cys Arg Ser Ser Thr Ser
            980                 985                 990

Pro Cys Gly Thr Ser Lys Ser Pro Asn Arg Glu Trp Glu Val Leu Gln
            995                 1000                1005

Pro Ala Pro His Gln Leu Ile Thr Asn Leu Pro Glu Gly Val Arg Leu
            1010                1015                1020

Pro Thr Thr Arg Pro Thr Arg Pro Pro Pro Leu Ile Pro Ser Ser
1025                1030                1035                1040

Lys Thr Thr Val Ala Ser Glu Lys Pro Ser Phe Ile Met Gly Gly Ser
            1045                1050                1055

Ile Ser Gln Gly Thr Pro Gly Thr Tyr Leu Thr Ser His Asn Gln Ala
            1060                1065                1070

Ser Tyr Thr Gln Glu Thr Pro Lys Pro Ser Val Gly Ser Ile Ser Leu
            1075                1080                1085

Gly Leu Pro Arg Gln Gln Glu Ser Ala Lys Ser Ala Thr Leu Pro Tyr
            1090                1095                1100

Ile Lys Gln Glu Glu Phe Ser Pro Arg Ser Gln Asn Ser Gln Pro Glu
1105                1110                1115                1120

Gly Leu Leu Val Arg Ala Gln His Glu Gly Val Val Arg Gly Thr Ala
            1125                1130                1135

Gly Ala Ile Gln Glu Gly Ser Ile Thr Arg Gly Thr Pro Thr Ser Lys
            1140                1145                1150

Ile Ser Val Glu Ser Ile Pro Ser Leu Arg Gly Ser Ile Thr Gln Gly
            1155                1160                1165

Thr Pro Ala Leu Pro Gln Thr Gly Ile Pro Thr Glu Ala Leu Val Lys
            1170                1175                1180

Gly Ser Ile Ser Arg Met Pro Ile Glu Asp Ser Ser Pro Glu Lys Gly
1185                1190                1195                1200

Arg Glu Glu Ala Ala Ser Lys Gly His Val Ile Tyr Glu Gly Lys Ser
```

-continued

```
                 1205                1210                1215
Gly His Ile Leu Ser Tyr Asp Asn Ile Lys Asn Ala Arg Glu Gly Thr
            1220                1225                1230
Arg Ser Pro Arg Thr Ala His Glu Ile Ser Leu Lys Arg Ser Tyr Glu
            1235                1240                1245
Ser Val Glu Gly Asn Ile Lys Gln Gly Met Ser Met Arg Glu Ser Pro
            1250                1255                1260
Val Ser Ala Pro Leu Glu Gly Leu Ile Cys Arg Ala Leu Pro Arg Gly
1265                1270                1275                1280
Ser Pro His Ser Asp Leu Lys Glu Arg Thr Val Leu Ser Gly Ser Ile
            1285                1290                1295
Met Gln Gly Thr Pro Arg Ala Thr Thr Glu Ser Phe Glu Asp Gly Leu
            1300                1305                1310
Lys Tyr Pro Lys Gln Ile Lys Arg Glu Ser Pro Pro Ile Arg Ala Phe
            1315                1320                1325
Glu Gly Ala Ile Thr Lys Gly Lys Pro Tyr Asp Gly Ile Thr Thr Ile
            1330                1335                1340
Lys Glu Met Gly Arg Ser Ile His Glu Ile Pro Arg Gln Asp Ile Leu
1345                1350                1355                1360
Thr Gln Glu Ser Arg Lys Thr Pro Glu Val Val Gln Ser Thr Arg Pro
            1365                1370                1375
Ile Ile Glu Gly Ser Ile Ser Gln Gly Thr Pro Ile Lys Phe Asp Asn
            1380                1385                1390
Asn Ser Gly Gln Ser Ala Ile Lys His Asn Val Lys Ser Leu Ile Thr
            1395                1400                1405
Gly Pro Ser Lys Leu Ser Arg Gly Met Pro Pro Leu Glu Ile Val Pro
            1410                1415                1420
Glu Asn Ile Lys Val Val Glu Arg Gly Lys Tyr Glu Asp Val Lys Ala
1425                1430                1435                1440
Gly Glu Thr Val Arg Ser Arg His Thr Ser Val Val Ser Ser Gly Pro
            1445                1450                1455
Ser Val Leu Arg Ser Thr Leu His Glu Ala Pro Lys Ala Gln Leu Ser
            1460                1465                1470
Pro Gly Ile Tyr Asp Asp Thr Ser Ala Arg Arg Thr Pro Val Ser Tyr
            1475                1480                1485
Gln Asn Thr Met Ser Arg Gly Ser Pro Met Met Asn Arg Thr Ser Asp
            1490                1495                1500
Val Thr Ile Pro Pro Asn Lys Ser Thr Asn His Glu Arg Lys Ser Thr
1505                1510                1515                1520
Leu Thr Pro Thr Gln Arg Glu Ser Ile Pro Ala Lys Ser Pro Val Pro
            1525                1530                1535
Gly Val Asp Pro Val Val Ser His Ser Pro Phe Asp Pro His His Arg
            1540                1545                1550
Gly Ser Thr Ala Gly Glu Val Tyr Trp Ser His Leu Pro Thr Gln Leu
            1555                1560                1565
Asp Pro Ala Met Pro Phe His Arg Ala Leu Asp Pro Ala Ala Ala
            1570                1575                1580
Tyr Leu Phe Gln Arg Gln Leu Ser Pro Thr Pro Gly Tyr Pro Ser Gln
1585                1590                1595                1600
Tyr Gln Leu Tyr Ala Met Glu Asn Thr Arg Gln Thr Ile Leu Asn Asp
            1605                1610                1615
Tyr Ile Thr Ser Gln Gln Met Gln Val Asn Leu Arg Pro Asp Val Ala
            1620                1625                1630
```

```
Arg Gly Leu Ser Pro Arg Glu Gln Pro Leu Gly Leu Pro Tyr Pro Ala
        1635                1640                1645

Thr Arg Gly Ile Ile Asp Leu Thr Asn Met Pro Pro Thr Ile Leu Val
1650                1655                1660

Pro His Pro Gly Gly Thr Ser Thr Pro Pro Met Asp Arg Ile Thr Tyr
1665                1670                1675                1680

Ile Pro Gly Thr Gln Ile Thr Phe Pro Pro Arg Pro Tyr Asn Ser Ala
        1685                1690                1695

Ser Met Ser Pro Gly His Pro Thr His Leu Ala Ala Ala Ser Ala
                1700                1705                1710

Glu Arg Glu Arg Glu Arg Glu Lys Glu Arg Glu Arg Glu Arg
        1715                1720                1725

Ile Ala Ala Ser Ser Asp Leu Tyr Leu Arg Pro Gly Ser Glu Gln
        1730                1735                1740

Pro Gly Arg Pro Gly Ser His Gly Tyr Val Arg Ser Pro Ser Pro Ser
1745                1750                1755                1760

Val Arg Thr Gln Glu Thr Met Leu Gln Gln Arg Pro Ser Val Phe Gln
                1765                1770                1775

Gly Thr Asn Gly Thr Ser Val Ile Thr Pro Leu Asp Pro Thr Ala Gln
        1780                1785                1790

Leu Arg Ile Met Pro Leu Pro Ala Gly Gly Pro Ser Ile Ser Gln Gly
        1795                1800                1805

Leu Pro Ala Ser Arg Tyr Asn Thr Ala Ala Asp Ala Leu Ala Ala Leu
        1810                1815                1820

Val Asp Ala Ala Ala Ser Ala Pro Gln Met Asp Val Ser Lys Thr Lys
1825                1830                1835                1840

Glu Ser Lys His Glu Ala Ala Arg Leu Glu Glu Asn Leu Arg Ser Arg
                1845                1850                1855

Ser Ala Ala Val Ser Glu Gln Gln Gln Leu Glu Gln Lys Thr Leu Glu
        1860                1865                1870

Val Glu Lys Arg Ser Val Gln Cys Leu Tyr Thr Ser Ser Ala Phe Pro
        1875                1880                1885

Ser Gly Lys Pro Gln Pro His Ser Ser Val Val Tyr Ser Glu Ala Gly
        1890                1895                1900

Lys Asp Lys Gly Pro Pro Lys Ser Arg Tyr Glu Glu Leu Arg
1905                1910                1915                1920

Thr Arg Gly Lys Thr Thr Ile Thr Ala Ala Asn Phe Ile Asp Val Ile
        1925                1930                1935

Ile Thr Arg Gln Ile Ala Ser Asp Lys Asp Ala Arg Glu Arg Gly Ser
        1940                1945                1950

Gln Ser Ser Asp Ser Ser Ser Leu Ser Ser His Arg Tyr Glu Thr
        1955                1960                1965

Pro Ser Asp Ala Ile Glu Val Ile Ser Pro Ala Ser Ser Pro Ala Pro
        1970                1975                1980

Pro Gln Glu Lys Leu Gln Thr Tyr Gln Pro Glu Val Val Lys Ala Asn
1985                1990                1995                2000

Gln Ala Glu Asn Asp Pro Thr Arg Gln Tyr Glu Gly Pro Leu His His
                2005                2010                2015

Tyr Arg Pro Gln Gln Glu Ser Pro Ser Pro Gln Gln Leu Pro Pro
        2020                2025                2030

Ser Ser Gln Ala Glu Gly Met Gly Gln Val Pro Arg Thr His Arg Leu
        2035                2040                2045
```

```
Ile Thr Leu Ala Asp His Ile Cys Gln Ile Ile Thr Gln Asp Phe Ala
    2050                2055                2060

Arg Asn Gln Val Ser Ser Gln Thr Pro Gln Gln Pro Pro Thr Ser Thr
2065                2070                2075                2080

Phe Gln Asn Ser Pro Ser Ala Leu Val Ser Thr Pro Val Arg Thr Lys
                2085                2090                2095

Thr Ser Asn Arg Tyr Ser Pro Glu Ser Gln Ala Gln Ser Val His His
            2100                2105                2110

Gln Arg Pro Gly Ser Arg Val Ser Pro Glu Asn Leu Val Asp Lys Ser
        2115                2120                2125

Arg Gly Ser Arg Pro Gly Lys Ser Pro Glu Arg Ser His Val Ser Ser
    2130                2135                2140

Glu Pro Tyr Glu Pro Ile Ser Pro Pro Gln Val Pro Val His Glu
2145                2150                2155                2160

Lys Gln Asp Ser Leu Leu Leu Leu Ser Gln Arg Gly Ala Glu Pro Ala
                2165                2170                2175

Glu Gln Arg Asn Asp Ala Arg Ser Pro Gly Ser Ile Ser Tyr Leu Pro
            2180                2185                2190

Ser Phe Phe Thr Lys Leu Glu Asn Thr Ser Pro Met Val Lys Ser Lys
        2195                2200                2205

Lys Gln Glu Ile Phe Arg Lys Leu Asn Ser Ser Gly Gly Gly Asp Ser
    2210                2215                2220

Asp Met Ala Ala Ala Gln Pro Gly Thr Glu Ile Phe Asn Leu Pro Ala
2225                2230                2235                2240

Val Thr Thr Ser Gly Ser Val Ser Ser Arg Gly His Ser Phe Ala Asp
                2245                2250                2255

Pro Ala Ser Asn Leu Gly Leu Glu Asp Ile Ile Arg Lys Ala Leu Met
            2260                2265                2270

Gly Ser Phe Asp Asp Lys Val Glu Asp His Gly Val Val Met Ser Gln
        2275                2280                2285

Pro Met Gly Val Val Pro Gly Thr Ala Asn Thr Ser Val Val Thr Ser
    2290                2295                2300

Gly Glu Thr Arg Arg Glu Gly Asp Pro Ser Pro His Ser Gly Gly
2305                2310                2315                2320

Val Cys Lys Pro Lys Leu Ile Ser Lys Ser Asn Ser Arg Lys Ser Lys
                2325                2330                2335

Ser Pro Ile Pro Gly Gln Gly Tyr Leu Gly Thr Glu Arg Pro Ser Ser
            2340                2345                2350

Val Ser Ser Val His Ser Glu Gly Asp Tyr His Arg Gln Thr Pro Gly
        2355                2360                2365

Trp Ala Trp Glu Asp Arg Pro Ser Ser Thr Gly Ser Thr Gln Phe Pro
    2370                2375                2380

Tyr Asn Pro Leu Thr Met Arg Met Leu Ser Ser Thr Pro Pro Thr Pro
2385                2390                2395                2400

Ile Ala Cys Ala Pro Ser Ala Val Asn Gln Ala Ala Pro His Gln Gln
                2405                2410                2415

Asn Arg Ile Trp Glu Arg Glu Pro Ala Pro Leu Leu Ser Ala Gln Tyr
            2420                2425                2430

Glu Thr Leu Ser Asp Ser Asp
        2435                2440

<210> SEQ ID NO 4
<211> LENGTH: 2453
<212> TYPE: PRT
```

<213> ORGANISM: Mus musculus

<400> SEQUENCE: 4

```
Met Ser Ser Ser Gly Tyr Pro Pro Asn Gln Gly Ala Phe Ser Thr Glu
1               5                   10                  15

Gln Ser Arg Tyr Pro Ser His Ser Val Gln Tyr Thr Phe Pro Ser Ala
            20                  25                  30

Arg His Gln Gln Glu Phe Ala Val Pro Asp Tyr Arg Ser Ser His Leu
        35                  40                  45

Glu Val Ser Gln Ala Ser Gln Leu Leu Gln Gln Gln Gln Gln Gln Gln
50                  55                  60

Leu Arg Arg Arg Pro Ser Leu Leu Ser Glu Phe His Pro Gly Ser Asp
65                  70                  75                  80

Arg Pro Gln Glu Arg Arg Ser Gly Tyr Glu Gln Phe His Pro Gly Pro
                85                  90                  95

Ser Pro Val Asp His Asp Ser Leu Glu Ser Lys Arg Pro Arg Leu Glu
            100                 105                 110

Gln Val Ser Asp Ser His Phe Gln Arg Ile Ser Ala Ala Val Leu Pro
        115                 120                 125

Leu Val His Thr Leu Pro Glu Gly Leu Arg Ser Ser Ala Asn Ala Lys
130                 135                 140

Lys Asp Pro Ala Phe Gly Val Lys His Glu Ala Pro Ser Ser Pro Leu
145                 150                 155                 160

Ser Gly Gln Pro Cys Gly Asp Asp Gln Asn Ala Ser Pro Ser Lys Leu
                165                 170                 175

Ser Lys Glu Glu Leu Ile Gln Ser Met Asp Arg Val Asp Arg Glu Ile
            180                 185                 190

Ala Lys Val Glu Gln Gln Ile Leu Lys Leu Lys Lys Lys Gln Gln Gln
        195                 200                 205

Leu Glu Glu Glu Ala Ala Lys Pro Pro Glu Pro Glu Lys Pro Val Ser
210                 215                 220

Pro Pro Pro Val Glu Gln Lys His Arg Ser Ile Val Gln Ile Ile Tyr
225                 230                 235                 240

Asp Glu Asn Arg Lys Lys Ala Glu Glu Ala His Lys Ile Phe Glu Gly
                245                 250                 255

Leu Gly Pro Lys Val Glu Leu Pro Leu Tyr Asn Gln Pro Ser Asp Thr
            260                 265                 270

Lys Val Tyr His Glu Asn Ile Lys Thr Asn Gln Val Met Arg Lys Lys
        275                 280                 285

Leu Ile Leu Phe Phe Lys Arg Arg Asn His Ala Arg Lys Gln Arg Glu
290                 295                 300

Gln Lys Ile Cys Gln Arg Tyr Asp Gln Leu Met Glu Ala Trp Glu Lys
305                 310                 315                 320

Lys Val Asp Arg Ile Glu Asn Asn Pro Arg Arg Lys Ala Lys Glu Ser
                325                 330                 335

Lys Thr Arg Glu Tyr Tyr Glu Lys Gln Phe Pro Glu Ile Arg Lys Gln
            340                 345                 350

Arg Glu Gln Gln Glu Arg Phe Gln Arg Val Gly Gln Arg Gly Ala Gly
        355                 360                 365

Leu Ser Ala Thr Ile Ala Arg Ser Glu His Glu Ile Ser Glu Ile Ile
370                 375                 380

Asp Gly Leu Ser Glu Gln Glu Asn Asn Glu Lys Gln Met Arg Gln Leu
385                 390                 395                 400
```

-continued

```
Ser Val Ile Pro Pro Met Met Phe Asp Ala Glu Gln Arg Arg Val Lys
                405                 410                 415

Phe Ile Asn Met Asn Gly Leu Met Glu Asp Pro Met Lys Val Tyr Lys
            420                 425                 430

Asp Arg Gln Phe Met Asn Val Trp Thr Asp His Glu Lys Glu Ile Phe
        435                 440                 445

Lys Asp Lys Phe Ile Gln His Pro Lys Asn Phe Gly Leu Ile Ala Ser
450                 455                 460

Tyr Leu Glu Arg Lys Ser Val Pro Asp Cys Val Leu Tyr Tyr Tyr Leu
465                 470                 475                 480

Thr Lys Lys Asn Glu Asn Tyr Lys Ala Leu Val Arg Arg Asn Tyr Gly
                485                 490                 495

Lys Arg Arg Gly Arg Asn Gln Gln Ile Ala Arg Pro Ser Gln Glu Glu
            500                 505                 510

Lys Val Glu Glu Lys Glu Glu Asp Lys Ala Glu Lys Thr Glu Lys Lys
        515                 520                 525

Glu Glu Glu Lys Lys Asp Asp Glu Glu Lys Asp Asp Lys Glu Asp Ser
    530                 535                 540

Lys Glu Thr Thr Lys Glu Lys Asp Arg Thr Glu Ala Thr Ala Glu Glu
545                 550                 555                 560

Pro Glu Glu Arg Glu Gln Val Thr Pro Arg Gly Arg Lys Thr Ala Asn
                565                 570                 575

Ser Gln Gly Arg Gly Lys Gly Arg Val Thr Arg Ser Met Thr Ser Glu
            580                 585                 590

Ala Ala Ala Ala Asn Ala Ala Ala Ala Thr Glu Glu Pro Pro
        595                 600                 605

Pro Leu Pro Pro Pro Glu Pro Ile Ser Thr Glu Pro Val Glu Thr
    610                 615                 620

Ser Arg Trp Thr Glu Glu Glu Met Glu Val Ala Lys Lys Gly Leu Val
625                 630                 635                 640

Glu His Gly Arg Asn Trp Ala Ala Ile Ala Lys Met Val Gly Thr Lys
                645                 650                 655

Ser Glu Ala Gln Cys Lys Asn Phe Tyr Phe Asn Tyr Lys Arg Arg His
            660                 665                 670

Asn Leu Asp Asn Leu Leu Gln Gln His Lys Gln Lys Ala Ser Arg Lys
        675                 680                 685

Pro Arg Glu Glu Arg Asp Val Ser Gln Cys Glu Ser Val Ala Ser Thr
    690                 695                 700

Val Ser Ala Gln Glu Asp Glu Asp Ile Glu Ala Ser Asn Glu Glu Glu
705                 710                 715                 720

Asn Pro Glu Asp Ser Glu Gly Ala Glu Asn Ser Ser Asp Thr Glu Ser
                725                 730                 735

Ala Pro Ser Pro Ser Pro Val Glu Ala Ala Lys Ser Ser Glu Asp Ser
            740                 745                 750

Ser Glu Asn Ala Ala Ser Arg Gly Asn Thr Glu Pro Val Ala Glu Leu
        755                 760                 765

Glu Ala Thr Thr Asp Pro Ala Pro Cys Ala Ser Pro Ser Ser Ala Val
    770                 775                 780

Pro Thr Thr Lys Pro Ala Glu Arg Glu Ser Val Glu Ala Gln Val Thr
785                 790                 795                 800

Asp Ser Ala Ser Ala Glu Thr Ala Glu Pro Met Asp Val Asp His Glu
                805                 810                 815

Glu Cys Gly Ala Glu Gly Ser Ser Val Leu Asp Pro Pro Ala Pro Thr
```

-continued

```
                820             825             830
Lys Ala Asp Ser Val Asp Pro Glu Met Gln Val Pro Glu Asn Thr Ala
        835                 840                 845
Ser Lys Gly Glu Gly Asp Ala Lys Glu Arg Asp Leu Glu Ser Thr Ser
        850                 855                 860
Glu Lys Thr Glu Ala Arg Asp Glu Asp Val Val Ala Glu Gln Ile
865                 870                 875                 880
Glu Arg Pro Glu Pro Gln Ser Asp Asp Ser Ser Ala Thr Cys Ser
                885                 890                 895
Ala Asp Glu Gly Val Asp Gly Glu Pro Glu Arg Gln Arg Val Phe Pro
        900                 905                 910
Met Asp Ala Lys Pro Ser Leu Leu Thr Pro Pro Gly Ser Ile Leu Ile
        915                 920                 925
Ser Ser Pro Ile Lys Pro Asn Leu Leu Asp Leu Pro Gln Leu Gln His
        930                 935                 940
Arg Ala Ala Val Ile Pro Pro Met Val Ser Cys Thr Pro Cys Asn Ile
945                 950                 955                 960
Pro Ile Gly Thr Pro Val Ser Gly Tyr Ala Leu Tyr Gln Arg His Ile
                965                 970                 975
Lys Ala Met His Glu Ser Ala Leu Leu Glu Glu Gln Arg Gln Arg Gln
                980                 985                 990
Glu Gln Val Asp Leu Glu Cys Arg Ser Ser Thr Ser Pro Cys Ser Thr
        995                 1000                1005
Ser Lys Ser Pro Asn Arg Glu Trp Glu Val Leu Gln Pro Ala Pro His
        1010                1015                1020
Gln Val Ile Thr Asn Leu Pro Glu Gly Val Arg Leu Pro Thr Thr Arg
1025                1030                1035                1040
Pro Thr Arg Pro Pro Pro Leu Ile Pro Ser Ser Lys Thr Thr Val
                1045                1050                1055
Ala Ser Glu Lys Pro Ser Phe Ile Met Gly Gly Ser Ile Ser Gln Gly
                1060                1065                1070
Thr Pro Gly Thr Tyr Leu Ser Ser His Asn Gln Ala Tyr Pro Gln Glu
        1075                1080                1085
Ala Pro Lys Pro Ser Val Gly Ser Ile Ser Leu Gly Leu Pro Arg Gln
        1090                1095                1100
Gln Glu Ser Thr Lys Ala Ala Pro Leu Thr Tyr Ile Lys Gln Glu Glu
1105                1110                1115                1120
Phe Ser Pro Arg Ser Gln Asn Ser Gln Pro Gly Leu Leu Val Arg
                1125                1130                1135
Ala Gln His Glu Gly Val Val Arg Gly Thr Ala Gly Ala Val Gln Glu
        1140                1145                1150
Gly Ser Ile Thr Arg Gly Thr Pro Ala Ser Lys Ile Ser Val Glu Thr
        1155                1160                1165
Ile Ser Ser Leu Arg Gly Ser Ile Thr Gln Gly Thr Pro Ala Leu Pro
        1170                1175                1180
Gln Ala Gly Ile Pro Thr Glu Ala Leu Val Lys Gly Pro Val Ser Arg
1185                1190                1195                1200
Met Pro Ile Glu Glu Ser Ser Pro Glu Lys Val Arg Glu Glu Ala Ala
                1205                1210                1215
Ser Lys Gly His Val Ile Tyr Glu Gly Lys Ser Gly His Ile Leu Ser
                1220                1225                1230
Tyr Asp Asn Ile Lys Asn Ala Arg Glu Gly Thr Arg Ser Pro Arg Thr
        1235                1240                1245
```

```
Ala His Glu Met Ser Leu Lys Arg Ser Tyr Glu Ala Val Glu Gly Ser
    1250                1255                1260
Ile Lys Gln Gly Met Ser Met Arg Glu Ser Pro Val Ser Ala Pro Leu
1265            1270                1275                1280
Glu Gly Leu Ile Cys Arg Ala Leu Pro Arg Gly Ser Pro His Ser Asp
                1285                1290                1295
Leu Lys Glu Arg Thr Val Leu Ser Gly Ser Ile Met Gln Gly Thr Pro
                    1300                1305                1310
Arg Ala Thr Ala Glu Ser Phe Glu Asp Gly Leu Lys Tyr Pro Lys Gln
                1315                1320                1325
Ile Lys Arg Glu Ser Pro Pro Ile Arg Ala Phe Glu Gly Ala Ile Thr
            1330                1335                1340
Lys Gly Lys Pro Tyr Asp Gly Ile Thr Thr Ile Lys Glu Met Gly Arg
1345                1350                1355                1360
Ser Ile His Glu Ile Pro Arg Gln Asp Ile Leu Thr Gln Glu Ser Arg
                1365                1370                1375
Lys Thr Pro Glu Val Val Gln Ser Thr Arg Pro Ile Ile Glu Gly Ser
                1380                1385                1390
Ile Ser Gln Gly Thr Pro Ile Lys Phe Asp Asn Asn Ser Gly Gln Ser
            1395                1400                1405
Ala Ile Lys His Asn Val Lys Ser Leu Ile Thr Gly Pro Ser Lys Leu
        1410                1415                1420
Pro Arg Gly Met Leu Glu Ile Val Pro Glu Asn Ile Lys Val Val Glu
1425                1430                1435                1440
Arg Gly Lys Tyr Glu Asp Val Lys Ala Gly Glu Pro Val Arg Ala Arg
                1445                1450                1455
His Thr Ser Val Val Ser Ser Gly Pro Ser Val Leu Arg Ser Thr Leu
                    1460                1465                1470
His Glu Ala Pro Lys Ala Gln Leu Ser Pro Gly Leu Tyr Asp Asp Ser
                1475                1480                1485
Ser Ala Arg Arg Thr Pro Val Ser Tyr Gln Asn Thr Ile Ser Arg Gly
        1490                1495                1500
Ser Pro Met Met Asn Arg Thr Ser Asp Val Ser Ser Ser Lys Ser Ala
1505                1510                1515                1520
Ser His Glu Arg Lys Ser Thr Leu Thr Pro Thr Gln Arg Glu Ser Ile
                1525                1530                1535
Pro Ala Lys Ser Pro Val Pro Gly Val Asp Pro Ile Val Ser His Ser
                1540                1545                1550
Pro Phe Asp Pro His His Arg Ser Ser Ala Ala Gly Glu Val Tyr Arg
            1555                1560                1565
Ser His Leu Pro Thr His Leu Asp Pro Ala Met Pro Phe His Arg Ala
        1570                1575                1580
Leu Asp Pro Ala Ala Ala Tyr Leu Leu Gln Arg Gln Leu Ser Pro Thr
1585                1590                1595                1600
Pro Gly Tyr Pro Ser Gln Tyr Gln Leu Tyr Ala Met Glu Asn Thr Arg
                1605                1610                1615
Gln Thr Ile Leu Asn Asp Tyr Ile Thr Ser Gln Gln Met Gln Val Asn
                1620                1625                1630
Leu Arg Pro Asp Val Thr Arg Gly Leu Ser Pro Arg Glu Gln Pro Leu
            1635                1640                1645
Gly Leu Pro Tyr Pro Ala Thr Arg Gly Ile Ile Asp Leu Thr Asn Met
    1650                1655                1660
```

-continued

```
Pro Pro Thr Ile Leu Val Pro His Ala Gly Thr Ser Thr Pro Pro
1665                1670                1675                1680

Met Asp Arg Ile Thr Tyr Ile Pro Gly Thr Gln Val Thr Phe Pro Pro
            1685                1690                1695

Arg Pro Tyr Asn Ala Ala Ser Leu Ser Pro Gly His Pro Thr His Leu
        1700                1705                1710

Ala Ala Ala Ala Ser Ala Glu Arg Glu Arg Glu Arg Glu Arg Glu Lys
        1715                1720                1725

Glu Arg Glu Arg Glu Arg Glu Arg Glu Arg Glu Arg Glu Arg Glu Arg
    1730                1735                1740

Ile Ala Ala Ala Pro Ala Asp Leu Tyr Leu Arg Pro Gly Ser Glu Gln
1745                1750                1755                1760

Pro Gly Arg Pro Gly Ser His Gly Tyr Val Arg Ser Pro Ser Pro Ser
            1765                1770                1775

Val Arg Thr Gln Glu Thr Ile Leu Gln Gln Arg Pro Ser Val Phe Gln
            1780                1785                1790

Gly Thr Asn Gly Thr Ser Val Ile Thr Pro Leu Asp Pro Thr Ala Gln
        1795                1800                1805

Leu Arg Ile Met Pro Leu Pro Ser Gly Gly Pro Ser Ile Ser Gln Gly
    1810                1815                1820

Leu Pro Ala Ser Arg Tyr Asn Thr Ala Ala Asp Ala Leu Ala Ala Leu
1825                1830                1835                1840

Val Asp Ala Ala Ala Ser Ala Pro Gln Met Asp Val Ser Lys Thr Lys
            1845                1850                1855

Glu Ser Lys His Glu Ala Ala Arg Leu Glu Glu Asn Leu Arg Ser Arg
        1860                1865                1870

Ser Ala Ala Val Ser Glu Gln Gln Gln Leu Glu Gln Lys Asn Leu Glu
        1875                1880                1885

Val Glu Lys Arg Ser Val Gln Cys Val Cys Thr Ser Ser Ala Leu Pro
    1890                1895                1900

Ser Gly Lys Ala Gln Pro His Ala Ser Val Val Tyr Ser Glu Ala Gly
1905                1910                1915                1920

Lys Asp Lys Gly Pro Pro Lys Ser Arg Tyr Glu Glu Glu Leu Arg
            1925                1930                1935

Thr Arg Gly Lys Thr Thr Ile Thr Ala Ala Asn Phe Ile Asp Val Ile
        1940                1945                1950

Ile Thr Arg Gln Ile Ala Ser Asp Lys Asp Ala Arg Glu Arg Gly Ser
    1955                1960                1965

Gln Ser Ser Asp Ser Ser Ser Leu Ser Ser His Arg Tyr Glu Thr
        1970                1975                1980

Ala Ser Asp Ala Ile Glu Val Ile Ser Pro Ala Ser Ser Pro Ala Pro
1985                1990                1995                2000

Pro Gln Glu Lys Pro Gln Ala Tyr Gln Pro Asp Met Val Lys Ala Asn
            2005                2010                2015

Gln Ala Glu Asn Glu Ser Thr Arg Gln Tyr Glu Gly Pro Leu His His
        2020                2025                2030

Tyr Arg Ser Gln Gln Glu Ser Pro Ser Pro Gln Gln Pro Pro Leu
        2035                2040                2045

Pro Pro Ser Ser Gln Ser Glu Gly Met Gly Gln Val Pro Arg Thr His
    2050                2055                2060

Arg Leu Ile Thr Leu Ala Asp His Ile Cys Gln Ile Ile Thr Gln Asp
2065                2070                2075                2080

Phe Ala Arg Asn Gln Val Pro Ser Gln Ala Ser Thr Ser Thr Phe Gln
```

```
                       2085                2090                2095
Thr Ser Pro Ser Ala Leu Ser Ser Thr Pro Val Arg Thr Lys Thr Ser
            2100                2105                2110
Ser Arg Tyr Ser Pro Glu Ser Gln Ser Gln Thr Val Leu His Pro Arg
            2115                2120                2125
Pro Gly Pro Arg Val Ser Pro Glu Asn Leu Val Asp Lys Ser Arg Gly
            2130                2135                2140
Ser Arg Pro Gly Lys Ser Pro Glu Arg Ser His Ile Pro Ser Glu Pro
2145                2150                2155                2160
Tyr Glu Pro Ile Ser Pro Pro Gln Gly Pro Ala Val His Glu Lys Gln
            2165                2170                2175
Asp Ser Met Leu Leu Leu Ser Gln Arg Gly Val Asp Pro Ala Glu Gln
            2180                2185                2190
Arg Ser Asp Ser Arg Ser Pro Gly Ser Ile Ser Tyr Leu Pro Ser Phe
            2195                2200                2205
Phe Thr Lys Leu Glu Ser Thr Ser Pro Met Val Lys Ser Lys Lys Gln
            2210                2215                2220
Glu Ile Phe Arg Lys Leu Asn Ser Ser Gly Gly Gly Asp Ser Asp Met
2225                2230                2235                2240
Ala Ala Ala Gln Pro Gly Thr Glu Ile Phe Asn Leu Pro Ala Val Thr
            2245                2250                2255
Thr Ser Gly Ala Val Ser Ser Arg Ser His Ser Phe Ala Asp Pro Ala
            2260                2265                2270
Ser Asn Leu Gly Leu Glu Asp Ile Ile Arg Lys Ala Leu Met Gly Ser
            2275                2280                2285
Phe Asp Asp Lys Val Glu Asp His Gly Val Val Met Ser His Pro Val
            2290                2295                2300
Gly Ile Met Pro Gly Ser Ala Ser Thr Ser Val Val Thr Ser Ser Glu
2305                2310                2315                2320
Ala Arg Arg Asp Glu Gly Glu Pro Ser Pro His Ala Gly Val Cys Lys
            2325                2330                2335
Pro Lys Leu Ile Asn Lys Ser Asn Ser Arg Lys Ser Lys Ser Pro Ile
            2340                2345                2350
Pro Gly Gln Ser Tyr Leu Gly Thr Glu Arg Pro Ser Ser Val Ser Ser
            2355                2360                2365
Val His Ser Glu Gly Asp Tyr His Arg Gln Thr Pro Gly Trp Ala Trp
            2370                2375                2380
Glu Asp Arg Pro Ser Ser Thr Gly Ser Thr Gln Phe Pro Tyr Asn Pro
2385                2390                2395                2400
Leu Thr Ile Arg Met Leu Ser Ser Thr Pro Thr Gln Ile Ala Cys
            2405                2410                2415
Ala Pro Ser Ala Ile Thr Gln Ala Ala Pro His Gln Gln Asn Arg Ile
            2420                2425                2430
Trp Glu Arg Glu Pro Ala Pro Leu Leu Ser Ala Gln Tyr Glu Thr Leu
            2435                2440                2445
Ser Asp Ser Asp Asp
            2450

<210> SEQ ID NO 5
<211> LENGTH: 27
<212> TYPE: DNA
<213> ORGANISM: Artificial Sequence
<220> FEATURE:
<223> OTHER INFORMATION: oligonucleotide antisense primer
```

```
<400> SEQUENCE: 5
cgcggatccc agttctgagt tcacgtc                                    27

<210> SEQ ID NO 6
<211> LENGTH: 26
<212> TYPE: DNA
<213> ORGANISM: Artificial Sequence
<220> FEATURE:
<223> OTHER INFORMATION: oligonucleotide sense primer

<400> SEQUENCE: 6
cggaattctc aagcgagagt tgctgg                                     26

<210> SEQ ID NO 7
<211> LENGTH: 26
<212> TYPE: DNA
<213> ORGANISM: Artificial Sequence
<220> FEATURE:
<223> OTHER INFORMATION: oligonucleotide sense primer

<400> SEQUENCE: 7
cggaattcaa cacagcccga tactgt                                     26

<210> SEQ ID NO 8
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 8
gctctagaac ctgatcgtac tga                                        23

<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9
cggggtacct cgcgttggtt gtgtt                                      25
```